(12) United States Patent
Coates et al.

(10) Patent No.: US 12,252,491 B2
(45) Date of Patent: Mar. 18, 2025

(54) IL-17A INHIBITORS

(71) Applicant: Eli Lilly and Company, Indianapolis, IN (US)

(72) Inventors: David Andrew Coates, New Palestine, IN (US); Kwame Frimpong, Indianapolis, IN (US); William Glen Holloway, Brownsburg, IN (US); Brian Spencer Jones, Indianapolis, IN (US); Adam Marc Levinson, Astoria, NY (US); Charles Willis Lugar, III, McCordsville, IN (US); Michael Enrico Richett, Indianapolis, IN (US); Brian Morgan Watson, Carmel, IN (US); Michael Edward Woodman, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 932 days.

(21) Appl. No.: 17/419,997

(22) PCT Filed: Jan. 3, 2020

(86) PCT No.: PCT/US2020/012115
§ 371 (c)(1),
(2) Date: Jun. 30, 2021

(87) PCT Pub. No.: WO2020/146194
PCT Pub. Date: Jul. 16, 2020

(65) Prior Publication Data
US 2022/0073526 A1    Mar. 10, 2022

Related U.S. Application Data

(60) Provisional application No. 62/842,770, filed on May 3, 2019, provisional application No. 62/789,247, filed on Jan. 7, 2019.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................. C07D 487/04
See application file for complete search history.

(56) References Cited

FOREIGN PATENT DOCUMENTS

| WO | 2013/116682 A1 | 8/2013 |
|---|---|---|
| WO | 2014/039595 A1 | 3/2014 |
| WO | 2014/066726 A1 | 5/2014 |
| WO | 2014/128093 A1 | 8/2014 |
| WO | 2016/037171 A1 | 3/2016 |
| WO | 2017/053868 A1 | 3/2017 |
| WO | 2017/087590 A1 | 5/2017 |
| WO | 2018/229079 A1 | 12/2018 |
| WO | 2019/138017 A1 | 7/2019 |
| WO | 2019/223718 A1 | 11/2019 |
| WO | 2020/127685 A1 | 6/2020 |
| WO | 2020/163554 A1 | 8/2020 |

OTHER PUBLICATIONS

International Search Report for PCT/US2020/012115, A3, Mar. 20, 2020, Eli Lilly and Company, Inc.
International Preliminary Report on Patentability for PCT/US2020/012115, A3, Jul. 22, 2021, Eli Lilly and Company, Inc.
Espada, et. al., A Binding Site on IL-17A for Inhibitory Macrocycles Revealed by Hydrogen/Deuterium Exchange Mass Spectrometry, J. Med. Chem. 2016, 59, 2255-2260.

*Primary Examiner* — Andrew D Kosar
*Assistant Examiner* — John D McAnany
(74) *Attorney, Agent, or Firm* — Dan L. Wood

(57) ABSTRACT

The invention provides certain difluorocyclohexyl-imidazopyridazinyl-imidazolidinone compounds of formula II as IL-17A inhibitors, pharmaceutical compositions thereof, and methods of using a compound of formula II to treat certain symptoms of psoriasis, rheumatoid arthritis or multiple sclerosis.

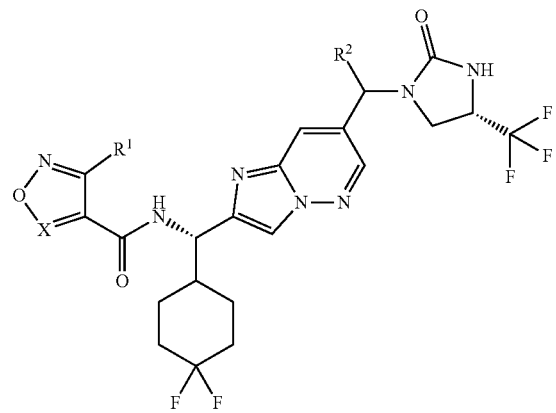

(II)

18 Claims, No Drawings
Specification includes a Sequence Listing.

SEQUENCE LISTING

<160> NUMBER OF SEQ ID NOS: 3

<210> SEQ ID NO 1
<211> LENGTH: 176
<212> TYPE: PRT
<213> ORGANISM: Artificial sequence
<220> FEATURE:
<223> OTHER INFORMATION: Synthetic construct

<400> SEQUENCE: 1

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala Gly Leu Asn Asp Ile
145                 150                 155                 160

Phe Glu Ala Gln Lys Ile Glu Trp His Glu His His His His His
                165                 170                 175

<210> SEQ ID NO 2
<211> LENGTH: 323
<212> TYPE: PRT
<213> ORGANISM: Artificial sequence
<220> FEATURE:
<223> OTHER INFORMATION: Synthetic construct

<400> SEQUENCE: 2

Met Ala Leu Lys Asp Asn Thr Val Pro Leu Lys Leu Ile Ala Leu Leu
1               5                   10                  15

Ala Asn Gly Glu Phe His Ser Gly Glu Gln Leu Gly Glu Thr Leu Gly
            20                  25                  30

Met Ser Arg Ala Ala Ile Asn Lys His Ile Gln Thr Leu Arg Asp Trp
        35                  40                  45

Gly Val Asp Val Phe Thr Val Pro Gly Lys Gly Tyr Ser Leu Pro Glu
    50                  55                  60

Pro Ile Gln Leu Leu Asn Ala Lys Gln Ile Leu Gly Gln Leu Asp Gly
65                  70                  75                  80

Gly Ser Val Ala Val Leu Pro Val Ile Asp Ser Thr Asn Gln Tyr Leu
                85                  90                  95

Leu Asp Arg Ile Gly Glu Leu Lys Ser Gly Asp Ala Cys Ile Ala Glu
            100                 105                 110

Tyr Gln Gln Ala Gly Arg Gly Arg Arg Gly Arg Lys Trp Phe Ser Pro
        115                 120                 125

Phe Gly Ala Asn Leu Tyr Leu Ser Met Phe Trp Arg Leu Glu Gln Gly
    130                 135                 140

Pro Ala Ala Ala Ile Gly Leu Ser Leu Val Ile Gly Ile Val Met Ala
145                 150                 155                 160

Glu Val Leu Arg Lys Leu Gly Ala Asp Lys Val Arg Val Lys Trp Pro
                165                 170                 175

Asn Asp Leu Tyr Leu Gln Asp Arg Lys Leu Ala Gly Ile Leu Val Glu
            180                 185                 190

Leu Thr Gly Lys Thr Gly Asp Ala Ala Gln Ile Val Ile Gly Ala Gly
        195                 200                 205

Ile Asn Met Ala Met Arg Arg Val Glu Glu Ser Val Val Asn Gln Gly
    210                 215                 220

Trp Ile Thr Leu Gln Glu Ala Gly Ile Asn Leu Asp Arg Asn Thr Leu
225                 230                 235                 240

Ala Ala Met Leu Ile Arg Glu Leu Arg Ala Ala Leu Glu Leu Phe Glu
                245                 250                 255

Gln Glu Gly Leu Ala Pro Tyr Leu Ser Arg Trp Glu Lys Leu Asp Asn
            260                 265                 270

Phe Ile Asn Arg Pro Val Lys Leu Ile Gly Asp Lys Glu Ile Phe
        275                 280                 285

Gly Ile Ser Arg Gly Ile Asp Lys Gln Gly Ala Leu Leu Leu Glu Gln
    290                 295                 300

Asp Gly Ile Ile Lys Pro Trp Met Gly Gly Glu Ile Ser Leu Arg Ser
305                 310                 315                 320

Ala Glu Lys

<210> SEQ ID NO 3
<211> LENGTH: 331
<212> TYPE: PRT

<213> ORGANISM: Artificial sequence
<220> FEATURE:
<223> OTHER INFORMATION: Synthetic construct

<400> SEQUENCE: 3

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asp Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asp Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Leu Val Pro
305                 310                 315                 320

Arg Gly Ser Asp Tyr Lys Asp Asp Asp Lys
                325                 330
```

IL-17A INHIBITORS

The invention provides certain difluorocyclohexyl-imidazopyridazinyl-imidazolidinone compounds, pharmaceutical compositions thereof, and methods for their use in the treatment of psoriasis, spondyloarthritis, rheumatoid arthritis and multiple sclerosis.

Immunological functions are critical for the maintenance of homeostasis and effective response to disease, and abnormal immune responses are established contributors to the pathophysiology of autoimmune disease. In certain disease states, some of the critical pathways contributing to these abnormal autoimmune responses have been discovered to be effective approaches for therapeutic intervention. One recent example is the development of interleukin (IL)-17 inhibitors. IL-17A is well-established as a pro-inflammatory cytokine which plays a key part in chronic inflammation and is a major driver of tissue damage. IL-17A induces normal immune and inflammatory responses to pathogens, but can also contribute to chronic autoimmune diseases including psoriasis, spondyloarthritis, rheumatoid arthritis and multiple sclerosis.

The IL-17 family consists of six cytokines (IL-17A through IL-17F). IL-17 receptor (IL-17R) refers to the heterodimer formed by the IL-17RA and IL-17RC subunits. IL-17A is a major pathological cytokine secreted from Th17 cells which may act as a homodimer or a heterodimer to signal through IL-17R. (Isono, F., et al., Inhibiting RORgt/Th17 axis for autoimmune disorders, *Drug Discovery Today* (2014) Vol. 19(8) 1205-1211). Within the skin and joints, IL-17A acts on cellular targets, including keratinocytes, endothelial cells, fibroblasts, osteoclasts, chondrocytes, and osteoblasts, to stimulate production of various antimicrobial peptides, chemokines, and proinflammatory and proliferative cytokines, which, in turn, promote tissue inflammation and bone remodeling. The critical importance of the IL-23/IL-17A axis to the pathogenesis of psoriatic disease has resulted in many new biologic treatments targeting these cytokines. These biologics dramatically improve skin and joint symptoms in patients with moderate-to-severe psoriasis and psoriatic arthritis.

There are currently no highly efficacious orally administered treatments for moderate to severe psoriasis. A small molecule IL-17A inhibitor may provide efficacy comparable to anti-IL-17A antibodies for psoriasis and/or other IL-17A-dependent diseases, such as psoriatic arthritis. While the inhibition of IL-17A could, in some instances, increase susceptibility to opportunistic infections, an orally available small molecule inhibitor which had a relatively short half-life may provide for an improved agent for management of this risk. An oral agent may enable the patient to stop taking the drug, and rapidly clear the inhibitor from the body, thus enabling more rapid recovery of the ability to respond to an infection. In addition, anti-drug antibodies against anti-IL-17A antibodies may arise in some patients, and may reduce the efficacy of antibodies directed to IL-17A over time. This inactivation pathway would not be operative for small molecule IL-17A inhibitors.

WO 2014/066726 recites certain compounds as modulators of IL-17 activity and their uses in the treatment of medical conditions such as inflammatory diseases, and other IL-17-associated disorders.

There remains a need for small molecule IL-17A inhibitors to provide improved and/or orally available treatments for IL-17-mediated diseases. The present invention provides certain novel compounds that are inhibitors of IL-17A and demonstrate an advantageous combination of pharmacological properties, such as potent inhibition of IL-17A and oral bioavailability, for example. As such, compounds of the present invention are believed to be useful in the treatment of psoriasis, rheumatoid arthritis and multiple sclerosis. The compounds of the present invention may provide an alternative treatment for such disorders. The compounds of the present invention may provide inhibitors of IL-17A with an improved combination of efficacy, safety, and/or tolerability for certain patients.

The present invention provides a compound of formula II:

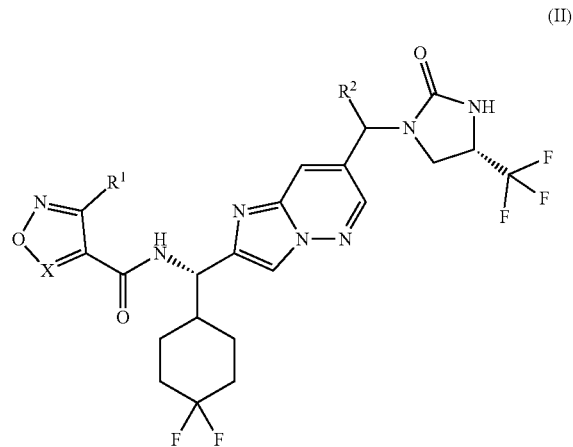

(II)

wherein:

X is CH, or N;

$R^1$ is —CH$_3$, —CH$_2$F, —CHF$_2$, —CF$_3$, —CH$_2$CH$_3$, —CH$_2$CF$_3$, —CH(CH$_3$)$_2$, —CH$_2$CHF$_2$,

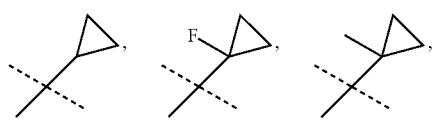

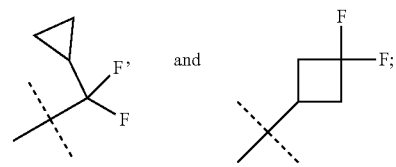

and $R^2$ is —H or —CH$_2$OCH$_3$;

or a pharmaceutically acceptable salt thereof.

The present invention provides a compound of formula I:

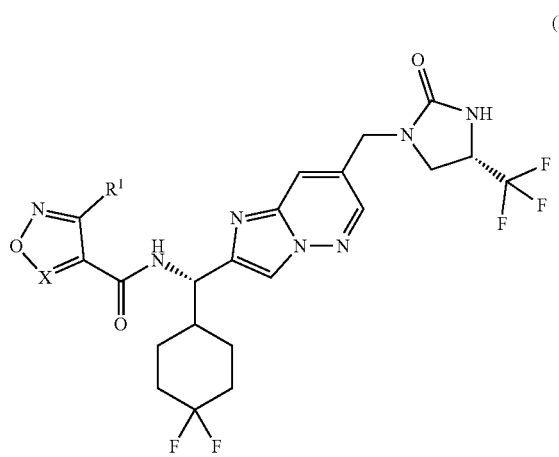

wherein:
X is CH, or N,
R¹ is —CH$_3$, —CH$_2$F, —CHF$_2$, —CF$_3$, —CH$_2$CH$_3$, —CH$_2$CF$_3$, —CH(CH$_3$)$_2$, —CH$_2$CHF$_2$,

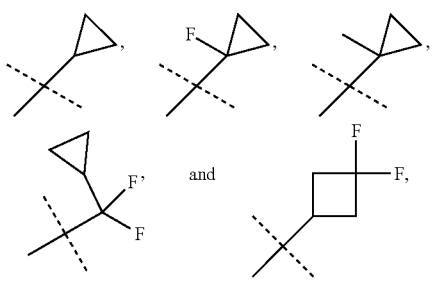

or a pharmaceutically acceptable salt thereof.

A particular compound of formula I is a compound of formula Ia:

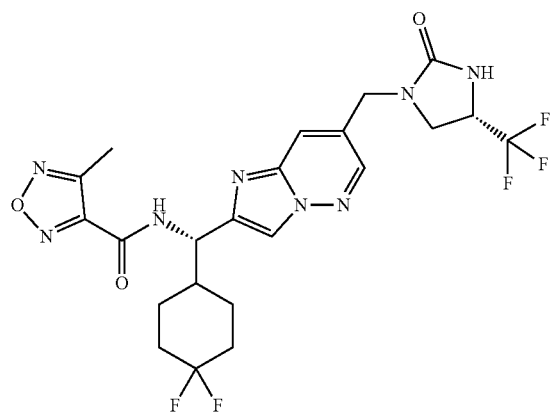

or a pharmaceutically acceptable salt thereof, which can also be named as N—[(S)-(4,4-difluorocyclohexyl)-7-[[(4S)-2-oxo-4-(trifluoromethyl)imidazolidin-1-yl]methyl]imidazo[1,2-b]pyridazin-2-yl]methyl]-4-methyl-1,2,5-oxadiazole-3-carboxamide.

A particular compound of formula I is a compound of formula Ib:

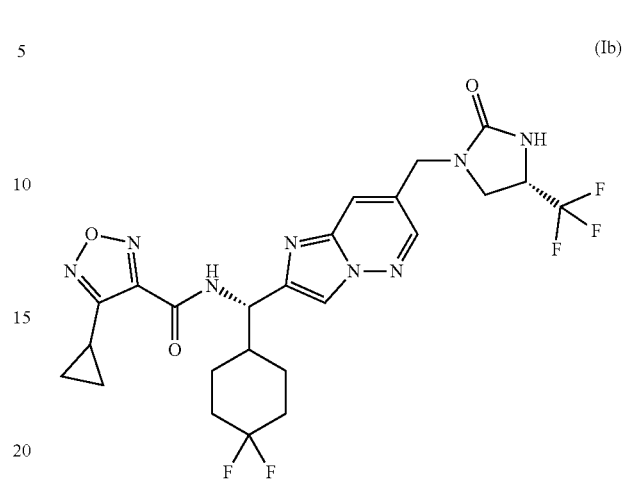

or a pharmaceutically acceptable salt thereof, which can also be named as 4-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide.

A particular compound of formula II is a compound of formula IIa:

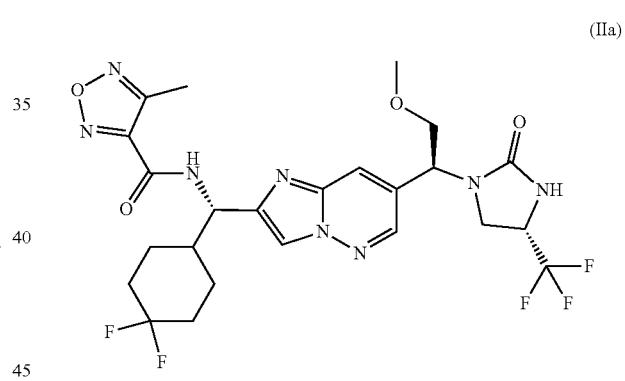

or a pharmaceutically acceptable salt thereof, which can also be named as N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide.

Further, the present invention provides a pharmaceutical composition comprising a compound of formula I and/or II, or a pharmaceutically acceptable salt thereof, and a pharmaceutically acceptable carrier, diluent or excipient.

The following particular embodiments are compounds and/or salts of formula II.

The present invention provides a compound of formula II wherein X is CH.

The present invention provides a compound of formula II wherein X is N.

The present invention provides a compound of formula II wherein R² is —CH$_2$OCH$_3$.

The following particular embodiments are compounds and/or salts of formula I.

The present invention provides a compound of formula I wherein X is CH.

The present invention provides a compound of formula I wherein X is N.

The present invention provides a compound which is 3-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide, or a pharmaceutically acceptable salt thereof.

The present invention provides a compound which is N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(difluoromethyl)isoxazole-4-carboxamide, or a pharmaceutically acceptable salt thereof.

The present invention provides a compound which is 4-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide, or a pharmaceutically acceptable salt thereof.

The present invention provides a compound which is N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-(trifluoromethyl)-1,2,5-oxadiazole-3-carboxamide, or a pharmaceutically acceptable salt thereof.

The present invention provides a compound which is N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-(difluoromethyl)-1,2,5-oxadiazole-3-carboxamide, or a pharmaceutically acceptable salt thereof.

Further, the present invention provides a compound selected from the group consisting of:

3-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-ethyl-isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-methyl-isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(difluoromethyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(1,1-difluoroethyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(fluoromethyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(2,2-difluoroethyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(2-fluoroethyl)isoxazole-4-carboxamide;

3-(3,3-difluorocyclobutyl)-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(trifluoromethyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(1-fluorocyclopropyl)isoxazole-4-carboxamide;

3-[cyclopropyl(difluoro)methyl]-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(1-methylcyclopropyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-(1-fluoro-1-methyl-ethyl)isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-3-isopropyl-isoxazole-4-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-ethyl-1,2,5-oxadiazole-3-carboxamide;

4-isopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-methoxy-1,2,5-oxadiazole-3-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-(2,2,2-trifluoroethyl)-1,2,5-oxadiazole-3-carboxamide;

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-(2,2,2-trifluoroethyl)-1,2,5-oxadiazole-3-carboxamide;

4-cyclopropyl-N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-1,2,5-oxadiazole-3-carboxamide;

3-cyclopropyl-N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]isoxazole-4-carboxamide;

N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-(difluoromethyl)-1,2,5-oxadiazole-3-carboxamide; and N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-(trifluoromethyl)-1,2,5-oxadiazole-3-carboxamide, or a pharmaceutically acceptable salt thereof.

Further, the present invention provides a pharmaceutical composition comprising compound and/or salt of one of the particular embodiments of the preceding list immediately above, and a pharmaceutically acceptable carrier, diluent or excipient.

Compounds of the present invention are potent inhibitors of IL-17A, and up on administration to a patient in need thereof, may provide therapeutic benefits while avoiding certain problems associated with biological IL-17A signaling antagonists, such as IL-17 antibodies. As such, compounds of the present invention are believed to be useful for the treatment of conditions in which excessive IL-17A mediated signaling plays a role, and such as psoriasis, rheumatoid arthritis, spondyloarthritis and multiple sclerosis, including relief of certain immunologically-mediated symptoms. Compounds of the present invention are also believed to be useful in improving disease symptoms in psoriasis, rheumatoid arthritis, spondyloarthritis, multiple sclerosis, psoriatic arthritis, axial spondyloarthritis, ankylosing spondylitis, hidradenitis suppurativa, systemic lupus erythematosus, palmoplantar pustulosis (PPP), atopic dermatitis, asthma, and COPD.

Further, the present invention provides a compound of formula I and/or II, or a pharmaceutically acceptable salt thereof, for use in therapy. Further, the present invention provides a compound of formula Ia and/or IIa, or a pharmaceutically acceptable salt thereof, for use in therapy.

In another embodiment, the present invention provides a pharmaceutical composition comprising the compound of formula I and/or II, or a pharmaceutically acceptable salt thereof, and one or more pharmaceutically acceptable carriers, diluents, or excipients. Furthermore, this embodiment of the invention provides a pharmaceutical composition for treating psoriasis, comprising the compound of formula I and/or II, or a pharmaceutically acceptable salt thereof, and one or more pharmaceutically acceptable excipients, carriers, or diluents. In another embodiment the invention provides a pharmaceutical composition for treating rheumatoid arthritis, comprising the compound of formula I and/or II, or a pharmaceutically acceptable salt thereof, and one or more pharmaceutically acceptable excipients, carriers, or diluents. In another embodiment the invention provides a pharmaceutical composition for treating multiple sclerosis, comprising the compound of formula I and/or II, or a pharmaceutically acceptable salt thereof, and one or more pharmaceutically acceptable excipients, carriers, or diluents.

Further, the present invention provides a method of treating a disease or disorder selected from the group consisting of psoriasis, rheumatoid arthritis, spondyloarthritis, multiple sclerosis, psoriatic arthritis, axial spondyloarthritis, ankylosing spondylitis, hidradenitis suppurativa, systemic lupus erythematosus, palmoplantar pustulosis (PPP), atopic dermatitis, asthma, and/or COPD, comprising administering to a patient in need thereof an effective amount of a compound of formula I and/or II, or a pharmaceutically acceptable salt thereof. Further, the present invention provides a method of treating psoriasis, comprising administering to a patient in need thereof an effective amount of a compound of formula I and/or II, or a pharmaceutically acceptable salt thereof. Further, the present invention provides a method of treating rheumatoid arthritis, comprising administering to a patient in need thereof an effective amount of a compound of formula I and/or II, or a pharmaceutically acceptable salt thereof. Further, the present invention provides a method of treating multiple sclerosis, comprising administering to a patient in need thereof an effective amount of a compound of formula I and/or II, or a pharmaceutically acceptable salt thereof. Further, the present invention provides a method of treating spondyloarthritis, comprising administering to a patient in need thereof an effective amount of a compound of formula I and/or II, or a pharmaceutically acceptable salt thereof.

In one embodiment, the present invention provides a compound of formula I and/or II, or a pharmaceutically acceptable salt thereof, for use in the treatment of psoriasis. In another particular embodiment the invention provides a compound of formula I and/or II, or a pharmaceutically acceptable salt thereof, for use in the treatment of rheumatoid arthritis. In another particular embodiment the invention provides a compound of formula I and/or II, or a pharmaceutically acceptable salt thereof, for use in treating multiple sclerosis. In another particular embodiment the invention provides a compound of formula I and/or II, or a pharmaceutically acceptable salt thereof, for use in treating spondyloarthritis. In another particular embodiment the invention provides a compound of formula I and/or II, or a pharmaceutically acceptable salt thereof, for use in treating a disease or disorder selected from the group consisting of psoriasis, rheumatoid arthritis, spondyloarthritis, multiple sclerosis, psoriatic arthritis, axial spondyloarthritis, ankylosing spondylitis, hidradenitis suppurativa, systemic lupus erythematosus, palmoplantar pustulosis (PPP), atopic dermatitis, asthma, and/or COPD.

In yet another embodiment, the present invention provides the use of a compound of formula I and/or II, or a pharmaceutically acceptable salt thereof, in the manufacture of a medicament for the treatment of psoriasis. In yet another embodiment, the present invention provides the use of a compound of formula I and/or II, or a pharmaceutically acceptable salt thereof, in the manufacture of a medicament for the treatment of rheumatoid arthritis. In yet another embodiment, the present invention provides the use of a compound of formula I and/or II, or a pharmaceutically acceptable salt thereof, in the manufacture of a medicament for the treatment of multiple sclerosis. In yet another embodiment, the present invention provides the use of a compound of formula I and/or II, or a pharmaceutically acceptable salt thereof, in the manufacture of a medicament for the treatment of spondyloarthritis.

The compounds or salts of the present invention are usually administered in the form of pharmaceutical compositions comprising the compound of formula I and/or II, or a pharmaceutically acceptable salt thereof, as an active ingredient, and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., 21st ed., Lippincott Williams & Wilkins Co., 2005).

Compositions of compounds of formula I, and/or Ia, and/or Ib, and/or II, and/or IIa, or pharmaceutically acceptable salts thereof, are preferably formulated in a unit dosage forms, each dosage containing from about 0.5 to about 800 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient. It will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms. It is contemplated that the compound of the invention, as for example in a pharmaceutical composition of the invention, will be used to treat psoriasis, rheumatoid arthritis and/or multiple sclerosis, by chronic administration.

As used herein, the term "patient" refers to a mammal, preferably a human. As used herein, the terms "treatment", "treating", or "mitigating" are intended to refer to all processes wherein there may be a slowing, interrupting, arresting, controlling, or stopping of the progression of an existing disorder and/or a reduction in symptoms thereof, but does not necessarily indicate a total elimination of all symptoms. As used herein, the term "effective amount" of a compound of formula I, and/or Ia, and/or II, and/or IIa, refers to an amount, that is a dosage, which is effective in inhibiting an IL-17A mediated response in a patient. A preferred "effective amount" is determined as an amount that can treat or eliminate the signs and symptoms of moderate to severe psoriasis in the patient, as compared to the patient when untreated. In determining an effective amount or dose of a compound of formula I and/or II, a number of factors are considered, including, but not limited to the compound to be administered and its particular formulation; the patients size, age, and general health; the degree of involvement or the severity of the disorder; the response of the individual patient; the mode of administration; and other relevant circumstances.

"Pharmaceutically acceptable salts" or "a pharmaceutically acceptable salt" refers to the relatively non-toxic, inorganic and organic salt or salts of the compound of the present invention. It will be understood by the skilled artisan that compounds of the present invention are capable of forming salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

Certain abbreviations are defined as follows: "CDI" refers 1,1'-carbonyldiimidazole; "DAST" refers to diethylaminosulfur trifluoride; "DBU" refers to 1,8-diazabicyclo[5.4.0]undec-7-ene; "DCC" refers to 1,3-dicyclohexylcarbodiimide; "DCE" refers to dichloroethane; "DCM" refers to dichloromethane; "DIC" refers to 1,3-diisopropylcarbodiimide; "DIEA" refers to N,N-diisopropylethylamine; "DMAP" refers to 4-dimethylaminopyridine; "DMSO" refers to dimethyl sulfoxide; "DTBPF" refers to 1,1'-bis(di-tert-butylphosphino)ferrocene; "EDCI" refers to 1-(3-dimethylaminopropyl)-3-ethylcarbodiimide hydrochloride; "EtOAc" refers to ethyl acetate; "EtOH" refers to ethanol and ethyl alcohol; "HATU" refers to (dimethylamino)-N,N-dimethyl(3H-[1,2,3]triazolo[4,5-b]pyridin-3-yloxy)methaniminium hexafluorophosphate; "HBTU" refers to (1H-benzotriazol-1-yloxy)(dimethylamino)-N,N-dimethylmethaniminium hexafluorophosphate; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "IL-17A" refers to interleukin 17A; "IPA" refers to isopropanol and isopropyl alcohol; "LDA" refers to lithium diisopropylamide; "MeOH" refers to methanol and methyl alcohol; "MTBE" refers to methyl tert-butyl ether; "NBS" refers to N-bromosuccinimide; "NCS" refers to N-chlorosuccinimide; "NMP" refers to N-methylpyrrolidinone; "Pd$_2$(dba)$_3$" refers to tris(dibenzylideneacetone)dipalladium(0); PdCl$_2$(dppf) refers to [1,1'-bis(diphenylphosphino)ferrocene]dichloropalladium(II); "PCC" refers to pyridinium chlorochromate; "PyBOP" refers to (benzotriazol-1-yl-oxytripyrrolidinophosphonium hexafluorophosphate); "PyBrOP" refers to bromo(tri-pyrrolidinyl)phosphoniumhexafluorophosphate; "Rh-COD-[(S)-MaxPhos]-BF4" refers to [((R)-tert-butylmethylphosphino)(di-tert-butylphosphino)amine](1,5-cyclooctadiene) rhodium(I) tetrafluoroborate; "SCX" refers to strong cation exchange; "SFC" refers to supercritical fluid chromatography; "TEA" refers to triethylamine; "TFA" refers to trifluoroacetic acid; "THF" refers to tetrahydrofuran; "Xantphos" refers to 4,5-bis(diphenylphosphino)-9,9-dimethylxanthene.

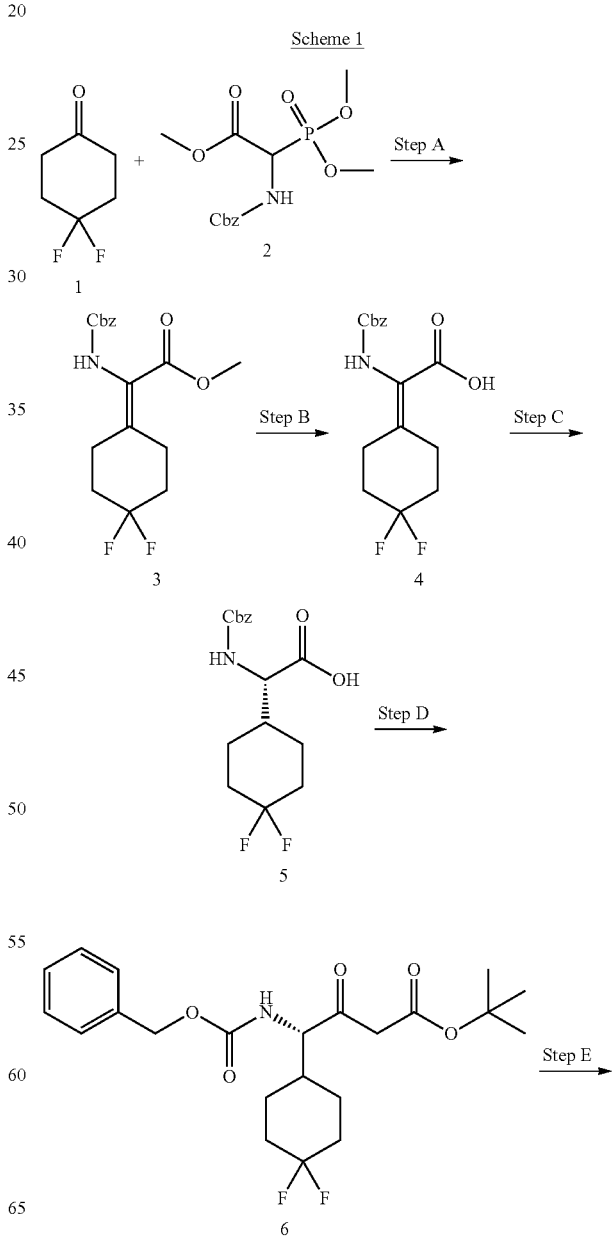

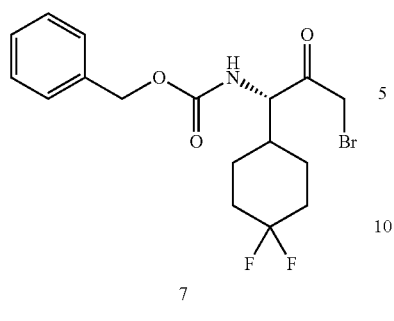

In scheme 1, step A, a Wittig-Horner reaction may be performed under conditions well known in the art between compound (1) and compound (2) using a suitable organic base such as DBU in a suitable solvent such as NMP to give compound (3). Step B depicts the basic hydrolysis of the ester on compound (3) with aqueous NaOH in a suitable solvent such as THF at ambient temperature to give compound (4). An asymmetric hydrogenation on compound (4) using an appropriate catalyst such as Rh-COD-[(S)-Max-Phos]-BF4 in a suitable solvent such as MeOH under a hydrogen atmosphere to give compound (5) is shown in step C. tert-Butylacetate is treated with a suitable organolithium reagent such as LDA in a solvent such as THF at −78° C. and added to CDI activated compound (5) also at −78° C. in THF to form compound (6) as depicted in step D. Step E shows the bromination of compound (6) with an appropriate brominating agent such as NBS using a suitable organic base such as 2,6-dimethylpyridine in a suitable solvent such as MeOH. After bromination, decarboxylation is performed using a suitable acid such as TFA in a solvent such as toluene to give compound (7).

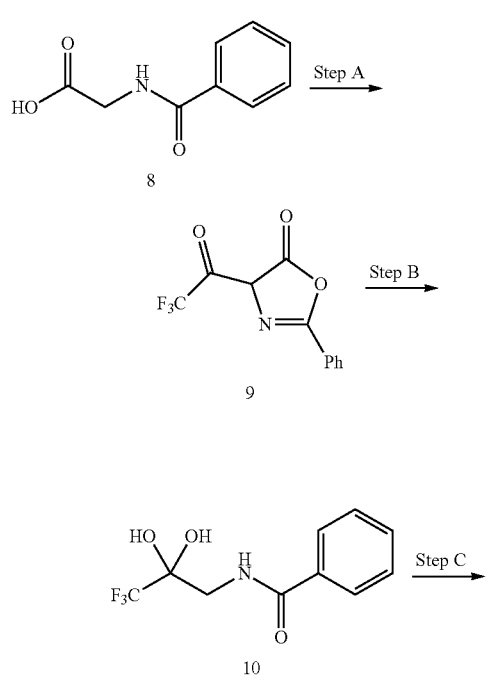

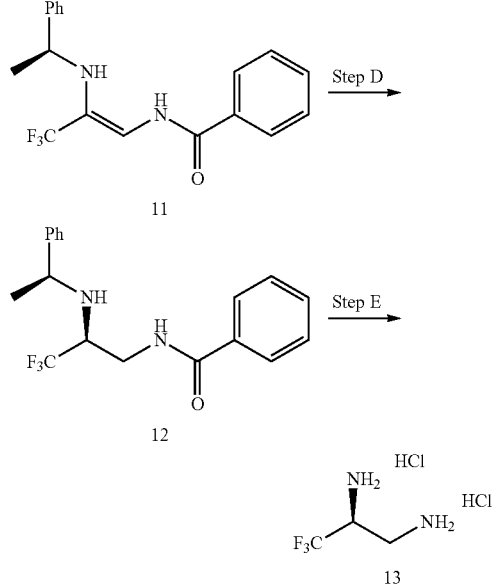

Scheme 2, step A depicts a Dakin-West reaction well known in the art performed on compound (8) to form compound (9) through the use of trifluoroacetic anhydride in a suitable solvent such as acetone at around 0° C. Step B depicts the hydrolysis of compound (9) with water at ambient temperature to give compound (10). Treatment of compound (10) with an amine such as (1S)-1-phenylethanamine in a solvent such as toluene at 105° C. yields compound (11) as shown in step C. In step D, an asymmetric hydrogenation can be performed on compound (11) using an appropriate catalyst such as Rh-COD-[(S)-MaxPhos]-BF4 in a suitable solvent such as t-amyl alcohol under a hydrogen atmosphere to give compound (12). The deprotection of compound (12) with HCl in a suitable solvent system such as dioxane and water at 95° C. to give compound (13) is depicted in step E.

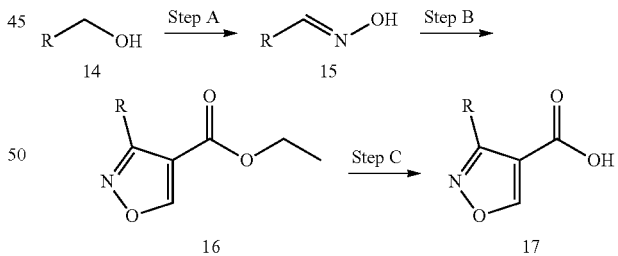

Scheme 3, step A depicts the oxidation and oxime formation of compound (14) through conditions well established in the art using a suitable oxidizing agent such as Dess-Martin periodinane or PCC in a solvent such as DCM to give the intermediate aldehyde which is then reacted with hydroxylamine hydrochloride in a suitable base/solvent system such as sodium bicarbonate and DCM or potassium bicarbonate in water and MeOH, to give compound (15). Step B shows a one pot transformation where compound (15) may be first treated with a suitable halogenating agent such as NBS or NCS in a suitable solvent such as DCM or chloroform to give a halogenated intermediate, which may then be treated with ethyl (E)-3-(dimethylamino)prop-2-enoate using a suitable organic base such as TEA in a suitable solvent such as DCM or chloroform to give the cyclized compound (16). Step C depicts the basic hydrolysis of the ester on compound (16) with a suitable base such as aqueous NaOH in a suitable solvent combination of solvents such as THF, MeOH, and water to give compound (17).

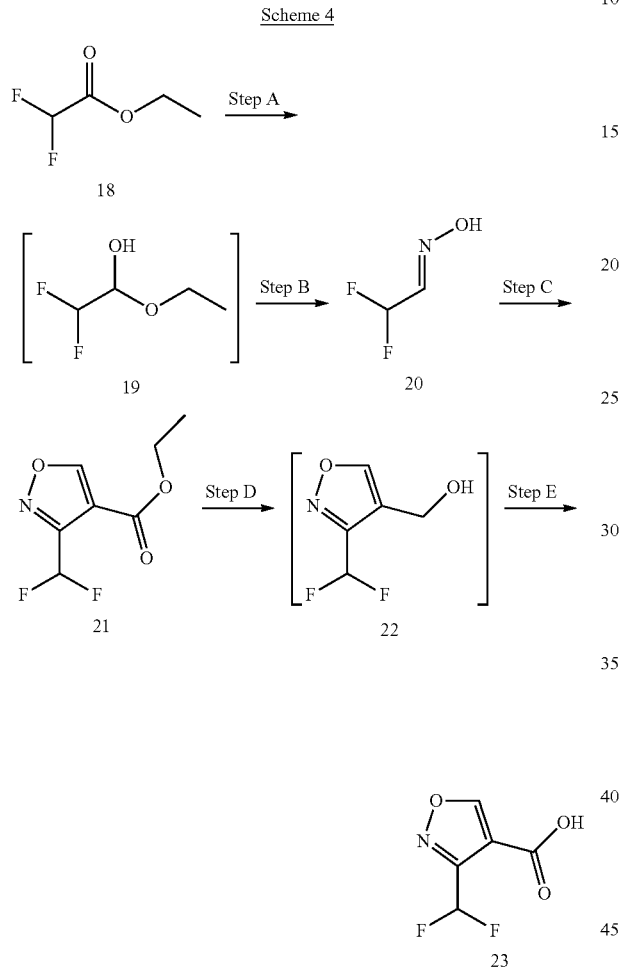

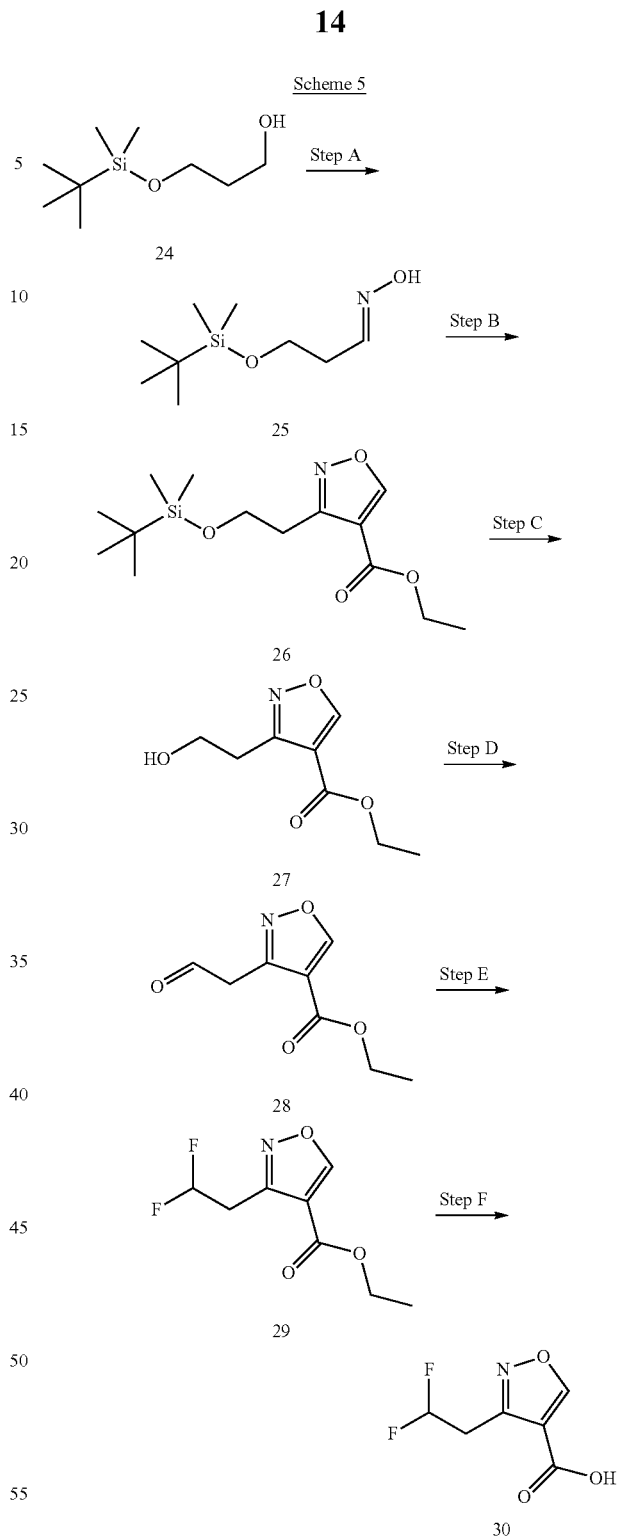

Scheme 4, step A depicts the partial reduction of compound (18) with a suitable reducing agent such as lithium aluminum hydride in a solvent such as diethyl ether at −78° C. to give compound (19). In step B, compound (19) may be added to hydroxylamine hydrochloride and a suitable base such as sodium bicarbonate in a solvent such as water at around 0° C. to form an oxime, compound (20). The transformation of compound (20) to compound (21) in step C is essentially analogous to that in Scheme 3, step B. One skilled in the art will recognize the reduction of compound (21) in step D using a suitable reducing agent such as diisobutylaluminum hydride in a solvent such as diethyl ether at a temperature of around 0° C. to give compound (22). Step E shows the oxidation of compound (22) using a suitable oxidizing agent such as chromium trioxide with sulfuric acid and water in a suitable solvent such as acetone at temperatures from 0° C. to ambient temperature to give compound (23).

Scheme 5, step A shows the transformation of compound (24) to compound (25) in step A which is essentially analogous to that in Scheme 3, step A. The transformation of compound (25) to compound (26) in step B is essentially analogous to that in Scheme 3, step B. One skilled in the art will recognize the deprotection of compound (26) to compound (27) with a suitable acid such as HCl in MeOH in a suitable solvent such as EtOH as shown in step C. Step D depicts the oxidation of compound (27) using a suitable oxidizing agent such as Dess-Martin periodinane in a solvent such as DCM to give compound (28). The fluorination of compound (28) is depicted in step E and may be performed using a suitable organic solvent such as DCM with a suitable fluorinating agent such as DAST at around −25° C. to give compound (29). The transformation of compound (29) to compound (30) in step F is essentially analogous to that in Scheme 3, step C.

Scheme 6

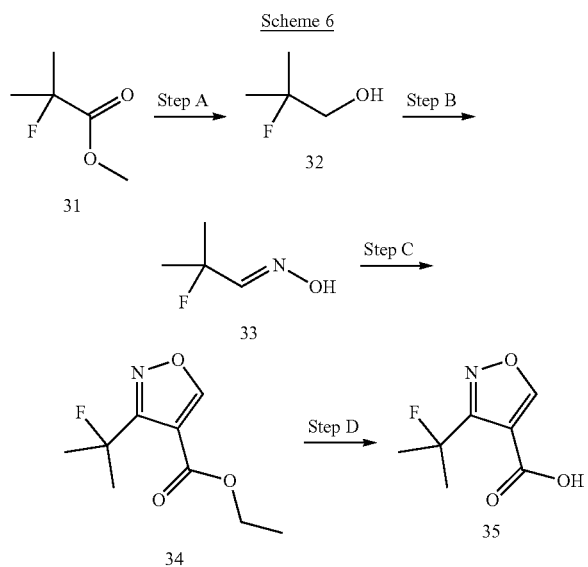

Scheme 6, step A depicts the reduction of compound (31) with a suitable reducing agent such as lithium aluminum hydride in a solvent such as diethyl ether at 0° C. to give compound (32). The transformation of compound (32) to compound (33) in step B is essentially analogous to that in Scheme 3, step A. The transformation of compound (33) to compound (34) in step C is essentially analogous to that in Scheme 3, step B. The transformation of compound (34) to compound (35) in step F is essentially analogous to that in Scheme 3, step C.

Scheme 7

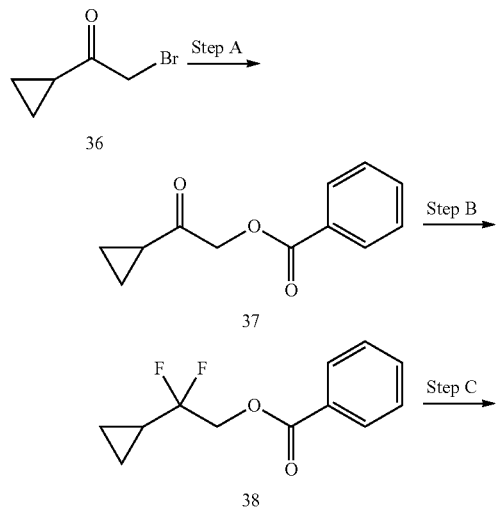

In scheme 7, step A, compound (36) is used to alkylate benzoic acid using a suitable base such as potassium carbonate in suitable solvent such as DMF to give compound (37). The fluorination of compound (37) to give compound (38) may be performed with a fluorinating agent such as DAST in a suitable solvent such as DCE as shown in step B. Step C depicts the deprotection of compound (38) with an aqueous base such as NaOH to give compound (39). The transformation of compound (39) to compound (40) in step D is essentially analogous to that in Scheme 3, step A. The transformation of compound (40) to compound (41) in step E is essentially analogous to that in Scheme 3, step B. The transformation of compound (41) to compound (42) in step F is essentially analogous to that in Scheme 3, step C.

Scheme 8

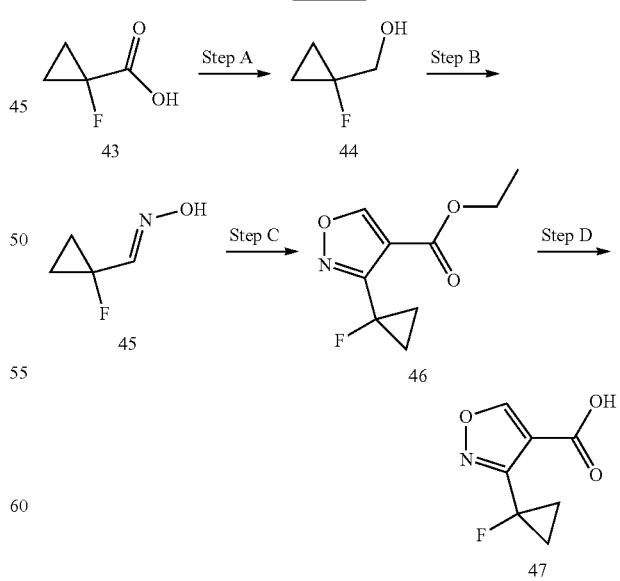

Scheme 8, step A depicts the reduction of compound (43) with a suitable reducing agent such as lithium aluminum hydride in a solvent such as diethyl ether at 0° C. to give compound (44). The transformation of compound (44) to compound (45) in step B is essentially analogous to that in Scheme 3, step A. The transformation of compound (45) to compound (46) in step C is essentially analogous to that in Scheme 3, step B. The transformation of compound (46) to compound (47) in step D is essentially analogous to that in Scheme 3, step C.

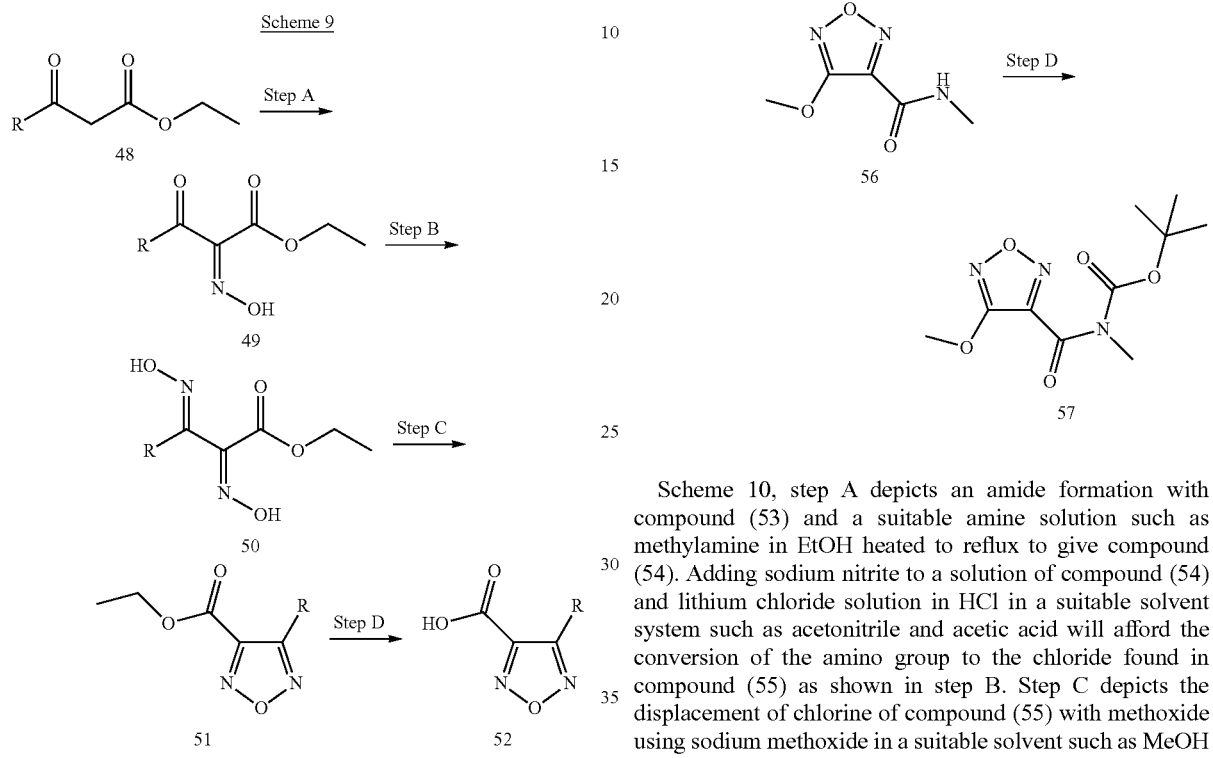

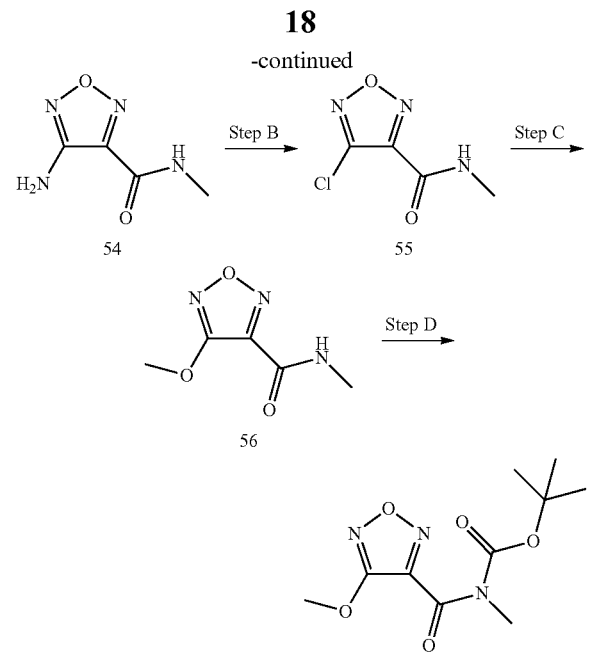

Scheme 9, step A depicts the reaction of compound (48) with aqueous sodium nitrate in a suitable solvent such as acetic acid to give compound (49). Step B shows the reaction of compound (49) and hydroxylamine hydrochloride in a suitable solvent such as EtOH with the use of either an appropriate base such as sodium acetate or an appropriate acid solution such as HCl in dioxane at temperatures of around 50-80° C. to give compound (50). The cyclization of compound (50) to compound (51) may be performed with CDI in a suitable solvent such as THF as shown in Step C. The hydrolysis of compound (51) may be performed using an aqueous base such as lithium hydroxide in a suitable solvent system such as THF and water to give compound (52) as depicted in step D. Alternatively, the hydrolysis of compound (51) to compound (52) may be performed using aqueous HCl at around 100° C. in an appropriate solvent system such as dioxane and water.

Scheme 10, step A depicts an amide formation with compound (53) and a suitable amine solution such as methylamine in EtOH heated to reflux to give compound (54). Adding sodium nitrite to a solution of compound (54) and lithium chloride solution in HCl in a suitable solvent system such as acetonitrile and acetic acid will afford the conversion of the amino group to the chloride found in compound (55) as shown in step B. Step C depicts the displacement of chlorine of compound (55) with methoxide using sodium methoxide in a suitable solvent such as MeOH to give compound (56). One skilled in the art will recognize the protection of compound (56) with di-tert-butyl dicarbonate in a suitable solvent such as DCM in the presence of a suitable base such as DMAP to give compound (57) as shown in step D.

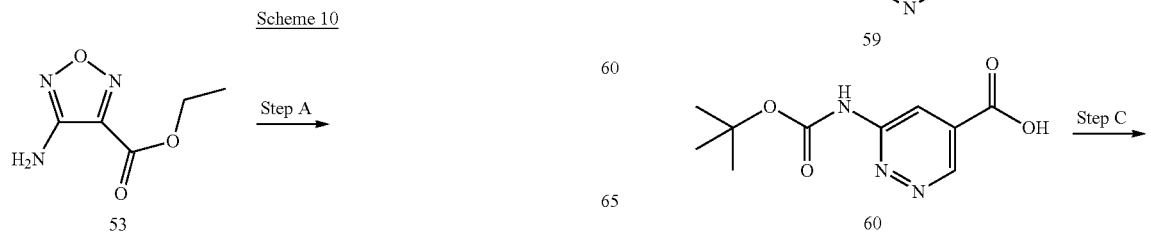

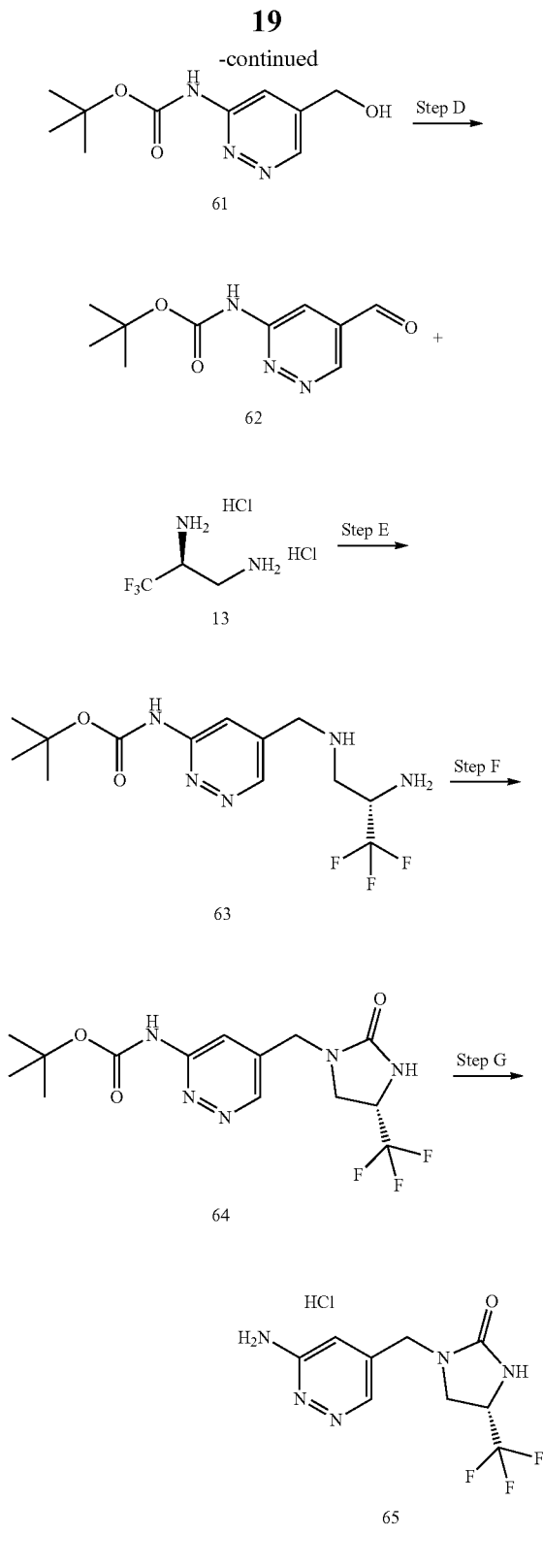

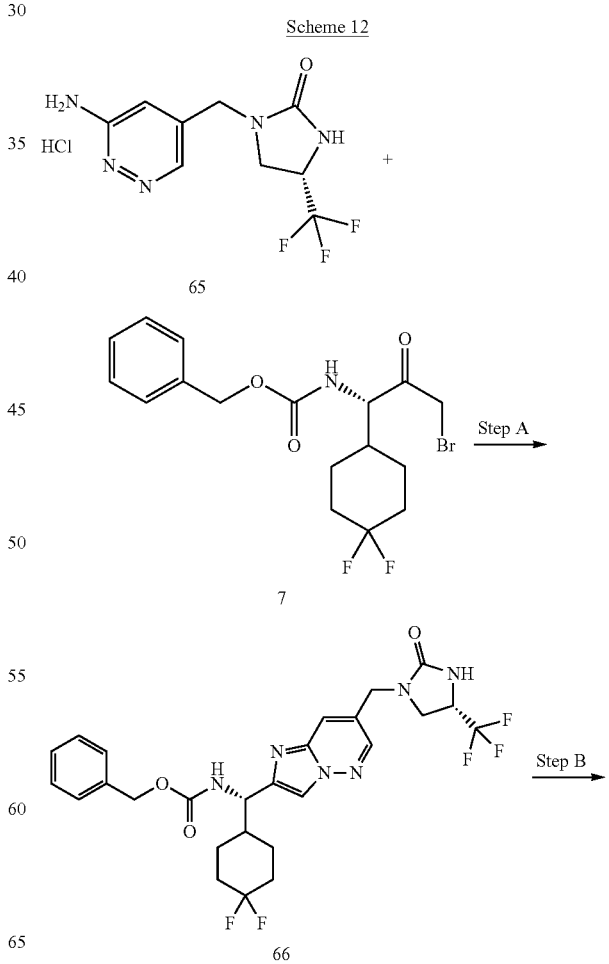

such as THF at ambient temperature to give compound (60). One skilled in the art would recognize the transformation in step C showing the reduction of the carboxylic acid on compound (60) through the formation of a mixed anhydride using a suitable chloroformate such as ethyl chloroformate followed by addition of a suitable reducing agent such as sodium borohydride in a solvent such as MeOH at temperatures from −78° C. to 0° C. to form compound (61). The oxidation of compound (61) may be performed using conditions well established in the art using a suitable oxidizing agent such as Dess-Martin periodinane in a solvent such as DCM to give compound (62) as shown in step D. A reductive amination may be performed with conditions well known in the art between compound (62) and compound (13) where the imine is first formed in a suitable solvent such as DCM using an organic base such as TEA with heating at 40° C. The resulting imine is reduced to give compound (63) with the addition of a suitable reducing agent such as sodium cyanoborohydride along with MeOH and acetic acid at ambient temperature as demonstrated in step E. CDI may be used in a suitable solvent such as THF to cyclize compound (63) to give compound (64) as depicted in step F. In step G, compound (64) can be deprotected under acidic conditions well known in the art such as using 4 M HCl in 1,4-dioxane in a solvent such as methanol at 50° C. to give compound (65).

Scheme 12

Scheme 11, step A, a Buchwald coupling can be performed under conditions well known in the art on compound (58) with an amine such as t-butyl carbamate using a suitable catalyst and ligand combination such as Pd$_2$(dba)$_3$ and DTBPF, and a suitable base such as potassium carbonate in a solvent such as toluene at around 75° C. to form compound (59). Step B depicts the basic hydrolysis of the ester on compound (59) with aqueous NaOH in a suitable solvent -continued

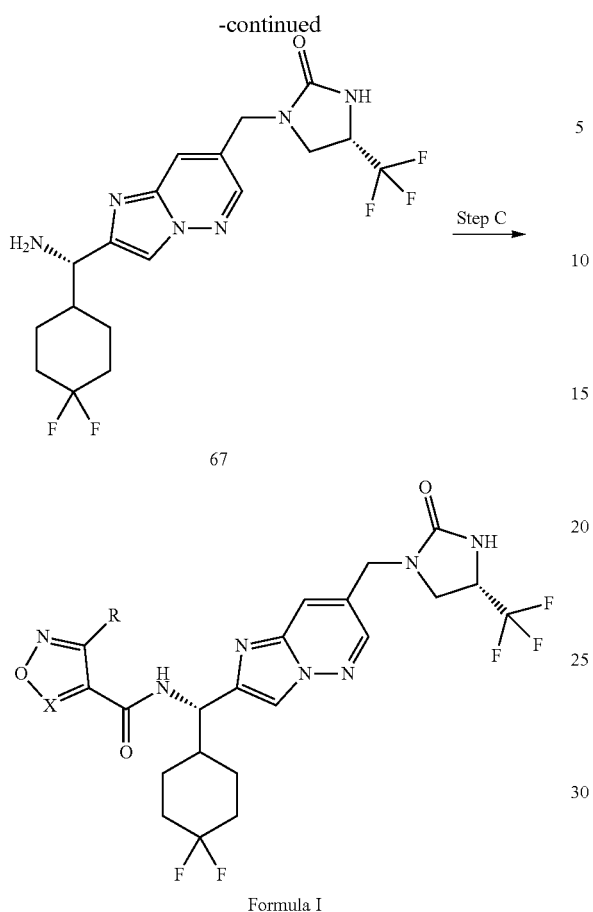

Formula I

Scheme 12, step A depicts an alkylation of a compound such as compound (65) with a haloketone such as compound (7) and subsequent cyclization to compound (66) utilizing trimethylborate and a suitable organic base such as DIEA in a suitable solvent such as THF heated to 80° C. in a sealed vessel. Step B shows the deprotection of compound (66) through hydrogenation conditions well known in the art using a catalyst such as 10% Pd/C in a suitable solvent such as EtOH under a hydrogen atmosphere to give compound (67). In step C, an amide coupling can be performed with compound (67) and various substituted heterocyclic carboxylic acids using an organic base such as DIEA and a suitable coupling agent such as HATU in a suitable solvent such as THF or DMF to give compounds of Formula I. One skilled in the art will recognize that there are several appropriate methods for amide formation resulting from the reaction of a carboxylic acid and an amine. For example, the reaction of the amine compound with an appropriate carboxylic acid in the presence of a coupling reagent with or without an organic base such as DIEA or TEA can provide a compound of step 4. Coupling reagents include carbodiimides, such as DCC, DIC, EDCI or a carbonyldiimidazole such as CDI. Amide coupling additives, such as HOBt and HOAt can also be used to enhance the reaction. Additionally, uronium or phosphonium salts of non-nucleophilic anions, such as HBTU, PyBOP, and PyBrOP could be used in place of the more traditional coupling reagents. An additive such as DMAP may be used to enhance the reaction. Alternatively, compound (67) could be acylated using the appropriate acid chloride in the presence of a base, such as TEA or pyridine to give compounds of Formula I. Compounds of Formula I may also be formed via transamidation between compound (67) and an activated heterocyclic amide in an appropriate solvent such as acetonitrile.

Scheme 13

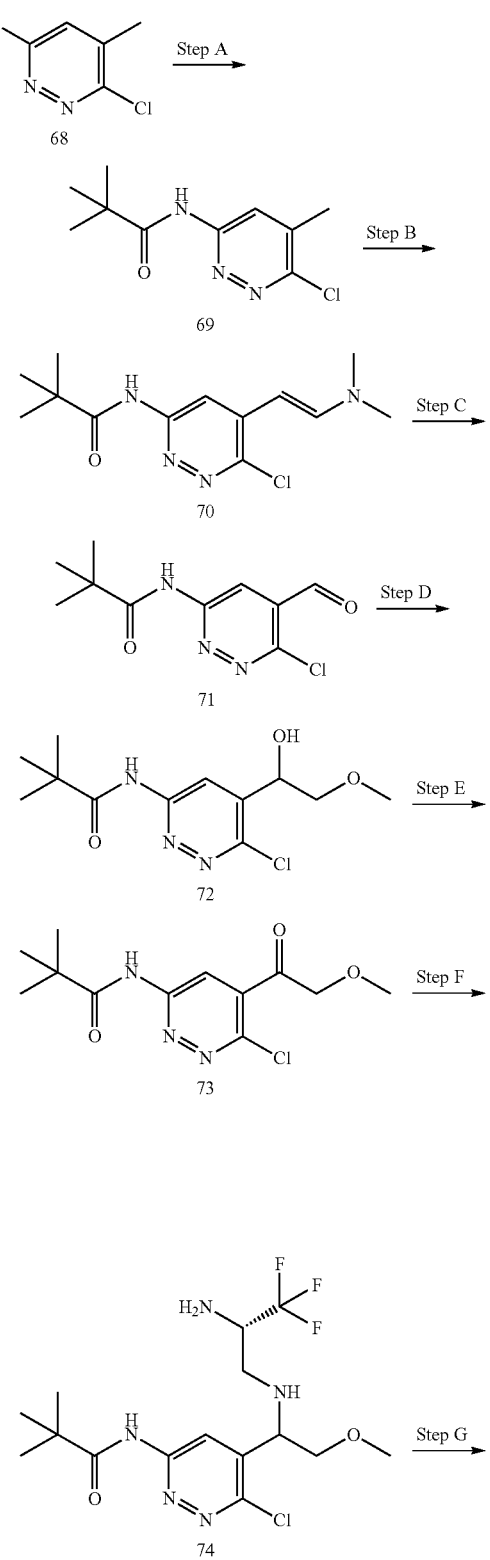

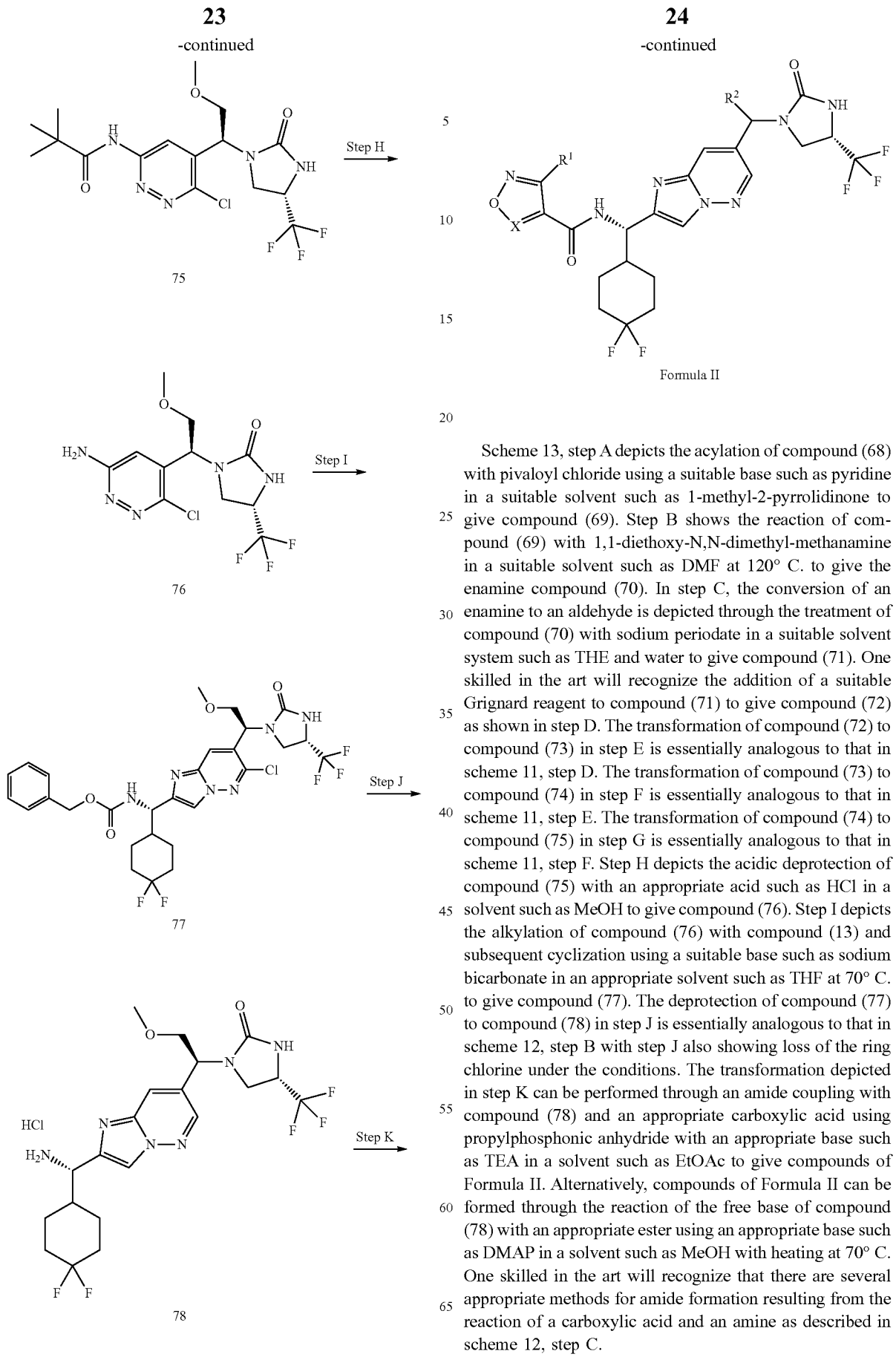

Scheme 13, step A depicts the acylation of compound (68) with pivaloyl chloride using a suitable base such as pyridine in a suitable solvent such as 1-methyl-2-pyrrolidinone to give compound (69). Step B shows the reaction of compound (69) with 1,1-diethoxy-N,N-dimethyl-methanamine in a suitable solvent such as DMF at 120° C. to give the enamine compound (70). In step C, the conversion of an enamine to an aldehyde is depicted through the treatment of compound (70) with sodium periodate in a suitable solvent system such as THF and water to give compound (71). One skilled in the art will recognize the addition of a suitable Grignard reagent to compound (71) to give compound (72) as shown in step D. The transformation of compound (72) to compound (73) in step E is essentially analogous to that in scheme 11, step D. The transformation of compound (73) to compound (74) in step F is essentially analogous to that in scheme 11, step E. The transformation of compound (74) to compound (75) in step G is essentially analogous to that in scheme 11, step F. Step H depicts the acidic deprotection of compound (75) with an appropriate acid such as HCl in a solvent such as MeOH to give compound (76). Step I depicts the alkylation of compound (76) with compound (13) and subsequent cyclization using a suitable base such as sodium bicarbonate in an appropriate solvent such as THF at 70° C. to give compound (77). The deprotection of compound (77) to compound (78) in step J is essentially analogous to that in scheme 12, step B with step J also showing loss of the ring chlorine under the conditions. The transformation depicted in step K can be performed through an amide coupling with compound (78) and an appropriate carboxylic acid using propylphosphonic anhydride with an appropriate base such as TEA in a solvent such as EtOAc to give compounds of Formula II. Alternatively, compounds of Formula II can be formed through the reaction of the free base of compound (78) with an appropriate ester using an appropriate base such as DMAP in a solvent such as MeOH with heating at 70° C. One skilled in the art will recognize that there are several appropriate methods for amide formation resulting from the reaction of a carboxylic acid and an amine as described in scheme 12, step C.

Scheme 14

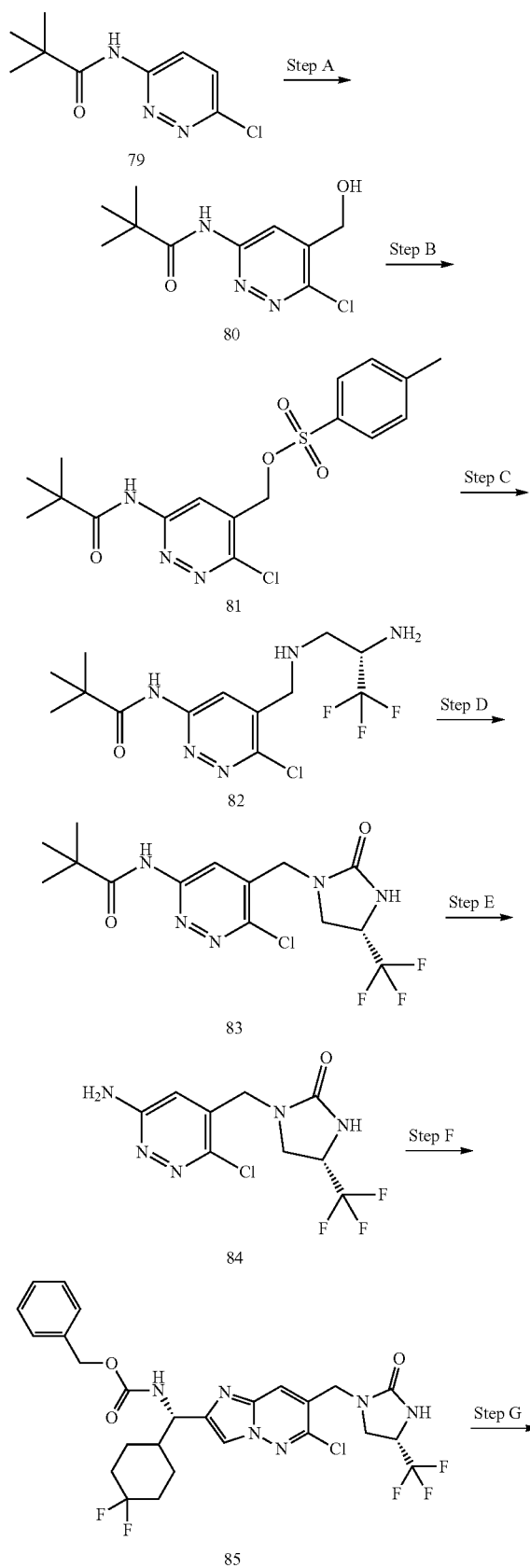

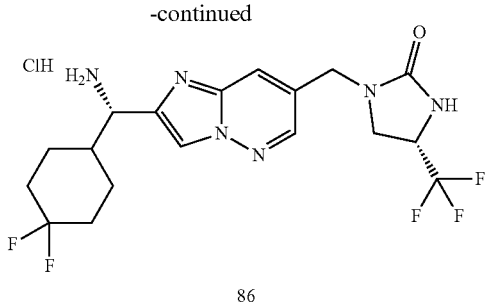

Scheme 14, step A depicts a Minisci hydroxymethylation of compound (79) using methanol and ammonium persulfate to give compound (80). Step B shows the tosylation of compound (80) using p-toluenesulfonic anhydride and appropriate bases such as TEA and DMAP in a suitable solvent such as acetonitrile to give compound (81). Step C depicts the displacement of the tosylate on compound (81) with (2S)-3,3,3-trifluoropropane-1,2-diamine using an appropriate base such as $K_3PO_4$ in an appropriate solvent such as DMSO to give compound (82). The cyclization of compound (82) with CDI in a solvent such as DMSO to give compound (83) is depicted in step D. One skilled in the art will recognize the acidic deprotection of compound (83) shown in step E with an appropriate acid such as concentrated HCl in a solvent such as MeOH to give compound (84). The transformation of compound (84) to compound (85) in step F is essentially analogous to that in scheme 13, step I. The transformation of compound (85) to compound (86) in step G is essentially analogous to that in scheme 13, step J.

Scheme 15

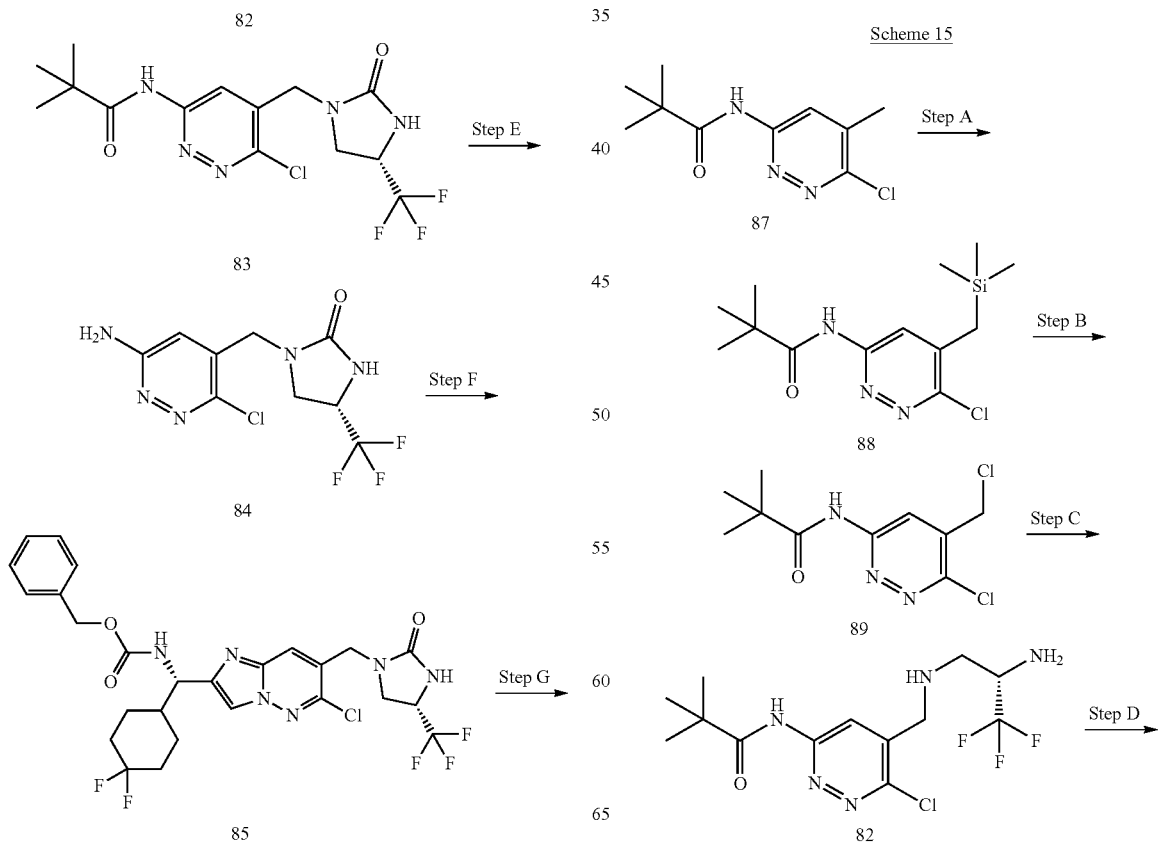

-continued

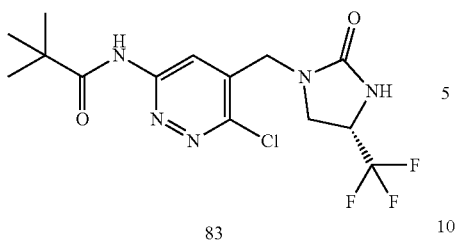

83

Scheme 15, step A depicts the trimethylsilylation of compound (87) using an appropriate base such as n-butyllithium in an appropriate solvent system such as THF and hexane followed by addition of chlorotrimethylsilane to give compound (88). Step B shows the chlorination of compound (88) with an appropriate reagent such as NCS in a solvent such as DMF to give compound (89). Step C depicts the displacement of the alkylchlorine on compound (89) with (2S)-3,3,3-trifluoropropane-1,2-diamine using sodium iodide and an appropriate base such as DIEA in an appropriate solvent such as acetonitrile to give compound (82). The transformation of compound (82) to compound (83) in step D is essentially analogous to that in scheme 11, step F.

Preparation 1

Methyl-2-(benzyloxycarbonylamino)-2-(4,4-difluorocyclohexylidene)acetate

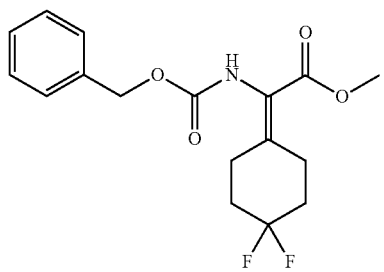 [SMILES: COC(=O)C(NC(=O)OCc1ccccc1)=C1CCC(F)(F)CC1]

Scheme 1, step A: The following reaction is repeated five times: Methyl 2-(benzyloxycarbonylamino)-2-dimethoxyphosphoryl-acetate (882 g, 2.66 mol) is added to a flask containing NMP (1.7 L) at 15° C. DBU (367 g, 2.41 mol) is added dropwise with stirring while maintaining the temperature near 15° C. then held at the same temperature for 30 minutes. 4,4-Difluorocyclohexanone (340 g, 2.53 mmol) is dissolved in NMP (680 mL) and the enolate solution is added in a thick stream, while keeping the temperature below 20° C. The solution is stirred at 10-20° C. for 12 hours. The crude reaction mixtures from the five reactions are combined, added to water (18 L) at 10-15° C., and filtered under vacuum. The filter cake is washed with petroleum ether (15 L) and dried to give a white solid. The solid is dissolved in 1,4-dioxane (8 L) at 15-20° C. and water (8 L) is added. The resulting suspension is filtered, washed with petroleum ether (15 L), and dried in air to give the title compound as a white solid (3.90 kg, 90%). ES/MS (m/z): 340 (M+H).

Preparation 2

2-(Benzyloxycarbonylamino)-2-(4,4-difluorocyclohexylidene)acetic acid

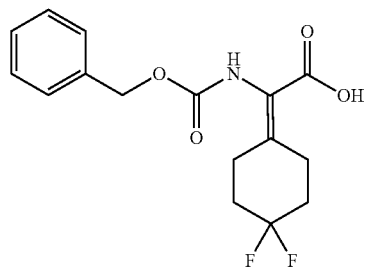 [SMILES: O=C(NC(C(=O)O)=C1CCC(F)(F)CC1)OCc1ccccc1]

Scheme 1, step B: The following procedure is repeated five times: Methyl 2-(benzyloxycarbonylamino)-2-(4,4-difluorocyclohexylidene)acetate (500 g, 1.47 mol) is added to a flask containing THF (1.5 L) at 15° C. under nitrogen and is stirred until dissolved. 1.5 M aqueous NaOH (1.47 L) is added dropwise keeping the reaction mixture below 18° C. After full addition, the reaction mixture is heated to 25° C. with stirring for 12 hours. The five crude reaction mixtures are combined and concentrated in vacuo to remove most of the THF. The resulting solution is washed with MTBE (1×5 L, 1×2.5 L). The aqueous phase is adjusted to pH ~1 with 5 N $H_2SO_4$ and stirred at 15° C. for 10 minutes. The resulting mixture is extracted with EtOAc (1×5 L, 1×3 L, 1×2 L). The combined organic extracts are washed with saturated aqueous sodium chloride (1×4 L, 1×2 L), dried over anhydrous sodium sulfate, filtered, and concentrated in vacuo to give a white solid. The solid is suspended in petroleum ether (8 L), filtered, and dried in air to give the title compound as a white solid (2.0 kg, 84%). $^{19}F$ NMR (DMSO-d6), δ 95.67.

Preparation 3

(2S)-2-(Benzyloxycarbonylamino)-2-(4,4-difluorocyclohexyl)acetic acid

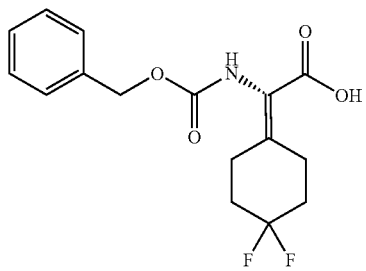

Scheme 1, step C: The following procedure is repeated two times: 2-(Benzyloxycarbonylamino)-2-(4,4-difluorocyclohexylidene)acetic acid (350 g, 1.08 mol) is added to a 5 L autoclave containing MeOH (1.4 L) at 15-20° C. and the solution is saturated with nitrogen for 1 hour. In a glovebox, Rh-COD-[(S)-MaxPhos]-BF4 (6.8 g, 10.76 mmol) is added to the reaction mixture which is then purged with hydrogen three times. The reaction mixture is stirred at 30° C. under hydrogen (100 psi) for 22 hours. The crude reaction mixtures are combined and concentrated in vacuo to give a yellow solid. The solid is suspended in water (6 L) and 2 N NaOH is added dropwise until the pH reaches ~13 and the mixture is homogeneous. The solution is washed with MTBE (1×3 L, 1×2 L). The pH of the aqueous solution is adjusted to ~1 with 5 N HCl and stirred for 10 minutes at 15° C. The solution is extracted with EtOAc (1×4 L, 1×3 L, 1×2 L). The organic extracts are combined and washed with saturated aqueous sodium chloride (1×2 L, 1×1 L), dried over sodium sulfate, filtered, and concentrated in vacuo to give the title compound contaminated with rhodium as a white solid (630 g, 90%). This semi-pure material is combined with additional compound from separate runs of the same reaction to further purify.

The following procedure is repeated four times: (2S)-2-(Benzyloxycarbonylamino)-2-(4,4-difluorocyclohexyl)acetic acid (266 g, 813 mmol) is added to EtOAc (2.66 L) then polymercaptal multi-branched alkyl polysulfide propyl silica (62.5 g) is added at 15-20° C. under nitrogen. The mixture is heated to 25° C. for 15 hours under nitrogen. The reactions are combined, filtered through diatomaceous earth, and concentrated in vacuo to give the title compound as a white solid (1040 g, 97%, 98% ee) contaminated with 871 ppm rhodium. ES/MS (m/z): 350 (M+Na). Chiral SFC method for ee determination: Chiralpak AD-3, 3 μM, 0.46 cm ID×15 cm L, mobile phase A=$CO_2$, mobile phase B=2-propanol, gradient elution 10-40% B in A over 6 minutes @ 2.5 mL/min, 220 nM detection wavelength. Major enantiomer elutes at 2.59 min, minor enantiomer elutes at 2.97 min: 98% ee. Rhodium quantitation by digesting 100 mg sample in 5 mL concentrated nitric acid. Solution is diluted 1000 times and analyzed via ICP-MS: 871 ppm rhodium.

Preparation 4 tert-Butyl (4S)-4-(benzyloxycarbonylamino)-4-(4,4-difluorocyclohexyl)-3-oxo-butanoate

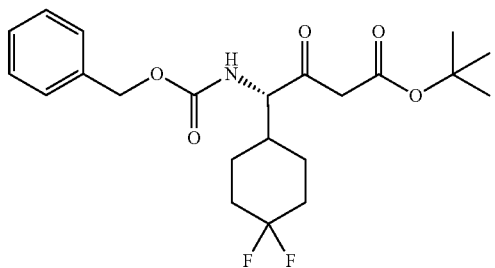 [SMILES: CC(C)(C)OC(=O)CC(=O)[C@@H](NC(=O)OCc1ccccc1)C1CCC(F)(F)CC1]

Scheme 1, step D: To a round bottom flask under an atmosphere of nitrogen is added (2S)-2-(benzyloxycarbonylamino)-2-(4,4-difluorocyclohexyl)acetic acid (15 g, 48 mmol), THF (400 mL), and CDI (7.8 g, 48 mmol). The solution is stirred at room temperature for 1.5 hours then cooled to −78° C. In a separate round bottom flask under an atmosphere of nitrogen is added THF (150 mL) and DIEA (29 mL, 206 mmol). The solution is cooled to 0° C. and a solution of 2.5 M n-butyllithium in hexanes (82 mL, 210 mmol) is added dropwise. After 10 minutes, the solution is cooled to −78° C. and tert-butylacetate (27.8 mL, 206 mmol) is added dropwise. After an additional hour, the enolate solution is added via cannula to the above solution. After 1 hour, the reaction is quenched at −78° C. with 300 mL of saturated aqueous ammonium chloride solution. The reaction is removed from the cold bath, diluted with 1 L of water, and the solvent volume is reduced by 300-400 mL under reduced pressure. The mixture is extracted with EtOAc (3×100 mL). The organic layers are combined and washed with 1 N HCl (2×100 mL), water (100 mL), and saturated aqueous sodium chloride (100 mL), dried over sodium sulfate, filtered, and concentrated in vacuo. The residue is purified by flash chromatography, eluting with hexane and EtOAc to give the title compound (19.5 g, 95%). ES/MS (m/z): 424 (M−H).

Preparation 5

Benzyl N-[(1S)-3-bromo-1-(4,4-difluorocyclohexyl)-2-oxo-propyl]carbamate

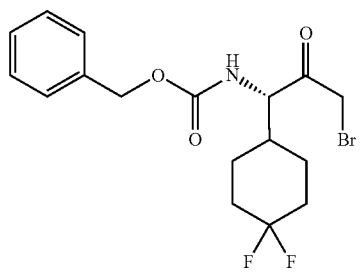 [SMILES: O=C(N[C@H](C(=O)CBr)C1CCC(F)(F)CC1)OCc1ccccc1]

Scheme 1, step E: To a solution of tert-butyl (4S)-4-(benzyloxycarbonylamino)-4-(4,4-difluorocyclohexyl)-3-oxo-butanoate (19.5 g, 45.8 mmol) and 2,6-dimethylpyridine (0.4 mL, 3.44 mmol) in MeOH (80 mL) is added NBS (8.0 g, 44.5 mmol). The reaction is stirred at room temperature for 2.5 hours and stored at −20° C. for an additional 24 hours. The reaction is diluted with EtOAc (600 ml) then washed with a 50% solution of saturated sodium chloride in water (3×100 mL) and saturated aqueous sodium chloride (3×100 mL). The organic phase is dried over sodium sulfate, filtered, and concentrated in vacuo to give the crude intermediate bromide which is then dissolved in toluene (230 mL). TFA (25 mL) is added to the solution which is then heated to 80° C. After 2 hours at 80° C., the heat is removed and the solvent removed in vacuo. The residue is purified by silica gel flash chromatography eluting with toluene and EtOAc to give the title compound (10.3 g, 56%). ES/MS m/z ($^{79}Br/^{81}Br$) 404/406 $[M+H]^+$, $[\alpha]_D^{20}$=+22.5° (C=1.0, $CH_2Cl_2$).

Preparation 6

2-Phenyl-4-(2,2,2-trifluoroacetyl)-4H-oxazol-5-one

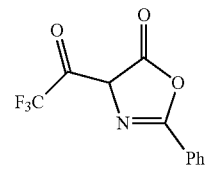 [SMILES: O=C1OC(c2ccccc2)=NC1C(=O)C(F)(F)F]

Scheme 2, step A: 2-Benzamidoacetic acid (200 g, 1.116 mol) and acetone (1 L) are added to a 4 L jacketed reactor to give a slurry. The reactor is cooled to 3° C. and trifluoroacetic anhydride (500 mL, 3.56 mol) is added dropwise for the first 25 mL then as a slow stream, ensuring the reaction temperature never exceeds 5° C. The reaction mixture is stirred overnight at 0° C. for 23 hours. The reaction is quenched at 0° C. by slow addition of water (2 L) with the first 150 mL added over 30 minutes and the remainder over an additional 40 minutes. The mixture is stirred for 10 minutes, filtered, rinsed with water (1 L), and placed on a nitrogen press for 20 hours to give the title compound as a purple solid (287 g, 88%). ES/MS (m/z): 258 (M+H).

Preparation 7

N-(3,3,3-Trifluoro-2,2-dihydroxy-propyl)benzamide

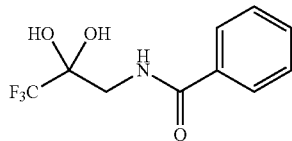 [SMILES: O=C(NCC(O)(O)C(F)(F)F)c1ccccc1]

Scheme 2, step B: 2-Phenyl-4-(2,2,2-trifluoroacetyl)-4H-oxazol-5-one (252 g, 980 mmol) is added to a 4 L flask equipped with an overhead stirrer and slurried in THF (1.6 L). Water is added over 15 minutes, keeping the reaction temperature below 28° C., and is then stirred at ambient temperature for 24 hours. Water (0.5 L) is added and the pH is adjusted to 7.5 with 5 N NaOH. MTBE (500 mL), saturated aqueous sodium bicarbonate solution (0.5 L), and saturated aqueous sodium chloride (200 mL) are added and the organic layer is separated. The organic layer is washed with saturated aqueous sodium chloride (200 mL), dried over anhydrous sodium sulfate, and filtered. The filtrate is partially concentrated in vacuo until solids begin to precipitate. Heptanes (0.8 L) are added then concentrated in vacuo until 500 mL of solution remains. The resulting solid is filtered, rinsed with heptanes (300 mL), and placed on a nitrogen press for 1 hour to give the title compound as a yellow-orange solid (203.7 g, 83%). ES/MS (m/z): 250 (M+H).

Preparation 8

N—[(Z)-3,3,3-Trifluoro-2-[[(1S)-1-phenylethyl]amino]prop-1-enyl]benzamide

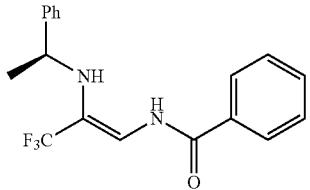 [SMILES: C[C@H](N/C(=C\NC(=O)c1ccccc1)C(F)(F)F)c1ccccc1]

Scheme 2, step C: N-(3,3,3-Trifluoro-2,2-dihydroxy-propyl)benzamide (203 g, 814.6 mmol) is added under nitrogen to a 4 L flask with overhead stirring and equipped with a Dean-Stark trap. Toluene (2 L) is added to create a slurry then (1S)-1-phenylethanamine (120 mL, 930 mmol) is added. The reaction mixture is heated to 105° C. with stirring for 7.5 hours then cooled to 22° C. for 16 hours. After this time, the reaction is concentrated in vacuo. The residue is purified on silica gel [pre-washed with 20% MTBE in heptanes (1 L)] eluting with 20% MTBE in heptanes (6 L). The eluent is concentrated to give crude product (204 g) which is then dissolved in EtOH (1 L) followed by dropwise addition of water (410 mL) until the solution is cloudy. Seed crystals (200 mg) are added followed by dropwise addition of water (290 mL). This cloudy solution is cooled to 10° C., water (50 mL) is added dropwise, and then the solution is cooled to 5° C. for 10 minutes to further crystallize the product. The resulting solid is filtered and rinsed with 10% EtOH in water (500 mL) then water (50 mL). The solid is dried overnight on a nitrogen press to give the title compound as an orange solid (172 g, 63%). ES/MS (m/z): 335 (M+H).

Preparation 9

N-[(2S)-3,3,3-Trifluoro-2-[[(1S)-1-phenylethyl]amino]propyl]benzamide

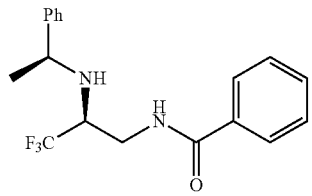 [SMILES: C[C@H](N[C@@H](CNC(=O)c1ccccc1)C(F)(F)F)c1ccccc1]

Scheme 2, step D: The following procedure is repeated four times: N—[(Z)-3,3,3-Trifluoro-2-[[(1S)-1-phenylethyl]amino]prop-1-enyl]benzamide (43 g, 128.6 mmol), Rh-COD-[(R)-MaxPhos]-BF4 (700-2000 mg, 1.25-3.57 mmol), and t-amyl alcohol (400 mL) are added to a 600 mL overhead stirred autoclave in a glove box. The reaction vessel is then sealed and removed from the glovebox. The vessel is charged with hydrogen (150 psi) and vented three times before it is charged with hydrogen (150 psi) and stirred at 20-30° C. for 20-31 hours. The vessel is moved to a glovebox, vented, and additional Rh-COD-[(R)-MaxPhos]-BF4 (0-1000 mg, 0-1.78 mmol) is added. The vessel is sealed, removed from the glovebox, charged with hydrogen (150 psi), and vented three times. The vessel is again charged with hydrogen (150 psi) and stirred at 30° C. for 0-43 hours. The reaction vessel is vented and the crude reaction is transferred to a flask, rinsing down with MeOH (100 mL). The crude reaction mixtures are combined and concentrated in vacuo. The resulting residue is purified via silica gel eluting with 35% EtOAc in heptanes (6 L) to give semi pure material (94.5:5.5 ratio of diastereomers by $^1$H NMR). The material is dissolved in heptanes (1.5 L), heated to 80° C. over 20 minutes, then cooled to 22° C. for one hour. The resulting solids are filtered to give 144 g of compound. The filtrate is combined with the impure, product containing fractions from the column and concentrated in vacuo to give 25 g of crude product. All product lots are combined, slurried in heptane (1.5 L), and heated to 80° C. over 2 hours. The heat is held at 80° C. for 30 minutes then cooled to 25° C. slowly over 14 hours at 4° C./hour. The resulting slurry is filtered to give the title compound (133 g, 77%) as a 98:2 ratio of diastereomers by $^{19}$F NMR. ES/MS (m/z): 337 (M+H). $^{19}$F NMR (DMSO-d6) δ 73.1 (major diastereomer), 73.6 (minor diastereomer).

Preparation 10

(2S)-3,3,3-Trifluoropropane-1,2-diamine dihydrochloride

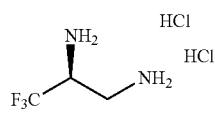

Scheme 2, step E: N-[(2S)-3,3,3-trifluoro-2-[[(1S)-1-phenylethyl]amino]propyl]benzamide (110 g, 327 mmol), 1,4-dioxane (200 mL), and water (500 mL) are added to a 2 L flask. Concentrated HCl (12 M, 250 mL) is slowly added and the reaction mixture is heated to 95° C. for 72 hours. After this time, the reaction mixture is cooled to 22° C. and washed with toluene (2×400 mL). The aqueous solution is azeotropically distilled with n-butyl alcohol (3×600 mL) via rotary evaporator. The remaining clear yellow mother liquor containing crystalline solids is diluted with IPA (750 mL) and cooled at 10° C. overnight. The resulting solids are filtered, rinsed with IPA (400 mL), and dried in a 50° C. vacuum oven for one hour to give the title compound as a white solid (63.5 g, 96.6%). ES/MS (m/z): 129 (M+H–2HCl).

Preparation 11

(1E)-2,2-Difluoropropanal oxime

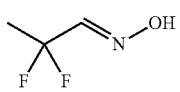

Scheme 3, step A: Dess-Martin periodinane (11.6 g, 27.3 mmol) is added to 2,2-difluoropropan-1-ol (2.5 g, 26.0 mmol) in DCM (130 mL) and stirred vigorously at 22° C. for 30 minutes. Hydroxylamine hydrochloride (5.42 g, 78.1 mmol) and sodium bicarbonate (10.9 g, 130 mmol) are added and the reaction mixture is stirred vigourously at 22° C. for 2.5 hours. The reaction mixture is quenched with a solution of sodium thiosulfate (12 g, 76 mmol) in water (50 mL) and stirred vigorously for 5 minutes. The reaction mixture is then diluted with diethyl ether (200 mL) and washed with saturated aqueous sodium bicarbonate solution (3×30 mL) and saturated aqueous sodium chloride (30 mL). The organics are dried over anhydrous magnesium sulfate, filtered, and concentrated in vacuo to give the title compound as a light yellow oil (3.30 g, 77%). $^1$H NMR (CDCl$_3$) δ 7.57 (s, 1H), 7.55 (t, 1H, J=4.1 Hz), 1.82 (t, 3H, J=18.5 Hz).

Preparation 12

Ethyl 3-(1,1-difluoroethyl)isoxazole-4-carboxylate

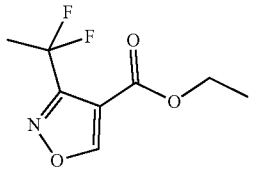

Scheme 3, step B: (1E)-2,2-Difluoropropanal oxime (3.3 g, 67 mass %, 20.0 mmol) is dissolved in chloroform (40 mL). The solution is cooled to 0° C. and NBS (3.55 g, 20.0 mmol) is added and the solution is allowed to warm to 22° C. for 15 hours. Ethyl (E)-3-(dimethylamino)prop-2-enoate (3.27 mL, 22 mmol) is then added to the reaction mixture followed by TEA (4.18 mL, 30 mmol) dropwise at 22° C. The reaction mixture is stirred at 22° C. for five hours then concentrated in vacuo. The residue is purified by silica gel flash chromatography eluting with hexanes and EtOAc to give the title compound as a colorless oil (2.21 g, 45%). $^1$H NMR (CDCl$_3$) δ 8.99 (s, 1H), 4.38 (q, 2H, J=7.1 Hz), 2.17 (t, 3H, J=18.9 Hz), 1.39 (t, 3H, J=7.1 Hz).

Preparation 13

Ethyl 3-(fluoromethyl)isoxazole-4-carboxylate

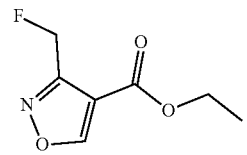

Scheme 3, steps A-B: Dess-Martin periodinane (11.0 g, 25.9 mmol) is added to a solution of 2-fluoroethanol (1.5 g, 23 mmol) in DCM (100 mL), and stirred at ambient temperature for 30 minutes. After this time, sodium bicarbonate (12.2 g, 145 mmol) and hydroxylamine hydrochloride (4.7 g, 68 mmol) are added, and the reaction is stirred overnight. The resulting solution is filtered through diatomaceous earth, rinsing through with approximately 20 mL DCM. The resulting solution is used as is assuming 100% conversion to intermediate oxime.

To the resulting mixture is added 4 drops of pyridine followed by NCS (2.9 g, 22 mmol). The mixture is stirred for 6 hours at ambient temperature, then heated at 40° C. for 75 minutes longer. The reaction mixture is cooled back to ambient temperature, then treated with ethyl 3-(dimethylamino)prop-2-enoate (5.0 mL, 34 mmol) followed by a single portion of TEA (5.0 mL, 36 mmol). The resulting mixture is stirred for 45 minutes, then concentrated in vacuo and purified by silica gel flash chromatography eluting with MTBE and hexanes to give the title compound as a colorless, volatile oil (694 mg, 17% yield). $^1$H NMR (CDCl$_3$) δ 8.95 (s, 1H), 5.70 (d, 2H, J=46 Hz), 4.38 (q, 2H, J=7.1 Hz), 1.39 (t, 3H, J=7.1 Hz).

Preparation 14

3-(1,1-Difluoroethyl)isoxazole-4-carboxylic acid

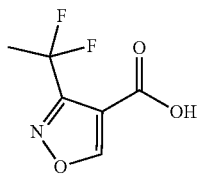

Scheme 3, step C: Ethyl 3-(1,1-difluoroethyl)isoxazole-4-carboxylate (1.00 g, 4.09 mmol) is dissolved in THF (2 mL) and MeOH (2 mL) and then cooled to 0° C. 5 N aqueous NaOH (1.3 mL, 6.55 mmol) is added and the reaction mixture is stirred for 15 minutes. The reaction mixture is diluted with water and washed with EtOAc. The aqueous layer is acidified with 5 N aqueous HCl (1.3 mL) and extracted with EtOAc (50 mL). The organic layer is dried over magnesium sulfate, filtered, and concentrated in vacuo to give a colorless oil. The oil is suspended in water (5 mL) and sonicated to give a thick white precipitate suspended in water. The resulting suspension is frozen then lyophilized to give the title compound as a white solid (427 mg, 59%). ES/MS (m/z)=176 (M−H).

Preparation 15

3-(Fluoromethyl)isoxazole-4-carboxylic acid

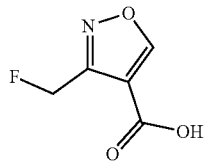

Scheme 3, step C: A solution of ethyl 3-(fluoromethyl)isoxazole-4-carboxylate (694 mg, 4.0 mmol) in MeOH (4 mL), THF (4 mL), and water (3 mL) is cooled in an ice bath. The mixture is then treated with 5 M aqueous NaOH (0.96 mL, 4.8 mmol). After 10 minutes, the reaction is allowed to stir at ambient temperature for 30 minutes, whereupon it is acidified upon the addition of 1.2 mL 5 M aqueous HCl. The mixture is diluted with water, and extracted twice with EtOAc. The combined organic layers are washed with saturated aqueous sodium chloride, dried over magnesium sulfate, and concentrated in vacuo to afford the title compound as a white solid (506 mg, 87% yield). $^1$H NMR (DMSO-d$_6$) δ 13.39 (br s, 1H), 9.62 (s, 1H), 5.60 (d, 2H, J=46 Hz).

Preparation 16

2,2-Difluoroacetaldehyde oxime

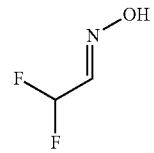

Scheme 4, steps A and B: To an oven dried 1 L flask is added ethyl 2,2-difluoroacetate (25.4 mL, 242 mmol) and diethyl ether (40 mL), and the mixture is cooled to −78° C. To the mixture is added lithium aluminum hydride (1 M solution in THF, 61.0 mL, 61.0 mmol) dropwise via addition funnel over a period of 25 minutes. The addition funnel is further washed with diethyl ether (5 mL) and added dropwise. After 2 hours and 45 minutes, the reaction is quenched with the slow addition of EtOH (6 mL), and is allowed to stir at room temperature for 20 minutes. The mixture is then poured into a mixture of concentrated sulfuric acid (15 mL) in crushed ice (200 mL). After stirring for 5 minutes, the mixture is diluted with diethyl ether (150 mL), poured into a separatory funnel, and the layers are separated. The aqueous layer is extracted once more with diethyl ether (200 mL), and the combined organics are dried over magnesium sulfate, filtered, and concentrated in vacuo to give the intermediate 1-ethoxy-2,2-difluroethanol in a volume of 45 mL with assumed quantitative yield.

In a separate 500 mL round bottom flask, hydroxylamine hydrochloride (19.32 g, 278.0 mmol) and sodium bicarbonate (23.4 g, 279 mmol) are dissolved in water (60 mL) and cooled in an ice water bath. To the rapidly stirred solution is added the aforementioned solution of 1-ethoxy-2,2-difluroethanol (242 mmol) in a steady stream via syringe. The mixture is allowed to stir at room temperature for 1 hour 50 minutes, at which point the aqueous solution is extracted with diethyl ether (2×50 mL), and the combined organics are dried over magnesium sulfate and filtered. The majority of volatiles are then removed by short path distillation at atmospheric pressure to give the title compound as a liquid that is contaminated with THF and ethanol (12.5:1 mixture of E/Z isomers, 17.35 g, approximated at 40 mass % based on residual solvents, 30%). $^1$H NMR (CDCl$_3$) Major isomer δ 8.52 (s, 1H), 7.50 (m, 1H), 6.16 (dt, J=54.1 Hz, 6.4 Hz, 1H). Minor isomer δ 8.68 (s, 1H), 6.94 (m, 1H), 6.75 (dt, J=53.8 Hz, 5.3 Hz, 1H).

Preparation 17

Ethyl 3-(difluoromethyl)isoxazole-4-carboxylate

Scheme 4, step C: The title compound is prepared from 2,2-difluoroacetaldehyde oxime in a manner essentially analogous to the method of Preparation 12 (3.375 g, 32%). $^1$H NMR (CDCl$_3$) δ 9.01 (s, 1H), 7.08 (t, J=52.7 Hz, 1H), 4.40 (q, J=7.2 Hz, 2H), 1.40 (t, J=7.2 Hz, 3H).

Preparation 18

3-(Difluoromethyl)isoxazole-4-carboxylic acid

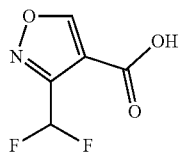

Scheme 4, steps D and E: A solution of ethyl 3-difluoromethyl)isoxazole-4-carboxylate (1.98 g, 10.4 mmol) in diethyl ether (50 mL) is cooled in an ice water bath. To the mixture is added diisobutylaluminum hydride (1.0 M solution in hexane, 22.8 mL, 22.8 mmol). After 45 minutes, additional diisobutylaluminum hydride (1.0 M solution in hexane, 1.0 mL, 1.0 mmol) is added. The mixture is stirred a further 15 minutes and is then quenched with 1 M aqueous HCl. The resulting mixture is stirred for approximately 15 minutes and is then transferred to a separatory funnel and extracted three times with diethyl ether. The combined organic layers are washed twice with saturated aqueous sodium chloride, dried over magnesium sulfate, filtered, and concentrated in vacuo.

The resulting crude [3-(difluoromethyl)isoxazol-4-yl]methanol (assumed 10.4 mmol) is dissolved in acetone (18 mL) and cooled in an ice water bath. To the solution is added a solution of chromium trioxide (1.53 g, 15.3 mmol) in a mixture of concentrated sulfuric acid (1.4 mL) and water (4.2 mL) dropwise. The resulting solution is stirred rapidly at room temperature for 4 hours and 40 minutes. At this time, water is added and the mixture is extracted three times with EtOAc. The combined organic layers are washed twice with saturated aqueous sodium chloride, dried over magnesium sulfate, filtered, and concentrated in vacuo to give sufficiently pure title compound as a low melting white solid (1.426 g, 83%). $^1$H NMR (d$_6$-DMSO) δ 13.67 (br s, 1H), 9.76 (s, 1H), 7.40 (t, J=52.3 Hz, 1H).

Preparation 19

Ethyl 3-[2-[tert-butyl(dimethyl)silyl]oxyethyl]isoxazole-4-carboxylate

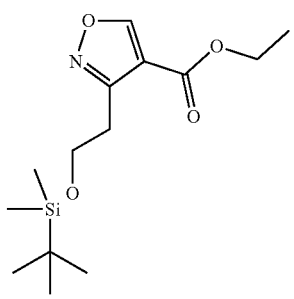

Scheme 5, steps A and B: To a solution of 3-[tert-butyl(dimethyl)silyl]oxypropan-1-ol (5.0 g, 26.3 mmol) in DCM (130 mL) is added Dess-Martin periodinane (12.33 g, 28.2 mmol). The mixture is stirred at room temperature for 35 minutes. To the reaction is then added sodium bicarbonate (11.5 g, 137 mmol) and hydroxylamine hydrochloride (5.5 g, 79 mmol). After 3.5 hours, the reaction is quenched with sodium thiosulfate (22 g) and water (100 mL). After stirring for 5 minutes, the mixture is transferred to a separatory funnel and the layers are separated. The organic layer is washed with saturated aqueous sodium bicarbonate then twice with saturated aqueous sodium chloride. The organic layer is dried over magnesium sulfate and concentrated in vacuo.

The resulting crude oxime is dissolved in chloroform (80 mL) and 4 drops of pyridine are added followed by NCS (3.35 g, 25.1 mmol). The reaction is heated at 45° C. for 1 hour, and then cooled to room temperature. To the mixture is added a solution of ethyl 3-(dimethylamino)prop-2-enoate (4.6 g, 32 mmol) in chloroform (4 mL) followed by triethylamine (5.50 mL, 39.5 mmol). After 1 hour 25 minutes, the mixture is concentrated in vacuo. The resulting residue is purified by silica gel flash chromatography eluting with hexanes and MTBE to give the title compound as a colorless oil. ES/MS (m/z): 300.0 (M+H).

Preparation 20

Ethyl 3-(2,2-difluoroethyl)isoxazole-4-carboxylate

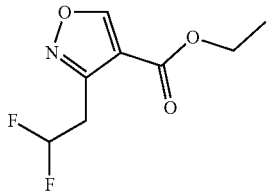

Scheme 5, steps C, D, and E: To a solution of ethyl 3-[2-[tert-butyl(dimethyl)silyl]oxyethyl]isoxazole-4-carboxylate (2.72 g, 90% purity, 8.18 mmol) in EtOH (40 mL) is added a 4 M solution of HCl in MeOH (20 mL, 80 mmol). After 15 minutes, the mixture is concentrated in vacuo, partitioned between EtOAc and saturated aqueous sodium bicarbonate. The aqueous phase is extracted once more with EtOAc and once with DCM. The combined organics are dried over magnesium sulfate and concentrated in vacuo to obtain the resulting crude alcohol.

The crude alcohol is then dissolved in DCM (60 mL) and treated with Dess-Martin periodinane (3.77 g, 8.62 mmol). The resulting mixture is stirred at ambient temperature for 35 minutes, and is quenched with sodium thiosulfate (6.0 g, 38 mmol) and 50 mL water. The mixture is extracted with DCM. The organics are dried over magnesium sulfate and concentrated in vacuo. The resulting residue is purified by silica gel flash chromatography eluting with DCM and acetone. The resulting material is dissolved in DCM (50 mL) and stirred vigorously with saturated aqueous sodium bicarbonate. The mixture is filtered through a phase separator and the organic layer is concentrated in vacuo to a pale yellow oil containing impure aldehyde product.

The crude aldehyde intermediate is dissolved in DCM (50 mL) and cooled in a dry ice/acetone bath at −25° C. DAST (2.50 mL, 18.9 mmol) is added dropwise and stirred, allowing the cooling bath to gradually warm. After 30 minutes, additional DAST (0.8 mL, 6 mmol) is added, with the bath temperature around −10° C. After stirring for an additional 40 minutes, the reaction mixture is cooled to −40° C. and carefully quenched with saturated aqueous sodium bicarbonate. The mixture is warmed to room temperature, diluted with saturated aqueous sodium bicarbonate, and extracted three times with DCM. The combined organics are washed once more with saturated aqueous sodium bicarbonate, dried over magnesium sulfate and concentrated in vacuo. The resulting residue is purified by silica gel flash chromatography eluting with hexanes and MTBE to give the title compound as a colorless oil (479 mg, 28% overall yield). $^1$H NMR (CDCl$_3$) δ 8.94 (s, 1H), 6.28 (tt, 1H, J=56.2 Hz, 4.8 Hz), 4.37 (q, 2H, J=7.2 Hz), 3.57 (td, 2H, J=15.5 Hz, 4.8 Hz), 1.40 (t, 3H, J=7.2 Hz).

Preparation 21

3-(2,2-Difluoroethyl)isoxazole-4-carboxylic acid

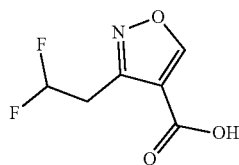 [SMILES: O=C(O)c1conc1CC(F)F]

Scheme 5, step F: The title compound is prepared from ethyl 3-(2,2-difluoroethyl)isoxazole-4-carboxylate in a manner essentially analogous to the method of Preparation 15. $^1$H NMR (DMSO-d$_6$) δ 13.40 (br s, 1H), 9.58 (s, 1H), 6.43 (tt, 1H, J=56.0 Hz, 4.5 Hz), 3.54 (td, 2H, J=16.8 Hz, 4.5 Hz).

Preparation 22

Ethyl 3-(2-fluoroethyl)isoxazole-4-carboxylate

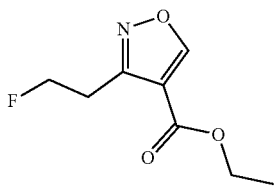

Scheme 3, steps A and B: The title compound is prepared from 3-fluoropropan-1-ol in a manner essentially analogous to the method of Preparation 13. $^1$H NMR (CDCl$_3$) δ 8.91 (s, 1H), 4.82 (dt, 2H, J=46.6 Hz, 6.3 Hz), 4.36 (q, 2H, J=7.1 Hz), 3.40 (dt, 2H, J=22.0 Hz, 6.3 Hz), 1.39 (t, 3H, J=7.1 Hz).

Preparation 23

3-(2-Fluoroethyl)isoxazole-4-carboxylic acid

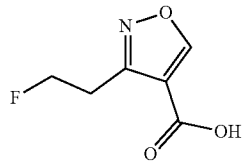 [SMILES: O=C(O)c1conc1CCF]

Scheme 3, step C: The title compound is prepared from ethyl 3-(2-fluoroethyl)isoxazole-4-carboxylate in a manner essentially analogous to the method of Preparation 15. $^1$H NMR (CDCl$_3$) δ 9.01 (s, 1H), 4.85 (dt, 2H, J=46.6 Hz, 6.3 Hz), 3.40 (dt, 2H, J=22.1 Hz, 6.3 Hz).

Preparation 24

Ethyl 3-(1-fluoro-1-methyl-ethyl)isoxazole-4-carboxylate

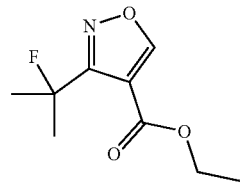

Scheme 6, steps A, B, and C: To a round bottom flask containing methyl 2-fluoro-2-methyl-propanoate (5.0 mL, 41.6 mmol) is added diethyl ether (100 mL). The flask is placed under nitrogen and cooled in a 0° C. ice bath. To the mixture is added lithium aluminum hydride (2.0 M in THF, 25 mL, 50 mmol). After 1 hour, the reaction is quenched with water (1.9 mL), followed by 5 M aqueous NaOH (1.9 mL), then water (5.7 mL), and the resulting mixture is stirred for 25 minutes. Magnesium sulfate is added to the reaction, and the mixture is filtered over diatomaceous earth and silica gel, eluting with DCM. The resulting solution is concentrated by approximately 50% and taken directly into the next step assuming quantitative yield of 2-fluoro-2-methyl-propan-1-ol (assumed 41.6 mmol).

To this solution is added Dess-Martin periodinane (18.54 g, 43.7 mmol), and the resulting mixture is stirred at room temperature for 30 minutes. To the mixture is added sodium bicarbonate (17.48 g, 208.2 mmol) and hydroxylamine hydrochloride (8.68 g, 124.9 mmol). The mixture is stirred overnight, whereupon it is quenched upon the addition of 10% aqueous sodium thiosulfate. The mixture is extracted with diethyl ether. The organic layer is washed three times with saturated aqueous sodium bicarbonate and then saturated aqueous sodium chloride. The organic layer is dried over sodium sulfate, filtered, and concentrated in vacuo to give a yellow solution of crude oxime. This is used directly in the next step assuming quantitative yield.

To a round bottom flask containing crude oxime is added chloroform (41 mL) and 20 drops of pyridine followed by NCS (5.56 g, 41.6 mmol). The resulting faint green solution is heated at 45° C. for 90 minutes. To the mixture is added a solution of ethyl 3-(dimethylamino)prop-2-enoate (7.15 mL, 49.9 mmol) in chloroform (43 mL) in a single portion. To the mixture is then added TEA (11.6 mL, 83.2 mmol) dropwise, producing an orange solution. The mixture is heated to 50° C. for 120 minutes, then allowed to stir at ambient temperature overnight. The reaction is concentrated in vacuo, and combined with a second lot of crude material (synthesized via an identical route, starting with 8.33 mmol 2-fluoro-2-methyl-propanoate). The crude material is diluted with saturated aqueous sodium bicarbonate and extracted twice with DCM. The organics are washed with saturated aqueous sodium chloride, then dried over sodium sulfate and concentrated in vacuo. The resulting residue is purified via silica gel flash chromatography eluting with hexanes and MTBE to give the title compound as a colorless oil (1.27 g, 13% overall yield). ES/MS (m/z): 202.0 (M+H).

Preparation 25

3-(1-Fluoro-1-methyl-ethyl)isoxazole-4-carboxylic acid

Scheme 6, step D: The title compound is prepared from ethyl 3-(1-fluoro-1-methyl-ethyl)isoxazole-4-carboxylate in a manner essentially analogous to the method of Preparation 15. $^1$H NMR (DMSO-d$_6$) δ 13.9 (br s, 1H), 9.57 (s, 1H), 1.80 (d, 6H, J=22 Hz).

Preparation 26

(2-Cyclopropyl-2-oxo-ethyl) benzoate

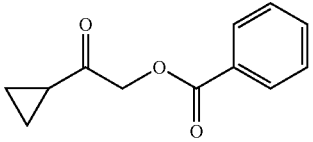 [SMILES: O=C(OCC(=O)C1CC1)c1ccccc1]

Scheme 7, step A: To a mixture of benzoic acid (32.3 g, 262 mmol) and potassium carbonate (74 g, 524.7 mmol) in DMF (500 mL) is added 2-bromo-1-cyclopropylethanone (45 g, 262.2 mmol) dropwise. The resulting mixture is stirred at ambient temperature for 20 hours, and is then diluted with water. The mixture is extracted with diethyl ether (5×200 mL), then the combined organic layers are washed three times with water, dried over magnesium sulfate, and concentrated in vacuo. The crude residue is diluted with diethyl ether (20 mL) and is precipitated with 600 mL hexanes, filtered, rinsed further with hexanes, and dried. The resulting filtrate is again concentrated in vacuo, triturated with hexanes, and filtered. The obtained solids are combined to give the title compound as an off white solid (43.6 g, 81% yield). $^1$H NMR (CDCl$_3$) δ 8.13 (m, 2H), 7.61 (m, 1H), 7.50 (m, 2H), 5.08 (s, 2H), 2.07 (m, 1H), 1.20 (m, 2H), 1.02 (m, 2H).

Preparation 27

(2-Cyclopropyl-2,2-difluoro-ethyl) benzoate

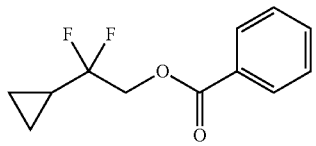 [SMILES: O=C(OCC(F)(F)C1CC1)c1ccccc1]

Scheme 7, step B: To a solution of (2-cyclopropyl-2-oxo-ethyl) benzoate (43 g, 210.6 mmol) in DCE (250 mL) is added DAST (104 g, 611 mmol). The resulting mixture is purged with nitrogen and heated to 75° C. After 18 hours, the reaction is cooled to ambient temperature, then cooled in an ice water bath for 10 minutes. The mixture is then slowly poured into 500 mL saturated aqueous sodium bicarbonate at 0° C. with stirring. Additional saturated aqueous sodium bicarbonate (200 mL) is added. The layers are separated and the aqueous phase is extracted three times with DCM. The combined organic layers are washed three times with saturated aqueous sodium bicarbonate, once with 1 N aqueous HCl, again with saturated aqueous sodium bicarbonate, and finally washed with saturated aqueous sodium chloride, dried over magnesium sulfate, and concentrated in vacuo. The crude material is purified by silica gel flash chromatography eluting with DCM and hexanes to give the title compound as an orange liquid (7.3 g, 16% yield). $^1$H NMR (CDCl$_3$) δ 8.12 (m, 2H), 7.61 (m, 1H), 7.50 (m, 2H), 4.60 (t, 2H, J=12.2 Hz), 1.38 (m, 1H), 0.77 (m, 2H), 0.68 (m, 2H).

Preparation 28

Ethyl 3-[cyclopropyl(difluoro)methyl]isoxazole-4-carboxylate

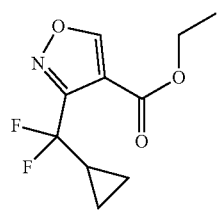 [SMILES: CCOC(=O)c1conc1C(F)(F)C1CC1]

Scheme 7, steps C, D, and E: To a solution of (2-Cyclopropyl-2,2-difluoro-ethyl) benzoate (7.5 g, 33 mmol) in MeOH (20 mL) is added 5 N aqueous NaOH (13 mL, 65 mmol). The mixture is stirred at ambient temperature for 15 minutes, at which point it is diluted with water and extracted three times with diethyl ether. The combined organic layer is washed with saturated aqueous sodium chloride, dried over magnesium sulfate and concentrated in vacuo at 0° C. to afford crude 2-cyclopropyl-2,2-difluoro-ethanol as a light orange liquid.

The resulting crude liquid is dissolved in DCM (100 mL) and Dess-Martin periodinane (14.3 g, 32.7 mmol) is added portionwise. The mixture is stirred under nitrogen at ambient temperature for 1 hour. To the mixture is added sodium bicarbonate (15.8 g, 186 mmol) followed by hydroxylamine hydrochloride (6 g, 82.9 mmol) and water (20 mL). The reaction is stirred for a further 50 minutes, diluted with water, and washed twice with saturated sodium thiosulfate. The organic layer is washed sequentially with saturated aqueous sodium bicarbonate and saturated aqueous sodium chloride, dried over magnesium sulfate, and concentrated in vacuo at 0° C. to give crude 2-cyclopropyl-2,2-difluoroacetaldehyde oxime as a light orange liquid (3.1 g, assumed 88% yield based on mass recovery) The resulting material is dissolved in DMF (100 mL), and to the mixture is added NCS (3.2 g, 23 mmol). The mixture is placed under nitrogen and heated at 50° C. for 1.5 hr, then stirred at ambient temperature overnight. The mixture is then diluted with diethyl ether and washed with 10% aqueous LiCl. The layers are separated and the aqueous layer is extracted twice more with diethyl ether. The combined organic layers are washed three times with 10% aqueous LiCl, once with saturated aqueous sodium chloride, dried over magnesium sulfate, and concentrated in vacuo to give crude 2-cyclopropyl-2,2-difluoro-N-hydroxy-acetimidoyl chloride. EtOAc (200 mL) is added and to the mixture is added ethyl 3-(N,N-dimethylamino)acrylate (2.8 mL, 19 mmol) followed by sodium bicarbonate (2.8 g, 33 mmol) with rapid stirring. The mixture is stirred at room temperature under nitrogen for 3 hours. The mixture is then washed twice with 1 N aqueous potassium bisulfate, twice with 0.05 M aqueous sodium carbonate, and saturated aqueous sodium chloride. The organic layer is dried over magnesium sulfate and concentrated in vacuo. The residue is purified via silica gel flash chromatography eluting with hexanes and MTBE to give the title compound as a colorless liquid (1.82 g, 24% overall yield). $^1$H NMR (CDCl$_3$) δ 8.99 (s, 1H), 4.39 (q, 2H, J=7.1 Hz), 2.02 (m, 1H), 1.39 (t, 3H, J=7.1 Hz), 0.91 (m, 2H), 0.75 (m, 2H).

Preparation 29

3-[Cyclopropyl(difluoro)methyl]isoxazole-4-carboxylic acid

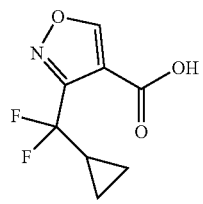

Scheme 7, step F: The title compound is prepared from ethyl 3-[cyclopropyl(difluoro)methyl]isoxazole-4-carboxylate in a manner essentially analogous to the method of Preparation 15. $^1$H NMR (CDCl$_3$) δ 9.11 (s, 1H), 2.02 (m, 1H), 0.93 (m, 2H), 0.76 (m, 2H).

Preparation 30

Ethyl 3-(1-methylcyclopropyl)isoxazole-4-carboxylate

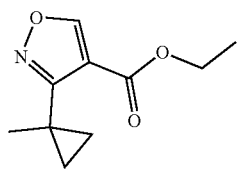

Scheme 3, steps A and B: To a suspension of PCC (19.35 g, 87.1 mmol) in DCM (88 mL) is added a solution of (1-methylcyclopropyl)methanol (6.76 mL, 69.6 mmol) in DCM (33 mL). The resulting black colored solution is stirred for 2 hours at ambient temperature. The reaction mixture is then filtered through a pad of silica, rinsing with DCM to afford a solution of 1-methylcyclopropanecarbaldehyde, which is used directly in the next step.

In a separate flask is added potassium carbonate (5.8 g, 41.8 mmol), hydroxylamine hydrochloride (5.3 g, 76.5 mmol), water (100 mL), and MeOH (100 mL). After the bubbling subsides, the aforementioned crude solution of 1-methylcyclopropanecarbaldehyde is added to the reaction mixture. After 30 minutes, the mixture is transferred to a separatory funnel and diluted with water. The mixture is extracted twice with diethyl ether. The combined organic layers are washed with saturated aqueous sodium chloride, dried over sodium sulfate, and concentrated in vacuo to afford crude 1-methylcyclopropanecarbaldehyde oxime, which is used without further purification assuming quantitative yield.

The resulting crude residue is dissolved in chloroform (70 mL), and to the mixture is added NCS (9.31 g, 69.7 mmol). The mixture is then heated to 45° C. for 2 hours. To the reaction is then added a solution of ethyl 3-(dimethylamino)prop-2-enoate (12 mL, 83.8 mmol) in chloroform (69 mL) followed by addition of TEA (19.5 mL, 140 mmol) dropwise. Upon completion of addition, the mixture is heated to 50° C. for 2 hours, then cooled to room temperature and stirred for 3 days. The reaction mixture is concentrated in vacuo and dissolved in DCM. This crude material is combined with another lot synthesized through an identical route on an 11.6 mmol scale. The combined lots are partitioned between DCM and saturated aqueous sodium bicarbonate, then the aqueous layer is extracted three times with DCM. The combined organic layers are washed with saturated aqueous sodium chloride, dried over sodium sulfate, and concentrated in vacuo. The resulting residue is purified via silica gel flash chromatography eluting with hexanes and MTBE to give the title compound as a colorless oil (4.94 g, 31% overall yield). ES/MS (m/z): 196.0 (M+H).

Preparation 31

3-(1-Methylcyclopropyl)isoxazole-4-carboxylic acid

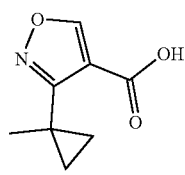

Scheme 3, step C: The title compound is prepared from ethyl 3-(1-methylcyclopropyl)isoxazole-4-carboxylate in an essentially analogous manner to the method of Preparation 15. $^1$H NMR (DMSO-d$_6$) δ 13.03 (s, 1H), 9.41 (s, 1H), 1.40 (s, 3H), 0.96 (m, 2H), 0.73 (m, 2H).

Preparation 32

Ethyl 3-(1-fluorocyclopropyl)isoxazole-4-carboxylate

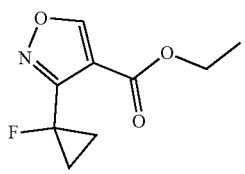

Scheme 8, steps A, B, and C: In a round bottom flask, 1-fluorocyclopropanecarboxylic acid (5.5 g, 53 mmol) is dissolved in THF (180 mL) and cooled to 0° C. and treated with lithium aluminum hydride (2 M in THF, 27 mL, 54 mmol). The reaction is allowed to warm to ambient temperature and stirred overnight. The reaction is quenched with dropwise addition of water (2.2 mL), followed by 1 N aqueous NaOH (2.2 mL), and finally water (7 mL). Magnesium sulfate (approximately 5 g) is added and the solution is stirred for one hour. The mixture is then filtered through a pad of diatomaceous earth, washing with DCM, and the filtrate is carefully concentrated in vacuo to afford crude (1-fluorocyclopropyl)methanol, which is used without further purification.

The resulting crude material is dissolved in DCM (100 mL) with silica gel (11 g, 183 mmol). The mixture is treated with PCC (14.3 g, 64.4 mmol) and the mixture is stirred for 2 hours. At this point additional PCC (5 g, 23.3 mmol) is added and the reaction is stirred overnight. Additional PCC (3 g, 13.9 mmol) is added and the mixture is stirred for 5 hours. The mixture is then diluted with DCM, and filtered through a pad of diatomaceous earth and silica gel to afford a DCM solution of 1-fluorocyclopropanecarbaldehyde, which is taken directly into the next step.

In a round bottom flask, hydroxylamine hydrochloride (3.6 g, 52 mmol) and potassium carbonate (4.6 g, 33 mmol) are dissolved in water (50 mL) and MeOH (50 mL). After the bubbling subsides, the aforementioned solution of 1-fluorocyclopropanecarbaldehyde is added and the reaction is stirred at ambient temperature overnight. The mixture is then combined with another lot of crude oxime made through an identical route starting from 4.80 mmol 1-fluorocyclopropanecarboxylic acid. The combined mixture is diluted with water and extracted three times with diethyl ether. The combined organic layers are washed with saturated aqueous sodium chloride, dried over sodium sulfate, and concentrated in vacuo to afford crude 1-fluorocyclopropanecarbaldehyde oxime as a pale yellow oil, which is used in the next step without further purification.

The crude oxime is dissolved in chloroform (50 mL) and treated with pyridine (0.3 mL, 4 mmol) and NCS (6.6 g, 49 mmol). The mixture is stirred under nitrogen and heated to 45° C. for 1.5 hours. To the mixture is added a solution of ethyl 3-(dimethylamino)prop-2-enoate (7.9 mL, 55 mmol) in chloroform (20 mL) followed by addition of TEA (13 mL, 93.3 mmol). The mixture is heated to 50° C. for 2 hours, then cooled to room temperature and stirred for 3 days. The mixture is then concentrated in vacuo, diluted with saturated sodium bicarbonate, and extracted three times with DCM. The combined organic layers are washed with saturated aqueous sodium chloride, dried over sodium sulfate, and concentrated in vacuo. The resulting residue is purified via silica gel flash chromatography eluting with hexanes and MTBE to give the title compound as a colorless liquid (3.4 g, 35% yield). ES/MS (m/z): 200.0 (M+H).

Preparation 33

3-(1-Fluorocyclopropyl)isoxazole-4-carboxylic acid

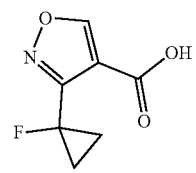

Scheme 8, step D: The title compound is prepared from ethyl 3-(1-fluorocyclopropyl)isoxazole-4-carboxylate in an essentially analogous manner to the method of Preparation 15. $^1$H NMR (DMSO-$d_6$) δ 13.28 (br s, 1H), 9.61 (s, 1H), 1.45 (m, 2H), 1.26 (m, 2H).

Preparation 34

3-(3,3-Difluorocyclobutyl)isoxazole-4-carboxylic acid

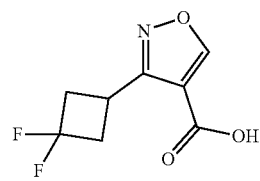

Scheme 3, steps A-D: The title compound is prepared from (3,3-difluorocyclobutyl)methanol in an essentially analogous manner to the methods found in Preparations 30 and 15. $^1$H NMR (DMSO-$d_6$) δ 13.24 (br s, 1H), 9.52 (s, 1H), 3.74 (m, 1H), 2.83-3.08 (m, 4H).

Preparation 35

Ethyl 3-cyclopropyl-2-hydroxyimino-3-oxo-propanoate

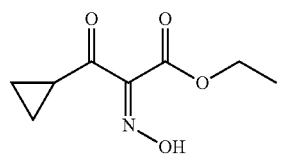

Scheme 9, step A: Ethyl 3-cyclopropyl-3-oxo-propanoate (4.78 g, 30.6 mmol) is dissolved in acetic acid (30 mL) and the solution is cooled to 8° C. A solution of sodium nitrite (3.17 g, 45.9 mmol) in water (10 mL) is added dropwise keeping the temperature below 15° C. The mixture is cooled to 5° C., then warmed to ambient temperature and stirred 18 hours. The crude reaction mixture is poured into a vigorously stirred mixture of EtOAc and aqueous saturated sodium bicarbonate. After gas evolution has ceased, the mixture is separated and the organic layer is washed with saturated sodium bicarbonate followed by saturated aqueous sodium chloride. The organic layer is dried over sodium sulfate, filtered, and concentrated in vacuo to give the title compound as a pale yellow liquid (5.70 g, 100%).

ES/MS (m/z): 186.0 (M+H).

Preparation 36

Ethyl 2-hydroxyimino-4-methyl-3-oxo-pentanoate

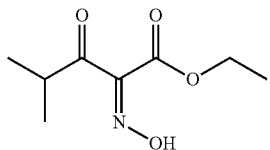

Scheme 9, step A: The title compound is prepared from ethyl isobutyrylacetate in an essentially analogous manner to the methods found in Preparation 35. ES/MS m/z 188.0 (M+H).

Preparation 37

Methyl 2-hydroxyimino-3-oxo-pentanoate

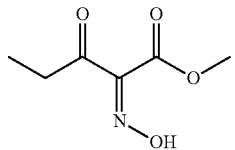

Scheme 9, step A: The title compound is prepared from methyl 3-oxovalerate in an essentially analogous manner to the methods found in Preparation 35. ES/MS m/z 160.0 (M+H).

Preparation 38

Ethyl 4,4-difluoro-2-hydroxyimino-3-oxo-butanoate

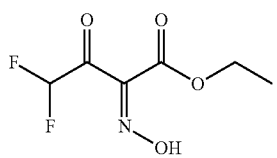

Scheme 9, step A: The title compound is prepared from ethyl 4,4-difluoro-3-oxo-butanoate in an essentially analogous manner to the methods found in Preparation 35. ES/MS m/z 196.0 (M+H).

Preparation 39

Ethyl 3-cyclopropyl-2,3-bis(hydroxyimino)propanoate

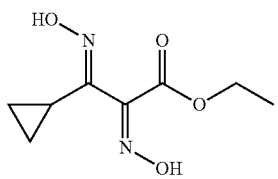

Scheme 9, step B: Ethyl 3-cyclopropyl-2-hydroxyimino-3-oxo-propanoate (2.65 g, 14.3 mmol) is dissolved in EtOH (70 mL) and hydroxylamine hydrochloride (2.98 g, 42.9 mmol) and sodium acetate (2.35 g, 28.6 mmol) are added. The mixture is heated to 80° C. for 18 hours, then cooled to ambient temperature and concentrated in vacuo to ~10 mL volume. EtOAc and water are added. The layers are separated and the organic layer is washed four time with water followed by saturated sodium chloride. The organic layer is dried over sodium sulfate, filtered, and concentrated in vacuo to give the title compound as a crude yellow oil (1.17 g, 41%). ES/MS (m/z): 201.0 (M+H).

Preparation 40

Ethyl 2,3-bis(hydroxyimino)-4-methyl-pentanoate

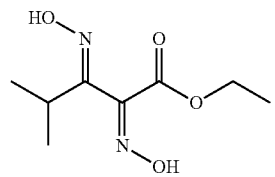

Scheme 9, step B: The title compound is prepared from ethyl 2-hydroxyimino-4-methyl-3-oxo-pentanoate in an essentially analogous manner to the methods found in Preparation 39. ES/MS m/z 203.0 (M+H).

Preparation 41

Methyl 2,3-bis(hydroxyimino)pentanoate

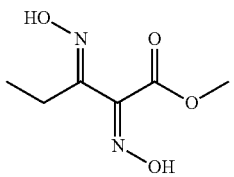

Scheme 9, step B: The title compound is prepared from methyl 2-hydroxyimino-3-oxo-pentanoate in an essentially analogous manner to the methods found in Preparation 39. ES/MS m/z 175.0 (M+H).

Preparation 42

Ethyl 4,4-difluoro-2,3-bis(hydroxyimino)butanoate

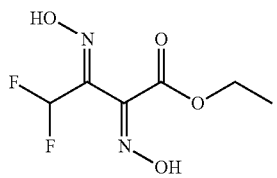

Scheme 9, step B alternative procedure: To a pressure bottle, ethyl 4,4-difluoro-2-hydroxyimino-3-oxo-butanoate (43 g, 132 mmol), hydroxylamine hydrochloride (41 g, 584 mmol), EtOH (150 mL) and 4 M HCl in dioxane (600 mmol, 150 mL) are added. The bottle is sealed and the mixture stirred at 50° C. until complete consumption of starting material. After cooling to room temperature the excess hydroxylamine hydrochloride is filtered off and rinsed with diethyl ether. The filtrate is concentrated in vacuo at 40° C. The residue is carefully neutralized with saturated aqueous sodium bicarbonate and extracted with diethyl ether. The combined organic layers are dried over magnesium sulfate and filtered. The solvent is removed under reduced pressure and the residue purified by silica gel flash chromatography eluting with EtOAc and DCM to give the title compound as yellow liquid (4.9 g, 18%). ES/MS (m/z): 211.0 (M+H).

Preparation 43

Ethyl 4,4,4-trifluoro-2,3-bis(hydroxyimino)butanoate

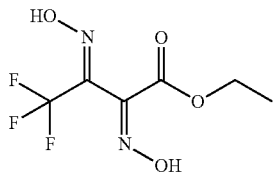

Scheme 9, step A, B: A solution of sodium nitrite (4.5 g, 64.6 mmol) in water (27 mL) is added dropwise to a 0° C. solution of ethyl 4,4,4-trifluoroacetoacetate (10.0 g, 53.8 mmol) in acetic acid (36 mL). The reaction is allowed to slowly warm to ambient temperature and stirred for 5 hours. To the mixture is added water (100 mL), and the mixture is extracted with diethyl ether (4×100 mL). The combined organic extracts are washed with saturated sodium bicarbonate (5×50 mL) and saturated aqueous sodium chloride (50 mL). The organic layers are dried over magnesium sulfate and concentrated in vacuo. The resulting residue is purified by silica gel flash chromatography eluting with hexanes and EtOAc to obtain an impure product (10.13 g) which is carried into the next step without further purification.

The resulting residue is dissolved in EtOH (240 mL) and hydroxylamine hydrochloride (9.75 g, 140 mmol) and sodium acetate (7.85 g) are added. The mixture is heated to 80° C. After 5 hours, the mixture is cooled to room temperature, filtered, and concentrated in vacuo. The residue is dissolved in diethyl ether (400 mL) and washed with saturated aqueous sodium bicarbonate (1×100 mL). The aqueous layers are extracted with diethyl ether (100 mL) and the combined organic layers are washed with saturated aqueous sodium chloride (50 mL), dried over magnesium sulfate, and concentrated in vacuo. The residue is purified via silica gel flash chromatography eluting with hexanes and EtOAc to give the title compound as a mixture of 2 isomers as a reddish oil (2.58 g, 24% overall yield). $^1$H NMR (DMSO-$d_6$) δ 13.46 (s, 1H), 13.15 (s, 1H), 4.25 (q, 2H, J=7.0), 4.0 (q, 2H, J=7.1 Hz), 1.24 (t, 3H, J=7.1 Hz), 1.18 (t, 3H, J=7.1 Hz).

Preparation 44

Ethyl 4-cyclopropyl-1,2,5-oxadiazole-3-carboxylate

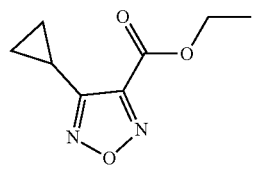

Scheme 9, step C: Ethyl 3-cyclopropyl-2,3-bis(hydroxyimino)propanoate (1.17 g, 5.84 mmol) is dissolved in THF (23 mL) and CDI (1.42 g, 8.77 mmol) is added. The mixture is stirred at ambient temperature for 2 hours. The mixture is concentrated in vacuo then purified via silica gel flash chromatography eluting with hexanes and EtOAc to give the title compound as a colorless oil (90 mg, 8%). $^1$H NMR (CDCl3) δ 4.50 (q, J=7.0 Hz, 2H), 2.36-2.45 (m, 1H), 1.45 (t, J=7.2 Hz, 3H), 1.14-1.19 (m, 2H), 1.08-1.13 (m, 1H). $^{13}$C NMR (CDCl3) δ 158.8, 158.3, 147.1, 62.8, 14.1, 11.9, 10.2, 4.7.

Preparation 45

Ethyl 4-isopropyl-1,2,5-oxadiazole-3-carboxylate

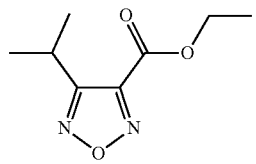

Scheme 9, step C: The title compound is prepared from ethyl 2,3-bis(hydroxyimino)-4-methyl-pentanoate in an essentially analogous manner to the methods found in Preparation 44. $^1$H NMR (CDCl3) δ 4.50 (q, J=7.1 Hz, 2H), 3.47-3.54 (m, 1H), 1.45 (t, J=7.2 Hz, 3H), 1.41 (s, 3H), 1.39 (s, 3H).

Preparation 46

Methyl 4-ethyl-1,2,5-oxadiazole-3-carboxylate

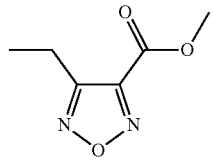

Scheme 9, step C: The title compound is prepared from methyl 2,3-bis(hydroxyimino)pentanoate in an essentially analogous manner to the methods found in Preparation 44. $^1$H NMR (d6-DMSO) δ 3.95 (s, 3H), 2.96 (q, J=7.5 Hz, 2H), 1.29 (t, J=7.4 Hz, 3H). $^{13}$C NMR (d6-DMSO) δ 159, 157, 148, 54, 18, 12.

Preparation 47

Ethyl 4-(difluoromethyl)-1,2,5-oxadiazole-3-carboxylate

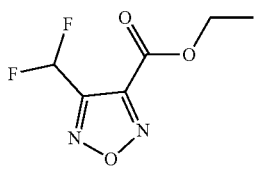

Scheme 9, step C: The title compound is prepared from ethyl 4,4-difluoro-2,3-bis(hydroxyimino)butanoate in an essentially analogous manner to the methods found in Preparation 44. $^1$H NMR (d6-DMSO) δ 7.47 (t, J=51.71 Hz, 1H), 4.46 (q, J=7.1 Hz, 2H), 1.37 (t, J=7.1 Hz, 3H). $^{13}$C NMR (d6-DMSO) δ 156, 151, 147, 110, 108, 105, 63, 14.

Preparation 48

Ethyl 4-(trifluoromethyl)-1,2,5-oxadiazole-3-carboxylate

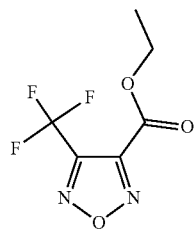

Scheme 9, step C: The title compound is prepared from ethyl 4,4,4-trifluoro-2,3-bis(hydroxyimino)butanoate in an essentially analogous manner to the methods found in Preparation 44. $^1$H NMR (d6-DMSO) δ 4.46 (q, J=7.1 Hz, 2H), 1.35 (t, J=7.1 Hz, 3H). $^{19}$F NMR (d6-DMSO) δ 60.46 (3 F).

Preparation 49

4-Ethyl-1,2,5-oxadiazole-3-carboxylic acid

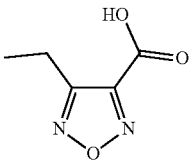

Scheme 9, step D: To a mixture of methyl 4-ethyl-1,2,5-oxadiazole-3-carboxylate (438 mg, 2.81 mmol) in THF (10 mL) and water (10 mL), 2 M LiOH in water (3.5 mL, 3.5 mmol) is added. The mixture is stirred at room temperature for 20 min and concentrated in vacuo. The residue is diluted with water and washed with diethyl ether. The aqueous layer is acidified with 1 N aqueous HCl and extracted with diethyl ether. The combined organic layers are dried over magnesium sulfate, filtered, and concentrated in vacuo to give the title compound as an oil which solidifies on standing (382 mg, 96%). $^1$H NMR (DMSO-d6) δ 2.96 (q, J=7.5 Hz, 2H), 1.27 (t, J=7.5 Hz, 3H).

Preparation 50

4-(Difluoromethyl)-1,2,5-oxadiazole-3-carboxylic acid

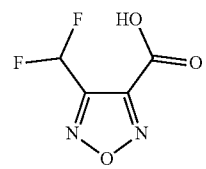

Scheme 9, step D, alternative procedure: In a microwave vial, ethyl 4-(difluoromethyl)-1,2,5-oxadiazole-3-carboxylic acid (400 mg, 2.08 mmol) is dissolved in water (5 mL) and 1,4-dioxane (5 mL). To the mixture is added concentrated aqueous HCl (12 M, 2 mL). The vial is sealed and the mixture is stirred at 100° C. for approximately 3.5 hours. After cooling to room temperature, the mixture is diluted with water and extracted with diethyl ether. The combined organic layers dried over magnesium sulfate, filtered, and concentrated in vacuo to give the title compound containing 40% 1,4-dioxane (365 mg, 64%). $^1$H NMR (DMSO-d6) δ 7.12-6.86 (t. J=53 Hz, 1H).

Preparation 51

4-Amino-N-methyl-1,2,5-oxadiazole-3-carboxamide

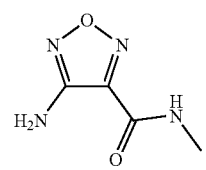

Scheme 10, Step A: To ethyl 4-amino-1,2,5-oxadiazole-3-carboxylate (2.00 g, 12.5 mmol) is added methylamine (33% in EtOH, 30 mL, 241 mmol). The mixture is heated to reflux for 10 minutes, then allowed to stir at room temperature for 2 hours. The crude reaction mixture is combined with a separate reaction performed identically on 300 mg scale, and the solution is concentrated in vacuo. The resulting dark brown solid is triturated with MeOH to remove colored impurities. The solid is filtered and washed with 1:1 MeOH:diethyl ether. The solid is dried in a vacuum oven to give the title compound (2.01 g, 99% yield). $^1$H NMR (MeOD) δ 2.92 (s, 3H).

Preparation 52

4-Chloro-N-methyl-1,2,5-oxadiazole-3-carboxamide

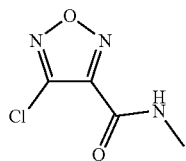

Scheme 10, Step B: To a 0° C. solution of 4-amino-N-methyl-1,2,5-oxadiazole-3-carboxamide (1.00 g, 7.04 mmol) in acetonitrile (25 mL) is added acetic acid (25 mL, 436 mmol) followed by a solution of LiCl (895 mg, 21.1 mmol) in concentrated HCl (12 M, 18.1 mL). To the mixture is added a solution of sodium nitrite (728 mg, 10.55 mmol) in water (1.2 mL) dropwise. After 2 hours, the reaction is diluted with saturated aqueous ammonium chloride (100 mL). The mixture is extracted with EtOAc (3×100 mL). The combined organic layers are washed with saturated aqueous sodium chloride, then twice with saturated aqueous sodium bicarbonate, then once more with saturated aqueous sodium chloride. The organic layers are dried over sodium sulfate, filtered and concentrated in vacuo. The resulting crude oil is dissolved in DCM (60 mL), washed once more with saturated aqueous sodium bicarbonate, then dried over sodium sulfate, and concentrated in vacuo to afford the title compound as a white solid (774 mg, 68% yield). $^1$H NMR (CDCl$_3$) δ 6.76 (br s, 1H), 3.07 (d, 3H, J=5.1 Hz).

Preparation 53

4-Methoxy-N-methyl-1,2,5-oxadiazole-3-carboxamide

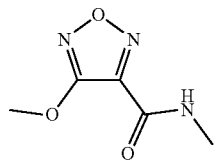

Scheme 10, Step C: To a flask containing 4-chloro-N-methyl-1,2,5-oxadiazole-3-carboxamide (333 mg, 2.06 mmol) in MeOH (2 mL) is added sodium methoxide (0.5 M in MeOH, 10 mL, 5 mmol). The mixture is heated to 50° C. for 2 hours, then the reaction mixture is concentrated. The crude residue is dissolved in DCM and washed with saturated aqueous ammonium chloride. The organic layer is dried over sodium sulfate, filtered, and concentrated in vacuo to afford the title compound as a white solid (309 mg, 95% yield). ES/MS (m/z) 158.0 (M+H).

Preparation 54 tert-Butyl N-(4-methoxy-1,2,5-oxadiazole-3-carbonyl)-N-methyl-carbamate

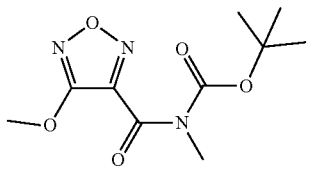 [SMILES: COc1nonc1C(=O)N(C)C(=O)OC(C)(C)C]

Scheme 10, Step D: To a solution of 4-methoxy-N-methyl-1,2,5-oxadiazole-3-carboxamide (300 mg, 1.91 mmol) in DCM (5 mL) is added DMAP (25 mg, 0.21 mmol) and di-tert-butyl dicarbonate (630 mg, 2.88 mmol). The mixture is stirred overnight at room temperature. The resulting solution is concentrated in vacuo and purified by silica gel flash chromatography eluting with DCM and hexanes to give the title compound as a colorless oil (420 mg, 82% yield). ES/MS (m/z) 280.0 (M+Na).

Preparation 55

Methyl 6-(tert-butoxycarbonylamino)pyridazine-4-carboxylate

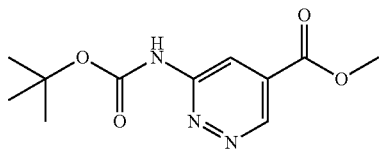 [SMILES: COC(=O)c1cnnc(NC(=O)OC(C)(C)C)c1]

Scheme 11, step A: In an oven-dried flask is added methyl 6-chloropyridazine-4-carboxylate (25.0 g, 142 mmol), potassium carbonate (42.0 g, 303.8 mmol), tert-butyl carbamate (35.0 g, 292.7 mmol), Pd$_2$(dba)$_3$ (3.40 g, 3.71 mmol), and DTBPF (3.70 g, 7.72 mmol). The flask is evacuated and refilled with nitrogen, then toluene (270 mL) is added via syringe. The flask is then evacuated, refilled and evacuated with nitrogen three times, and finally evacuated and refilled with argon. The resulting mixture is heated at 75° C. for 6 hours. After this time, the reaction is filtered through a plug of silica gel covered with a layer of diatomaceous earth eluting with EtOAc. The filtrate is concentrated in vacuo to give the title compound (35.95 g, 100%). ES/MS (m/z): 254 (M+H).

Preparation 56

6-(tert-Butoxycarbonylamino)pyridazine-4-carboxylic acid

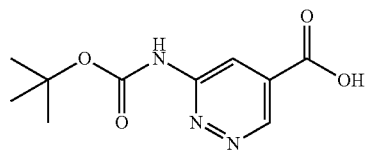 [SMILES: CC(C)(C)OC(=O)Nc1cc(C(=O)O)cnn1]

Scheme 11, step B: Aqueous 5 N NaOH (32.0 mL, 160 mmol) is added to a flask containing methyl 6-(tert-butoxycarbonylamino)pyridazine-4-carboxylate (35.95 g, 142 mmol) in MeOH (300 mL) and water (130 mL) and the solution is stirred for ten minutes. After this time, the MeOH is removed via rotary evaporation. The resulting mixture is diluted with water (70 mL) and washed with DCM (250 mL, 3×50 mL). The aqueous phase is transferred to a round bottom flask and 5 N aqueous HCl (33 mL, 165 mmol) is added over 2 minutes with stirring and a thick white precipitate is formed. The precipitate is vacuum filtered, washed with ice cold water (100 mL), and air dried under suction. The resulting solid is transferred to a flask, co-evaporated with acetone/MeOH (1:1), and co-evaporated with toluene. The resulting light brown solid is dried in a vacuum oven at 40° C. for 20 hours to give the title compound (28.48 g, 83%). ES/MS (m/z): 240.0 (M+H).

Preparation 57 tert-Butyl N-[5-(hydroxymethyl)pyridazin-3-yl]carbamate

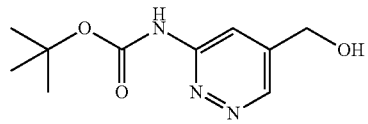 [SMILES: CC(C)(C)OC(=O)Nc1cc(CO)cnn1]

Scheme 11, step C: In a flask, 6-(tert-butoxycarbonylamino)pyridazine-4-carboxylic acid (13.38 g, 55.9 mmol) is dissolved in THF (400 mL) and TEA (9.80 mL, 70 mmol). The reaction is evacuated, placed under nitrogen, and cooled to 0° C. Ethyl chloroformate (6.70 mL, 70 mmol) is added over a period of 1.5 minutes followed by 15 minutes of stirring. The reaction mixture is then cooled to −60° C. and stirred for 10 minutes After this time, sodium borohydride (5.91 g, 156 mmol) is added followed by MeOH (400 mL, cooled in a −78° C. dry ice/acetone bath for 20 minutes). The mixture is allowed to warm to −30° C. over a period of 30 minutes, at which point the reaction is brought to 0° C. After 80 minutes, the resulting mixture is quenched with acetone (50 mL). The crude mixture is concentrated in vacuo and partitioned between EtOAc and saturated aqueous sodium bicarbonate. The aqueous layer is extracted once more with EtOAc. The combined organic layers are dried over magnesium sulfate and concentrated in vacuo. The resulting residue is purified via silica gel flash chromatography eluting with hexanes and acetone to give the title compound as a pale yellow solid of acceptable purity (7.90 g, 59%). ES/MS (m/z): 226.0 (M+H).

Preparation 58 tert-Butyl N-(5-formylpyridazin-3-yl)carbamate

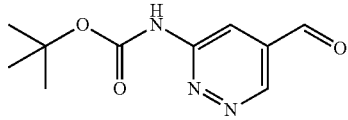 [SMILES: CC(C)(C)OC(=O)Nc1cc(C=O)cnn1]

Scheme 11, step D: To a suspension of tert-butyl N-[5-(hydroxymethyl)pyridazin-3-yl]carbamate (7.90 g, 33.0 mmol) in DCM (165 mL) is added Dess-Martin periodinane (16.8 g, 39.6 mmol) followed by additional DCM (70 mL). The reaction mixture is stirred for 2 hours 50 minutes, at which point additional Dess-Martin periodinane (1.80 g, 4.2 mmol) is added. The mixture is stirred for an additional 5 minutes then quenched with saturated aqueous sodium bicarbonate (150 mL) and sodium thiosulfate (29.0 g, 183.5 mmol). The mixture is stirred rapidly for 30 minutes, after which the layers are separated. The aqueous layer is extracted once more with DCM. The combined organic layers are washed with water, dried over magnesium sulfate, and concentrated in vacuo to give the crude title compound which is used without further purification (7.36 g, 100%). ES/MS (m/z): 222.0 (M−H).

Preparation 59 tert-Butyl N-[5-[[[(2S)-2-amino-3,3,3-trifluoro-propyl]amino]methyl]pyridazin-3-yl]carbamate

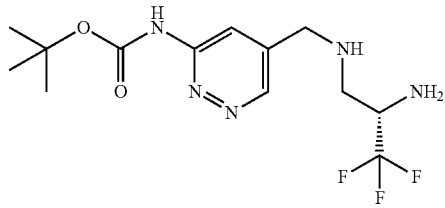 [SMILES: CC(C)(C)OC(=O)Nc1cc(CNC[C@H](N)C(F)(F)F)cnn1]

Scheme 11, step E: tert-Butyl N-(5-formylpyridazin-3-yl) carbamate (7.36 g, 33.0 mmol) is dissolved in DCM (245 mL). (2S)-3,3,3-Trifluoropropane-1,2-diamine; dihydrochloride (6.63 g, 33.0 mmol) is added followed by TEA (10.1 mL, 72.4 mmol). The resulting mixture is stirred at room temperature for 10 minutes followed by 40 minutes of heating at 40° C. After this time, the reaction is cooled to room temperature and sodium cyanoborohydride (7.25 g, 115 mmol), MeOH (30 mL), and acetic acid (9.5 mL, 170 mmol) are added. The mixture is stirred for 20 minutes and is then concentrated in vacuo. The resulting residue is dissolved in DCM (100 mL) and stirred rapidly with saturated aqueous sodium bicarbonate (100 mL). The layers are separated and the aqueous phase is extracted with DCM (2×100 mL). The combined organic layers are dried over magnesium sulfate and concentrated in vacuo to give the title compound as an orange oil which is used without further purification (11.1 g, 100%). ES/MS (m/z): 336.0 (M+H).

Preparation 60 tert-Butyl N-[5-[[(4S)-2-oxo-4-(trifluoromethyl)imidazolidin-1-yl]methyl]pyridazin-3-yl]carbamate

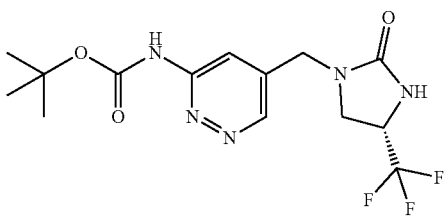 [SMILES: CC(C)(C)OC(=O)Nc1cc(CN2C[C@@H](C(F)(F)F)NC2=O)cnn1]

Scheme 11, step F: tert-Butyl N-[5-[[[(2S)-2-amino-3,3,3-trifluoro-propyl]amino]methyl]pyridazin-3-yl]carbamate (11.1 g, 33.0 mmol) is dissolved in THF (300 mL) and heated to 65° C. for 5 minutes. CDI (16.1 g, 99.3 mmol) is then added and the reaction is stirred for 50 minutes. After this time, the heat is removed and the reaction is carefully quenched with 1 N NaOH (80 mL). Approximately ⅔ of the solvent is removed in vacuo. The mixture is diluted with EtOAc and water The layers are separated and the aqueous phase is extracted once more with EtOAc. The combined organic layers are washed sequentially with water and saturated aqueous sodium chloride, dried over magnesium sulfate, and concentrated in vacuo. The resulting residue is purified via silica gel flash chromatography eluting with DCM and acetone to give the title compound as a pale yellow solid (6.88 g, 58%). ES/MS (m/z): 362.0 (M+H).

Preparation 61

(4S)-1-[(6-Aminopyridazin-4-yl)methyl]-4-(trifluoromethyl)imidazolidin-2-one; hydrochloride

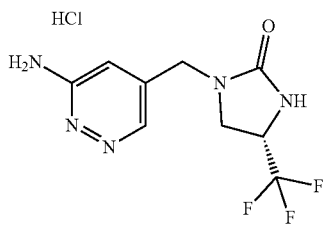 [SMILES: Cl ; Nc1cc(CN2C[C@@H](C(F)(F)F)NC2=O)cnn1]

Scheme 11, step G: 4 M HCl in dioxane (200 mL, 800 mmol) is added to a suspension of tert-butyl N-[5-[[(4S)-2-oxo-4-(trifluoromethyl)imidazolidin-1-yl]methyl]pyridazin-3-yl]carbamate (6.88 g, 19.0 mmol) in MeOH (70 mL) and the mixture is heated to 50° C. After 80 minutes, the mixture is concentrated in vacuo, dissolved in MeOH, and concentrated in vacuo again. The resulting residue is dissolved in a mixture of MeOH/heptane (2:1) and concentrated in vacuo. The resulting foam is dissolved again in MeOH and concentrated in vacuo to give the title compound as a colorless hygroscopic powder (5.44 g, 96%). ES/MS (m/z): 262.0 (M+H).

Preparation 62

Benzyl N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]carbamate

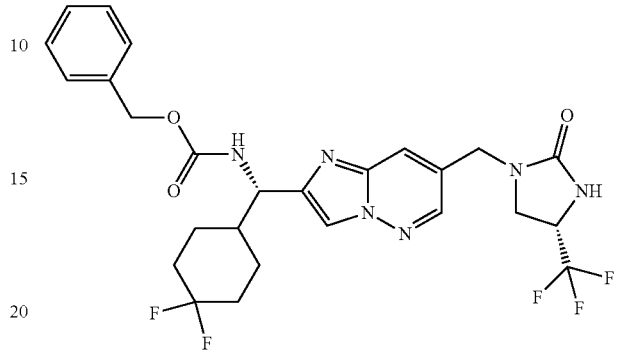

Scheme 12, step A: Three reactions are set up in parallel: To a vial is added (4S)-1-[(6-aminopyridazin-4-yl)methyl]-4-(trifluoromethyl)imidazolidin-2-one; hydrochloride (700 mg, 2.35 mmol) and benzyl (S)-(3-bromo-1-(4,4-difluorocyclohexyl)-2-oxopropyl)carbamate (1.25 g, 3.1 mmol). THF (14 mL), trimethyl borate (1.30 mL, 11.4 mmol), and DIEA (1.70 mL, 9.75 mmol) are then added. The reaction vial is sealed and heated to 80° C. for 7.5 hours. The three reactions are cooled to ambient temperature, combined, and concentrated in vacuo. The resulting residue is purified via silica gel flash chromatography eluting with DCM and acetone to give the title compound as a light orange solid (1.70 g, 42%). ES/MS (m/z): 468.2 (M+H).

Preparation 63

(4S)-1-[[2-[(S)-Amino-(4,4-difluorocyclohexyl)methyl]imidazo[1,2-b]pyridazin-7-yl]methyl]-4-(trifluoromethyl)imidazolidin-2-one

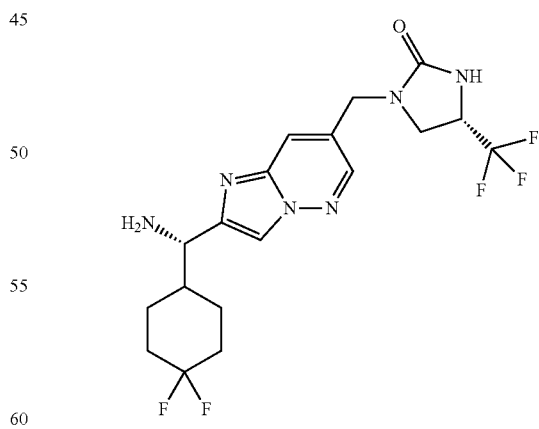

Scheme 12, step B: To a hydrogenation vessel is added Benzyl N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]carbamate (580 mg, 1.0 mmol), EtOH (15 mL), and 10% Pd/C (560 mg, 0.53 mmol). The vessel is sealed, evacuated under reduced pressure, and charged to 10 psi with hydrogen. The degassing procedure is repeated 3 times before charging again with hydrogen at 10 psi. After stirring for 1.5 hours at room temperature, the mixture is passed through a pad of diatomaceous earth and the solvent is concentrated in vacuo to give the title compound of sufficient purity (377 mg, 81%). ES/MS (m/z): 433.2 (M+H).

Preparation 64

Ethyl 5,5,5-trifluoro-2-hydroxyimino-3-oxo-pentanoate

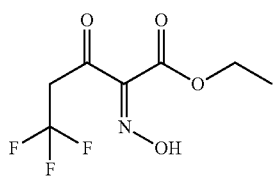

Scheme 9, step A: The title compound is prepared from ethyl 5,5,5-trifluoro-3-oxo-pentanoate in an essentially analogous manner to the methods found in Preparation 35. ES/MS (m/z): 228.0 (M+H).

Preparation 65

Ethyl 5,5,5-trifluoro-2,3-bis(hydroxyimino)pentanoate

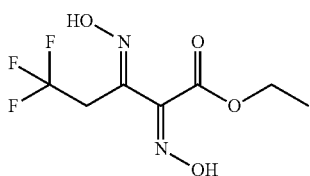 [SMILES: CCOC(=O)C(=N\O)/C(CC(F)(F)F)=N/O]

Scheme 9, step B: The title compound is prepared from ethyl 5,5,5-trifluoro-2-hydroxyimino-3-oxo-pentanoate in an essentially analogous manner to the methods found in Preparation 39. ES/MS (m/z): 243.0 (M+H).

Preparation 66

Ethyl 4-(2,2,2-trifluoroethyl)-1,2,5-oxadiazole-3-carboxylate

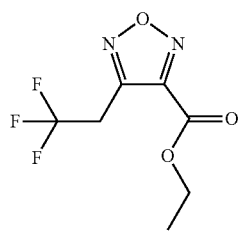

Scheme 9, step C: The title compound is prepared from ethyl 5,5,5-trifluoro-2,3-bis(hydroxyimino)pentanoate in an essentially analogous manner to the methods found in Preparation 44. $^1$H NMR (d6-DMSO) δ 4.54 (q, J=7.2 Hz, 2H), 4.01 (q, J=9.7 Hz, 2H), 1.48 (t, J=7.1 Hz, 3H).

Preparation 67

N-(6-Chloro-5-methyl-pyridazin-3-yl)-2,2-dimethyl-propanamide

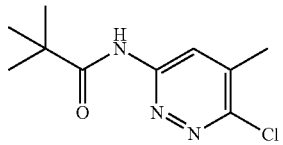

Scheme 13, step A: To a 4 L jacketed fixed reactor equipped with overhead stirring, internal temperature probe, and nitrogen blanket is added 6-chloro-5-methyl-pyridazin-3-amine (250 g, 1.74 mol) as a solid. To the reactor is added 1-methyl-2-pyrrolidinone (1.0 L) followed by pyridine (280 mL, 3.46 mol). The mixture is cooled to an internal temperature of 15° C., and pivaloyl chloride (280 mL, 2.29 mol) is added in a slow stream, resulting in an exotherm reaching 35° C. over 10-15 minutes. After 1 hour, the mixture is warmed to 35° C. for an additional 30 minutes, then allowed to cool back to 15° C. To the mixture is added water (1.5 L) dropwise, whereupon the mixture is stirred for one hour at 5° C. The resulting thick slurry is filtered to collect the solids, which are washed with cold water (1 L). The solids are dried under nitrogen pressure for 24 hours to give the title compound as a white solid (365 g, 92%). ES/MS m/z ($^{35}$Cl/$^{37}$Cl) 228.0/230.0 [M+H]$^+$.

Preparation 68

N-[6-Chloro-5-[(E)-2-(dimethylamino)vinyl]pyridazin-3-yl]-2,2-dimethyl-propanamide

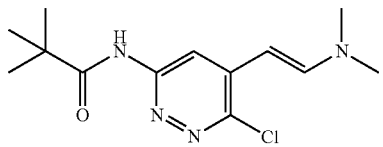 [SMILES: CN(C)/C=C/c1cc(NC(=O)C(C)(C)C)nnc1Cl]

Scheme 13, step B: To a flask containing N-(6-chloro-5-methyl-pyridazin-3-yl)-2,2-dimethyl-propanamide (34.0 g, 149 mmol) is added 1,1-diethoxy-N,N-dimethyl-methanamine (100 mL, 583 mmol) and DMF (13 mL). The mixture is then heated to 120° C. with stirring under a nitrogen atmosphere. After 5 hours, stirring is stopped and the mixture is allowed to stand at room temperature for 1 hour and 50 minutes. During this time, large yellow crystals are deposited on the bottom of the flask. The resulting solids are filtered, rinsed with diethyl ether (150 mL), and dried overnight in a vacuum oven at 45° C. to give the title compound as a yellow crystalline solid (25.68 g, 61%). ES/MS m/z ($^{35}$Cl/$^{37}$Cl) 283.0/285.0 [M+H]$^+$.

Preparation 69

N-(6-Chloro-5-formyl-pyridazin-3-yl)-2,2-dimethyl-propanamide

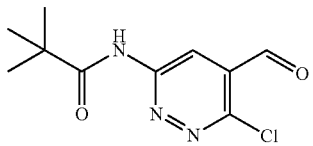 [SMILES: CC(C)(C)C(=O)Nc1cc(C=O)c(Cl)nn1]

Scheme 13, step C: To a suspension of N-[6-chloro-5-[(E)-2-(dimethylamino)vinyl]pyridazin-3-yl]-2,2-dimethyl-propanamide (25.58 g, 90.45 mmol) in THF (150 mL) and water (150 mL) is added sodium periodate (67.5 g, 316 mmol) which forms a thick white precipitate within a few minutes. The mixture is stirred vigorously for 45 minutes. After this time, the solids are filtered and rinsed with EtOAc. The resulting filtrate is transferred to a separatory funnel and extracted twice with EtOAc. The combined organic layers are washed twice with saturated aqueous sodium chloride solution, dried over MgSO$_4$, and concentrated in vacuo. The resulting residue is purified via silica gel chromatography eluting with hexanes and EtOAc to give the title compound as a light yellow solid (19.28 g, 82%). ES/MS m/z ($^{35}$Cl/$^{37}$Cl) 242.0/244.0 [M+H]$^+$.

Preparation 70

N-[6-Chloro-5-(1-hydroxy-2-methoxy-ethyl)pyridazin-3-yl]-2,2-dimethyl-propanamide

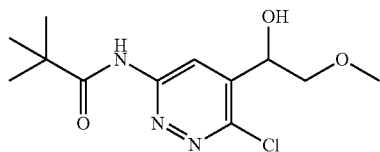 [SMILES: COCC(O)c1cc(NC(=O)C(C)(C)C)nnc1Cl]

Scheme 13, step D: A suspension of magnesium turnings (12.7 g, 522 mmol) in THF (200 mL) is purged with nitrogen gas. To the turnings is added 1,2-dibromoethane (3 mL, 34.5 mmol), and the mixture is gently warmed with a heat gun until bubbling occurs. Upon initiation, additional 1,2-dibromoethane (1 mL, 2.18 mmol) is added. The mixture is allowed to reach ambient temperature over approximately 20 minutes, and stirred for a further 10 minutes. To the mixture is then added mercuric chloride (700 mg, 2.57 mmol), resulting in a cloudy suspension that is stirred for 30 minutes, then cooled in a −15° C. dry ice/acetone bath. A solution of methyl chloromethyl ether (35 mL, 453 mmol) in THF (100 mL) is added dropwise over 30 minutes, resulting in a temperature increase to −8° C. After addition is complete, the reaction is cooled to −25° C. and stirred for 2 hours allowing the temperature to rise to −6° C. In a separate flask, N-(6-chloro-5-formyl-pyridazin-3-yl)-2,2-dimethyl-propanamide (21 g, 86.9 mmol) is dissolved in THF (100 mL), placed under nitrogen, and cooled to −78° C. The aforementioned Grignard reagent solution is added via cannula, resulting in formation of a precipitate. Following addition, the cooling bath is removed and the reaction is stirred at ambient temperature for 20 minutes. The reaction is quenched upon the addition of saturated aqueous NH$_4$Cl and extracted twice with EtOAc. The combined organic layers are washed with saturated aqueous NH$_4$Cl followed by saturated aqueous sodium chloride solution, dried over MgSO4, and concentrated in vacuo. The crude material is triturated with EtOAc (150 mL) and hexanes (200 mL), and the solids are collected via filtration. The filtrate is concentrated and purified via silica gel chromatography eluting with hexanes and EtOAc. The purified material and initially collected solids are combined to give the title compound (13.66 g, 55%). ES/MS m/z ($^{35}$Cl/$^{37}$Cl) 288.0/290.0 [M+H]$^+$.

Preparation 71

N-[6-Chloro-5-[(1S)-2-methoxy-1-[(4S)-2-oxo-4-(trifluoromethyl)imidazolidin-1-yl]ethyl]pyridazin-3-yl]-2,2-dimethyl-propanamide

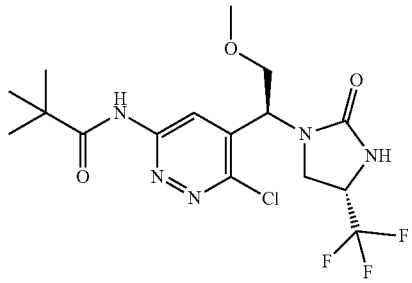 [SMILES: COC[C@H](c1cc(NC(=O)C(C)(C)C)nnc1Cl)N1C[C@@H](C(F)(F)F)NC1=O]

Scheme 13, steps E-G: To a solution of N-[6-chloro-5-(1-hydroxy-2-methoxy-ethyl)pyridazin-3-yl]-2,2-dimethyl-propanamide (13.66 g, 47.47 mmol) in DCM (500 mL) is added Dess-Martin periodinane (27.0 g, 61.7 mmol). The mixture is stirred at ambient temperature under nitrogen. After 3 hours, the reaction is quenched with sodium thiosulfate (31 g, 193 mmol) followed by saturated aqueous NaHCO$_3$ and stirred for 1 hour. The layers are separated, and the organic layer is washed with saturated aqueous Na$_2$S$_2$O$_3$, saturated aqueous NaHCO$_3$, then saturated aqueous sodium chloride solution. The organic layer is dried over MgSO$_4$, filtered, and concentrated in vacuo. The resulting ketone is used without further purification. ES/MS (m/z): 286.0 (M+H).

The crude ketone and (2S)-3,3,3-trifluoropropane-1,2-diamine; dihydrochloride (14.6 g, 72.6 mmol) are suspended in isopropyl alcohol (150 mL). Triethylamine (21 mL, 149 mmol) is added and the mixture is stirred at 75° C. for 2 hours, then stirred at ambient temperature overnight. The mixture is concentrated in vacuo and dissolved in MeOH (250 mL). Sodium cyanoborohydride (17.8 g, 269 mmol) is added portionwise, with gas evolution occurring. The resulting suspension is stirred for 5 minutes, then acetic acid (20 mL, 346 mmol) is added. The reaction is heated at 40° C. with stirring for 30 minutes, at which point it is cooled and concentrated in vacuo. The residue is diluted with DCM (200 mL) and neutralized with saturated aqueous NaHCO$_3$ with vigorous stirring. The layers are separated and the aqueous layer is extracted with DCM (2×50 mL). The combined organic layers are washed with saturated aqueous NaHCO$_3$ (50 mL) and saturated aqueous sodium chloride solution (50 mL), dried over MgSO$_4$, filtered, and concentrated in vacuo. The resulting diamine is used without further purification. ES/MS (m/z): 398.0 (M+H).

The crude diamine is dissolved in THF (150 mL) and heated to 60° C. To the mixture is added 1,1'-carbonyldiimidazole (19.4 g, 116 mmol) portionwise. The reaction is allowed to stir at this temperature for 1 hour, at which point the reaction is cooled to ambient temperature. 5N sodium hydroxide (25 mL, 125 mmol) is added and the mixture is stirred for 2 minutes. The reaction is diluted with EtOAc, and the organic layer is washed three times with saturated aqueous sodium chloride solution, dried over MgSO₄, filtered, and concentrated in vacuo. The residue is purified via silica gel chromatography eluting with hexane and acetone, collecting the second eluting diastereomer to give the title compound (7.74 g, 38%). ES/MS m/z ($^{35}$Cl/$^{37}$Cl) 424.0/426.0 [M+H]⁺.

Preparation 72

Benzyl N—[(S)-[6-chloro-7-[(1S)-2-methoxy-1-[(4S)-2-oxo-4-(trifluoromethyl)imidazolidin-1-yl]ethyl]imidazo[1,2-b]pyridazin-2-yl]-(4,4-difluorocyclohexyl)methyl]carbamate

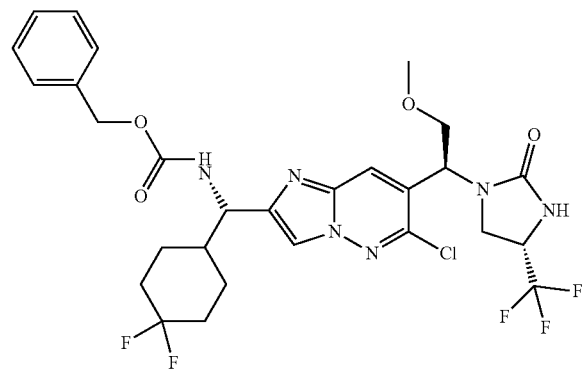

Scheme 13, steps H and I: To a solution of N-[6-chloro-5-[(1S)-2-methoxy-1-[(4S)-2-oxo-4-(trifluoromethyl)imidazolidin-1-yl]ethyl]pyridazin-3-yl]-2,2-dimethyl-propanamide (7.7 g, 18 mmol) in MeOH (20 mL) in a 2 neck round-bottom flask with reflux condenser is added 5M aqueous hydrochloric acid (70 mL, 350 mmol). The mixture is heated at 110° C. for 30 minutes. After cooling, the reaction mixture is concentrated in vacuo, then co-evaporated once with MeOH. The residue is then dissolved in a minimal amount of MeOH and diluted with EtOAc. The mixture is basified upon the addition of 5N NaOH, which is then extracted three times with EtOAc. The combined organic layers are dried over MgSO₄, filtered, and concentrated in vacuo to afford the crude amine, which is used in the next step without purification. ES/MS m/z ($^{35}$Cl/$^{37}$Cl) 340.0/342.0 [M+H]⁺.

The crude amine is dissolved in THF (100 mL) along with benzyl N-[(1S)-3-bromo-1-(4,4-difluorocyclohexyl)-2-oxopropyl]carbamate (7.71 g, 19.1 mmol) and sodium bicarbonate (4.1 g, 48 mmol). The resulting mixture is heated at 70° C. and stirred under nitrogen overnight. The mixture is cooled to room temperature, the resulting solids are filtered off of the reaction, and washed with DCM. The filtrate is concentrated in vacuo and the resulting residue is purified via silica gel chromatography eluting with DCM and MeOH to give the title compound (9.04 g, 77%). ES/MS m/z ($^{35}$Cl/$^{37}$Cl) 645.2/647.2 [M+H]⁺.

Preparation 73

(4S)-1-[(1S)-1-[2-[(S)-Amino-(4,4-difluorocyclohexyl)methyl]imidazo[1,2-b]pyridazin-7-yl]-2-methoxy-ethyl]-4-(trifluoromethyl)imidazolidin-2-one; hydrochloride

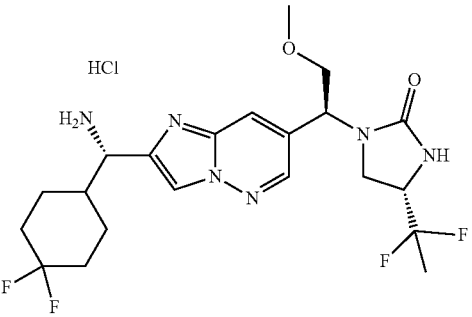 [SMILES: COC[C@H](c1cnn2cc([C@@H](N)C3CCC(F)(F)CC3)nc2c1)N1C[C@@H](C(C)(F)F)NC1=O ; Cl]

Scheme 13, step J: To a pressure bottle is added 5% palladium on carbon (2.1 g, 0.99 mmol). To the catalyst is added benzyl N—[(S)-[6-chloro-7-[(1S)-2-methoxy-1-[(4S)-2-oxo-4-(trifluoromethyl)imidazolidin-1-yl]ethyl]imidazo[1,2-b]pyridazin-2-yl]-(4,4-difluorocyclohexyl)methyl]carbamate (9.0 g, 13.12 mmol) as a solution in chilled MeOH (100 mL) under nitrogen. The bottle is purged with nitrogen, then charged with hydrogen gas (20 psi), and stirred at ambient temperature overnight. After this time, the reaction mixture is filtered through diatomaceous earth, which is further rinsed with MeOH. The filtrate is concentrated in vacuo. To the crude product is added 2-propanol (50 mL) and the mixture is stirred at ambient temperature for 10 minutes. The resulting suspension is cooled to −78° C. for 10 minutes, filtered, and the solids rinsed with 1:1 hexane/ether (200 mL), then further washed with hexanes. The resulting white solid is dried under nitrogen pressure to give the title compound as a white solid (5.86 g, 87%). ES/MS (m/z): 477.2 (M+H).

Preparation 74

[3-Chloro-6-(2,2-dimethylpropanoylamino)pyridazin-4-yl]methyl-4-methylbenzenesulfonate

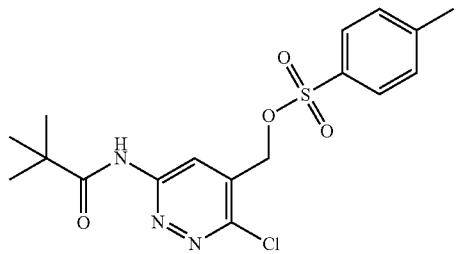 [SMILES: Cc1ccc(S(=O)(=O)OCc2cc(NC(=O)C(C)(C)C)nnc2Cl)cc1]

Scheme 14, steps A-B: N-(6-Chloropyridazin-3-yl)-2,2-dimethyl-propanamide (42.1 g, 197 mmol) and MeOH (0.50 L) are added to a 3-neck flask and the solution is heated to 80° C. To the reaction mixture is slowly added water (250 mL) over 25 minutes and the mixture is stirred for 15 minutes. Separately, a solution of ammonium persulfate (67 g, 293.6 mmol) in water (250 mL) is prepared and left to warm to ambient temperature before it is added to the reaction over approximately 35 minutes via addition funnel. The reaction is then stirred for an additional 45 minutes and removed from heat. To the reaction is added a solution of sodium sulfite (50 g, 396.7 mmol) in water (250 mL) in a thin stream over 10 minutes. The reaction mixture is left to stir overnight at ambient temperature. The mixture is then filtered, and the solids are washed with 2:1 MeOH/water (100 mL) followed by water (100 mL). The filtrate is then transferred to a separatory funnel and extracted with isopropyl acetate (300 mL, then 200 mL). The aqueous layer is discarded, and the combined organic extracts are washed with a 1:1 solution of 2M aqueous $K_2CO_3$ and saturated aqueous sodium chloride solution (100 mL). The combined organics are filtered, then coevaporated with acetonitrile (2×250 mL) to obtain an orange oil. The resulting crude oil is stirred at ambient temperature and water (25 mL) is added dropwise. Solid product is seeded into the mixture and a further 100 mL water is added. After stirring a further 10 minutes, additional water (100 mL) is added over 10 minutes and the mixture is stirred overnight. The resulting solid is collected via filtration and washed with water (100 mL). The filtrate is filtered once more, and the resulting solids are combined with the initially collected lot of solids and dried under vacuum (10 mbar, 40° C.) for four days. The resulting crude solid is used in the subsequent step without further purification (12.53 g, approximately 80 mass % purity). ES/MS m/z ($^{35}Cl/^{37}Cl$) 244.0/246.0 [M+H]$^+$.

The resulting solid (12.45 g, 40.9 mmol, 80 mass % purity) is slurried in acetonitrile (60 mL) and stirred at ambient temperature. To the mixture is added TEA (9 mL, 64.6 mmol) and DMAP (250 mg, 2.0 mmol), resulting in a brown solution. The reaction is cooled in an ice bath, and para-toluenesulfonic anhydride (15.2 g, 45.2 mmol) is added in four equal portions. After approximately 35 minutes, a small portion of previously made product is added as seed crystals. 2M aqueous potassium hydrogen sulfate (40 mL, 80 mmol) is diluted into water (120 mL) and added in a thin stream. The resulting slurry is stirred for 2 hours and 20 minutes at ambient temperature. The solids are collected via filtration, rinsed with 25% aqueous acetonitrile (100 mL), then water (100 mL). The solids are dried in a vacuum oven (40° C., 10 mbar) overnight to give the title compound as a white solid (16.97 g, 20% over 2 steps). ES/MS m/z ($^{35}Cl/^{37}Cl$) 398.0/400.0 [M+H]$^+$.

Preparation 75

N-[6-Chloro-5-[[(4S)-2-oxo-4-(trifluoromethyl)imidazolidin-1-yl]methyl]pyridazin-3-yl]-2,2-dimethyl-propanamide

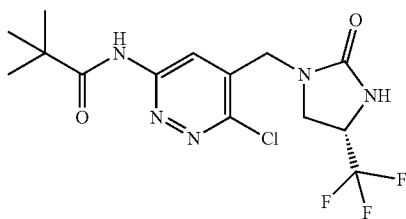 [SMILES: CC(C)(C)C(=O)Nc1cc(CN2C[C@@H](C(F)(F)F)NC2=O)c(Cl)nn1]

Scheme 14, steps C-D: To a 1 L flask equipped with a mechanical stirrer, temperature probe, and nitrogen inlet is added (2S)-3,3,3-trifluoropropane-1,2-diamine; dihydrochloride (26.3 g, 131 mmol) and potassium phosphate tribasic (69 g, 325 mmol). To the solids is added DMSO (220 mL), and the mixture is placed in an ambient temperature water bath to maintain an internal temperature of 24° C. To the mixture is added [3-chloro-6-(2,2-dimethylpropanoylamino)pyridazin-4-yl]methyl 4-methylbenzenesulfonate (43.9 g, 108 mmol) followed by additional DMSO (25 mL) to rinse the walls of the flask. The reaction is stirred overnight. The mixture is cooled to approximately 10° C. in an ice water bath and CDI (45 g, 272 mmol) is added in four equal portions in intervals of approximately 10 minutes. Following complete addition, the mixture is stirred for 35 minutes, whereupon additional CDI (5 g, 30.2 mmol) is added. The reaction is stirred for a further 5 minutes, then water (50 mL) is added and the mixture is stirred for 1 hour. To the solution is added sodium hydroxide (5N aqueous solution, 50 mL, 250 mmol) and the mixture is stirred 2.5 hours. To the resulting solution is added water (440 mL) via addition funnel over 10 minutes, causing a white solid to disperse during the addition. The resulting suspension is stirred for 1 hour, then the solids are collected via filtration and washed with 25% aqueous DMSO (400 mL) followed by water (600 mL). The crude solids are dried under vacuum to obtain an impure product. The solids are then added to a 1 L flask and slurried in cyclopentyl methyl ether (650 mL). A condenser is attached and the mixture heated to 110° C. for 4.5 hours. Heating is stopped and the mixture is allowed to cool with stirring for 4 hours and 40 minutes. The resulting solids are collected via filtration and washed with cyclopentyl methyl ether (100 mL). The solid is dried in a vacuum oven overnight (50° C., 10 mbar) to give the title compound as a white powder (30.2 g, 71%). ES/MS m/z ($^{35}Cl/^{37}Cl$) 380.1/382.1 [M+H]$^+$.

Preparation 76

(4S)-1-[(6-Amino-3-chloro-pyridazin-4-yl)methyl]-4-(trifluoromethyl)imidazolidin-2-one

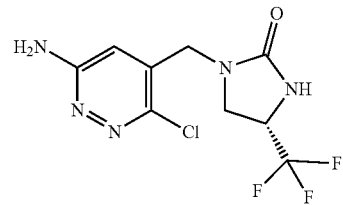 [SMILES: Nc1cc(CN2C[C@@H](C(F)(F)F)NC2=O)c(Cl)nn1]

Scheme 14, step E: A suspension of N-[6-chloro-5-[[(4S)-2-oxo-4-(trifluoromethyl)imidazolidin-1-yl]methyl]pyridazin-3-yl]-2,2-dimethyl-propanamide (30.0 g, 77.4 mmol) in MeOH (75 mL) is added to a solution of concentrated hydrochloric acid (75 mL, 873.2 mmol) diluted into water (75 mL). The mixture is heated at 70° C. with stirring for 7 hours, then allowed to stir at room temperature for a further 9.5 hours. To the mixture is added ammonium hydroxide (28% aqueous solution, 150 mL, 1100 mmol) over 10 minutes, resulting in the formation of a precipitate. The mixture is stirred for 5.5 hours, and the solids are collected via filtration and rinsed with water (150 mL). The solids are air dried, then further dried in a vacuum oven (10 mbar, 50° C.) to give the title compound (20.2 g, 87%). ES/MS m/z ($^{35}Cl/^{37}Cl$) 296.0/298.0 [M+H]$^+$.

Preparation 77

Benzyl N—[(S)-[6-chloro-7-[[(4S)-2-oxo-4-(trifluoromethyl)imidazolidin-1-yl]methyl]imidazo[1,2-b]pyridazin-2-yl]-(4,4-difluorocyclohexyl)methyl]carbamate

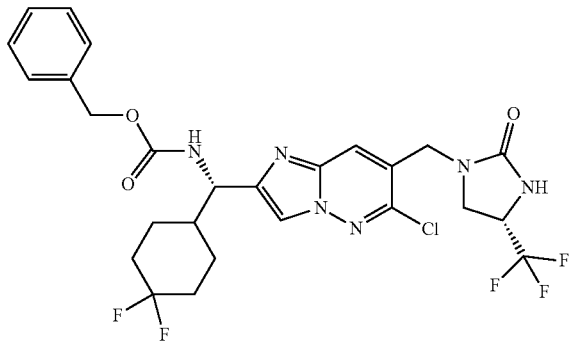 [SMILES: O=C(N[C@H](c1cn2nc(Cl)c(CN3C[C@@H](C(F)(F)F)NC3=O)cc2n1)C1CCC(F)(F)CC1)OCc1ccccc1]

Scheme 14, step F: To a flask is added (4S)-1-[(6-amino-3-chloro-pyridazin-4-yl)methyl]-4-(trifluoromethyl)imidazolidin-2-one (23.88 g, 80.8 mmol), benzyl N-[(1S)-3-bromo-1-(4,4-difluorocyclohexyl)-2-oxo-propyl]carbamate (38.0 g, 94.0 mmol), THF (400 mL), and sodium bicarbonate (23.0 g, 273.8 mmol). The mixture is heated at 65° C. After 6.25 hours, additional benzyl N-[(1S)-3-bromo-1-(4, 4-difluorocyclohexyl)-2-oxo-propyl]carbamate (2.0 g, 4.9 mmol) is added. The reaction mixture is heated for an additional 16 hours then cooled to ambient temperature. The resulting solids are filtered and rinsed with DCM. The resulting filtrate is then combined with a second reaction mixture performed on a 93.6 mmol scale. The combined filtrates are concentrated in vacuo and purified via silica gel chromatography eluting with 2-5% MeOH and DCM. The purified material is coevaporated with n-heptane to give the title compound as a light orange solid (97 g, 91%). ES/MS m/z ($^{35}$Cl/$^{37}$Cl) 601.0/603.0 [M+H]$^+$.

Preparation 78

(4S)-1-[[2-[(S)-Amino-(4,4-difluorocyclohexyl)methyl]imidazo[1,2-b]pyridazin-7-yl]methyl]-4-(trifluoromethyl)imidazolidin-2-one; hydrochloride

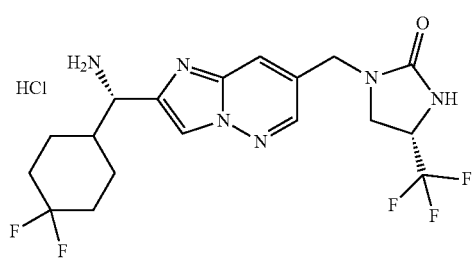 [SMILES: N[C@H](c1cn2ncc(CN3C[C@@H](C(F)(F)F)NC3=O)cc2n1)C1CCC(F)(F)CC1 ; Cl]

Scheme 14, step G: To a flask containing benzyl N—[(S)-[6-chloro-7-[[(4S)-2-oxo-4-(trifluoromethyl)imidazolidin-1-yl]methyl]imidazo[1,2-b]pyridazin-2-yl]-(4,4-difluorocyclohexyl)methyl]carbamate (15.1 g, 23.4 mmol) and 10% palladium on carbon (6.49 g, 3.05 mmol) under an atmosphere of nitrogen is added MeOH (140 mL). The flask is evacuated and backfilled with hydrogen gas from a balloon. Hydrogen is then bubbled through the solution from a balloon for approximately 10 minutes and the mixture is stirred under balloon hydrogen pressure overnight. The resulting mixture is filtered through diatomaceous earth and rinsed through the filter cake with EtOH (300 mL) followed by DCM (100 mL). The filtrate is concentrated under reduced pressure to obtain an orange foam. To the residue is added 2-propanol (400 mL) and the material is heated to reflux until it becomes nearly homogeneous. The resulting solution is then cooled to ambient temperature, then placed in a −20° C. freezer overnight. The resulting slurry is filtered, and the solids are washed with 1:1 diethyl ether:n-heptane (125 mL). The solids are air dried, then transferred to a container and dried further in a vacuum oven to give the title compound as a white solid (8.98 g, 82%). LCMS (m/z): ES/MS (m/z): 433.0 (M+H).

Preparation 79

N-[6-Chloro-5-(trimethylsilylmethyl)pyridazin-3-yl]-2,2-dimethyl-propanamide

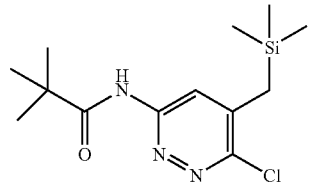 [SMILES: CC(C)(C)C(=O)Nc1cc(C[Si](C)(C)C)c(Cl)nn1]

Scheme 15, step A: To a 4 L jacketed fixed reactor equipped with overhead stirring, internal temperature probe, and nitrogen blanket, is added DIEA (195 mL, 1.39 mol) and THF (500 mL). The solution is cooled to −30° C. using a dry ice/acetone bath, and n-butyllithium (2.5 M in hexanes, 500 mL, 1.30 mol) is added dropwise while maintaining an internal temperature between −20° C. and −15° C. The mixture is stirred for 10 minutes, then a solution of N-(6-chloro-5-methyl-pyridazin-3-yl)-2,2-dimethyl-propanamide (125.0 g, 549 mmol) in THF (500 mL) is added dropwise over approximately 30 minutes while maintaining an internal temperature between −20° C. and −15° C. The resulting dark red mixture is stirred for an additional 10 minutes. Chlorotrimethylsilane (80 mL, 629 mmol) is the added while maintaining an internal temperature below −20° C. After 30 minutes, the reaction is allowed to warm to 0° C. over 30 minutes, at which point the reaction mixture is slowly poured into saturated aqueous NH$_4$Cl (1 L) and cooled in an ice bath, keeping the temperature below 10° C. The mixture is stirred vigorously for 10 minutes and the phases are separated. The aqueous layer is discarded and the organic layer is washed with saturated aqueous NH$_4$Cl (2×1 L), followed by saturated aqueous sodium chloride solution (500 mL). The organic layer is then dried over Na$_2$SO$_4$, filtered, and concentrated in vacuo to minimal volume. The crude residue is diluted with n-heptane (500 mL) and concentrated in vacuo to remove most of the hexanes and THF. The resultant suspension is stirred at room temperature overnight. The slurry is then concentrated to approximately 1 vol heptane (250 g total weight), placed in an ice bath, and stirred for 2 hours. The slurry is then filtered and the solids are rinsed with cold n-heptane (100 mL) and dried under nitrogen pressure with vacuum suction to give the title compound as a white solid (91.3 g, 56%). ES/MS m/z ($^{35}$Cl/$^{37}$Cl) 300.0/302.0 [M+H]$^+$.

Preparation 80

N-[6-Chloro-5-(chloromethyl)pyridazin-3-yl]-2,2-dimethyl-propanamide

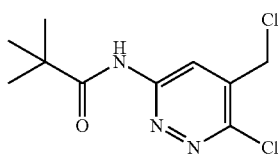 [SMILES: CC(C)(C)C(=O)Nc1cc(CCl)c(Cl)nn1]

Scheme 15, step B: To a solution of N-[6-chloro-5-(trimethylsilylmethyl)pyridazin-3-yl]-2,2-dimethyl-propanamide (37.1 g, 124 mmol) in 2-propanol (500 mL) is added NCS (17.26 g, 129.3 mmol) followed by DMF (100 mL). The mixture is stirred for 1.5 hours at ambient temperature, during which time the mixture becomes homogeneous. The reaction is slowly poured into a flask containing ice water (2 L) and saturated aqueous NaHCO$_3$ (500 mL) and a white precipitate is formed. The mixture is stirred vigorously while an additional 1 L deionized water is added. The resulting solid is then collected via filtration washed with water (3×500 mL). The solid is dried under nitrogen pressure and further dried in a vacuum oven (40° C., 10 mbar) to give the title compound as a white powder (27.6 g, 85%). ES/MS m/z ($^{35}$Cl/$^{37}$Cl) 262.0/264.0 [M+H]$^+$.

Preparation 81

N-[6-Chloro-5-[[(4S)-2-oxo-4-(trifluoromethyl)imidazolidin-1-yl]methyl]pyridazin-3-yl]-2,2-dimethyl-propanamide

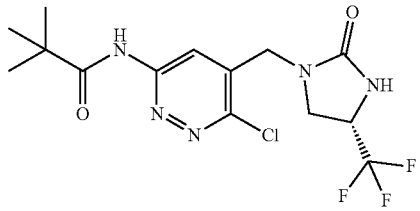 [SMILES: CC(C)(C)C(=O)Nc1cc(CN2C[C@@H](C(F)(F)F)NC2=O)c(Cl)nn1]

Scheme 15, steps C-D: To a solution of N-[6-chloro-5-(chloromethyl)pyridazin-3-yl]-2,2-dimethyl-propanamide (28.6 g, 109.1 mmol) in acetonitrile (720 mL) is added (2S)-3,3,3-trifluoropropane-1,2-diamine; dihydrochloride (24.1 g, 120.0 mmol) followed by DIEA (76 mL, 436 mmol) and sodium iodide (16.4 g). The reaction is stirred at ambient temperature for 2.25 hours, at which point additional (2S)-3,3,3-trifluoropropane-1,2-diamine; dihydrochloride (2.5 g, 12.4 mmol) and DIEA (5 mL, 28.6 mmol) are added. The reaction is stirred overnight then concentrated in vacuo to a total volume of approximately 100 mL. To the mixture is added saturated aqueous NaHCO$_3$, which is then extracted three times with DCM. The combined organic layers are washed with 1:1 saturated aqueous NaHCO$_3$ and saturated aqueous sodium chloride solution, dried over MgSO$_4$, filtered, and concentrated in vacuo to give an orange solid that is used without further purification.

The resulting residue is suspended in THF (400 mL) and heated to 65° C. To the reaction is added CDI (45.0 g, 277.5 mmol) portionwise. After 15 minutes, the reaction mixture is removed from heat and carefully quenched upon the slow portionwise addition of water (50 mL). Once gas evolution subsides, the mixture is heated to 65° C. and stirred for 20 minutes. The reaction mixture is concentrated in vacuo to remove approximately 150 mL solvent, then the mixture is poured slowly into a 4 L flask containing ice water (2 L) with rapid stirring, causing a tan precipitate to form. The mixture is diluted further with water (700 mL) and stirred for 10 minutes. The cold suspension is filtered and the solids are washed with water (approximately 500 mL). The solids are air dried, then washed with diethyl ether (200 mL then 50 mL). The resulting white powder is dried under nitrogen pressure with vacuum suction, then further dried in a vacuum oven to give the title compound (34.26 g, 82%). ES/MS m/z ($^{35}$Cl/$^{37}$Cl) 380.0/382.0 [M+H]$^+$.

EXAMPLE 1

3-Cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide

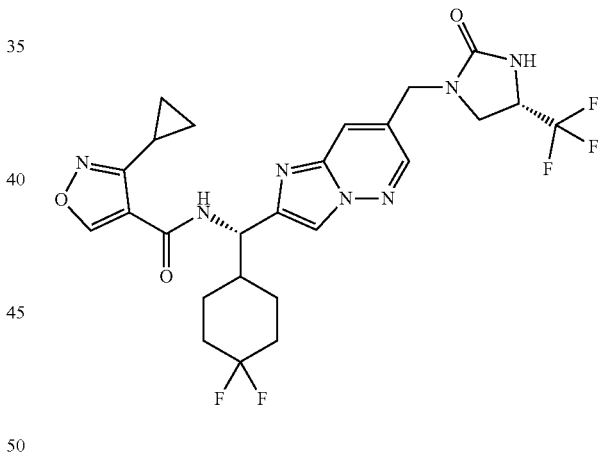

Scheme 12, step C: To a vial is added HATU (151 mg, 0.395 mmol), 3-cyclopropylisoxazole-4-carboxylic acid (64 mg, 0.397 mmol), and THF (5 mL). The slurry is stirred for 5 minutes and DIEA (172 μL, 0.99 mmol) is added. After an additional 10 minutes, (4S)-1-[[2-[(S)-amino-(4,4-difluorocyclohexyl)methyl]imidazo[1,2-b]pyridazin-7-yl]methyl]-4-(trifluoromethyl)imidazolidin-2-one (151 mg, 0.396 mmol) is added and the reaction is stirred for 1 hour at ambient temperature. The solvent is removed in vacuo, and the crude material is purified by reverse phase purification [column: 86 g C18; eluent: gradient of 35% to 45% acetonitrile in 10 mM ammonium bicarbonate solution w/5% MeOH (pH 10.0)] to give the title compound (150 mg, 70%). ES/MS (m/z): 568.2 (M+H).

EXAMPLE 2

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-ethyl-isoxazole-4-carboxamide

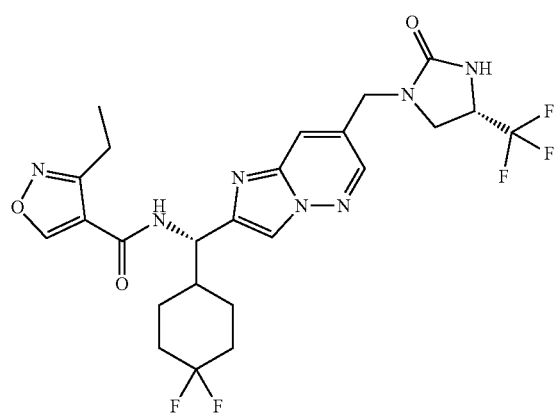 [SMILES: CCc1nocc1C(=O)N[C@H](c1cn2ncc(CN3C[C@@H](C(F)(F)F)NC3=O)cc2n1)C1CCC(F)(F)CC1]

Scheme 12, step C: The title compound is prepared from 3-ethylisoxazole-4-carboxylic acid in a manner essentially analogous to the method of Example 1. ES/MS (m/z): 556.2 (M+H).

EXAMPLE 3

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-methyl-isoxazole-4-carboxamide

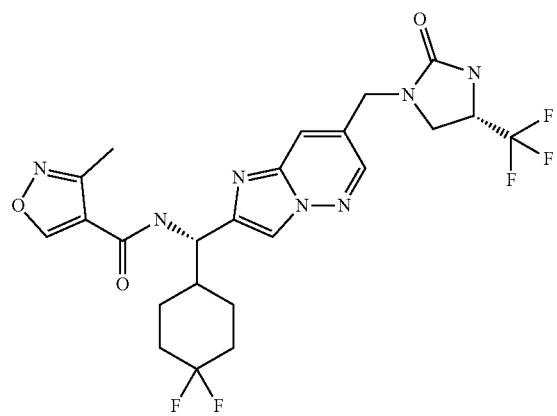 [SMILES: Cc1nocc1C(=O)N[C@H](c1cn2ncc(CN3C[C@@H](C(F)(F)F)NC3=O)cc2n1)C1CCC(F)(F)CC1]

Scheme 12, step C: The title compound is prepared from 3-methylisoxazole-4-carboxylic acid in a manner essentially analogous to the method of Example 1. ES/MS (m/z): 542.2 (M+H).

EXAMPLE 4

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(difluoromethyl)isoxazole-4-carboxamide

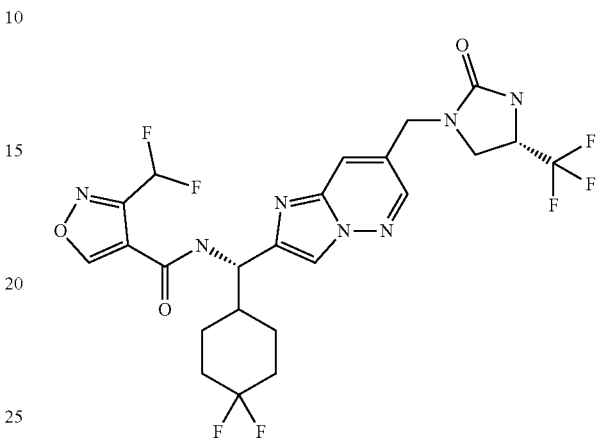

Scheme 12, step C: The title compound is prepared from 3-(difluoromethyl)isoxazole-4-carboxylic acid in a manner essentially analogous to the method of Example 1 (preparation of this acid is described in *Eur. J. Org. Chem.* 2017, 3935-3940). ES/MS (m/z): 578.0 (M+H).

EXAMPLE 5

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(1,1-difluoroethyl)isoxazole-4-carboxamide

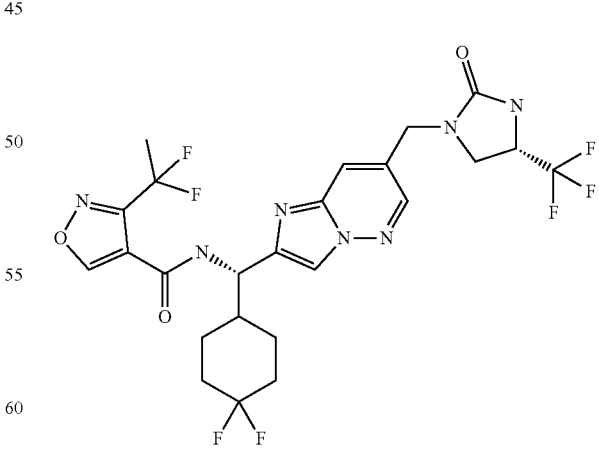

Scheme 12, step C: The title compound is prepared from 3-(1,1-difluoroethyl)isoxazole-4-carboxylic acid in a manner essentially analogous to the method of Example 1. ES/MS (m/z): 592.0 (M+H).

EXAMPLE 6

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-4-methyl-1,2,5-oxadiazole-3-carboxamide

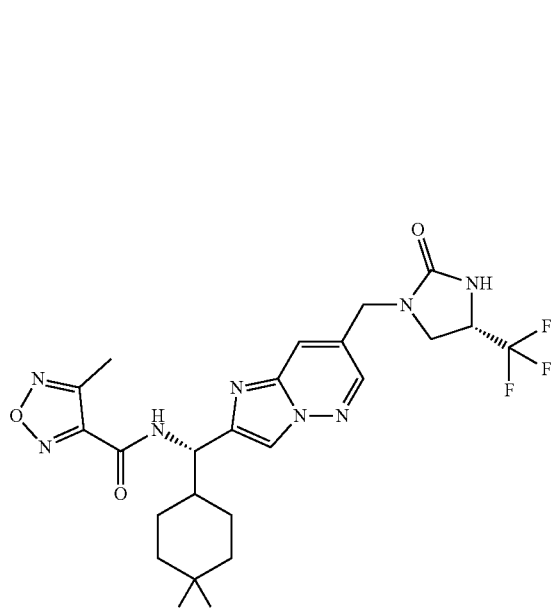

Scheme 12, step C: In a vial, 4-methyl-1,2,5-oxadiazole-3-carboxylic acid (490 mg, 3.825 mmol) and HATU (1.30 g, 3.42 mmol) are dissolved in DMF (10 mL) and cooled in a −40° C. dry ice/acetone bath. To the mixture is added TEA (850 uL, 6.10 mmol), and the mixture is stirred for 2 minutes. At this time, the reaction contents are transferred via syringe to a flask containing (4S)-1-[[2-[(S)-Amino-(4,4-difluorocyclohexyl)methyl]imidazo[1,2-b]pyridazin-7-yl]methyl]-4-(trifluoromethyl)imidazolidin-2-one (988 mg, 2.28 mmol), and the reaction is allowed to stir at ambient temperature. After approximately 50 minutes, the mixture is diluted with EtOAc (150 mL), transferred to a separatory funnel, and washed with a 1:1 solution of saturated aqueous sodium chloride and saturated aqueous sodium bicarbonate, then once further with saturated aqueous sodium chloride. Aqueous layers are back extracted once with EtOAc. The combined organic layers are dried over magnesium sulfate, and filtered. The solvent is removed in vacuo, and the crude material is purified by reverse phase purification [column: 275 g C18; eluent: gradient of 35% to 60% acetonitrile in 10 mM ammonium bicarbonate solution] to give the title compound (710 mg, 57%). ES/MS (m/z): 543.1 (M+H).

EXAMPLE 7

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(fluoromethyl)isoxazole-4-carboxamide

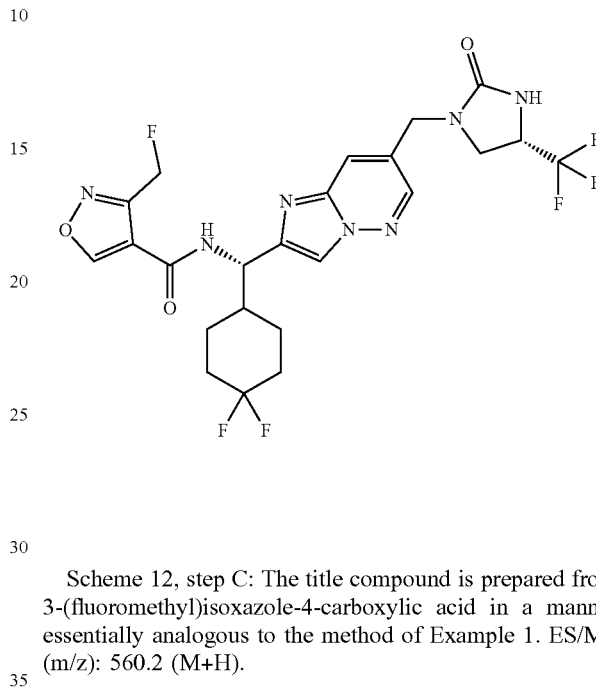

Scheme 12, step C: The title compound is prepared from 3-(fluoromethyl)isoxazole-4-carboxylic acid in a manner essentially analogous to the method of Example 1. ES/MS (m/z): 560.2 (M+H).

EXAMPLE 8

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(2,2-difluoroethyl)isoxazole-4-carboxamide

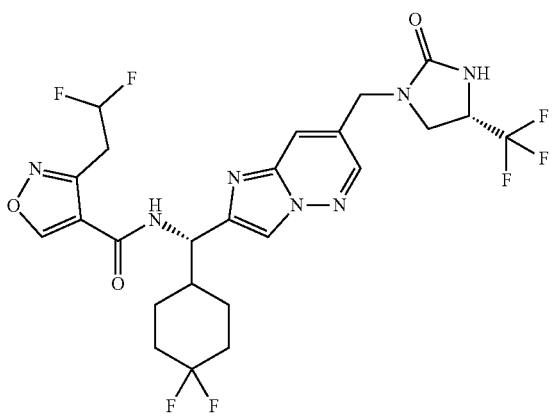 [SMILES: O=C(N[C@H](c1cn2ncc(CN3C[C@@H](C(F)(F)F)NC3=O)cc2n1)C1CCC(F)(F)CC1)c1conc1CC(F)F]

Scheme 12, step C: The title compound is prepared from 3-(2,2-difluoroethyl)isoxazole-4-carboxylic acid in an essentially analogous manner to the method of Example 1. ES/MS (m/z): 592.2 (M+H).

EXAMPLE 9

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(2-fluoroethyl)isoxazole-4-carboxamide

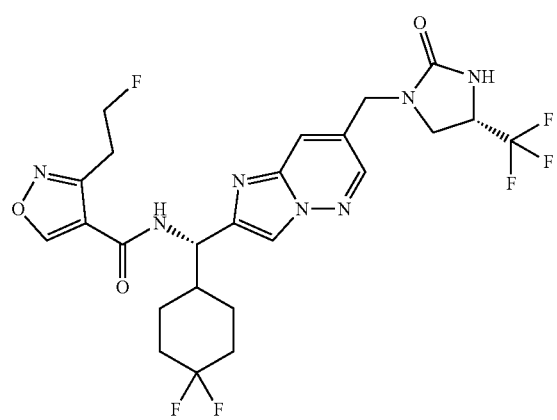 [SMILES: O=C(N[C@H](c1cn2ncc(CN3C[C@@H](C(F)(F)F)NC3=O)cc2n1)C1CCC(F)(F)CC1)c1conc1CCF]

Scheme 12, step C: The title compound is prepared from 3-(2-fluoroethyl)isoxazole-4-carboxylic acid in an essentially analogous manner to the method of Example 1. ES/MS (m/z): 574.2 (M+H).

EXAMPLE 10

3-(3,3-Difluorocyclobutyl)-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide

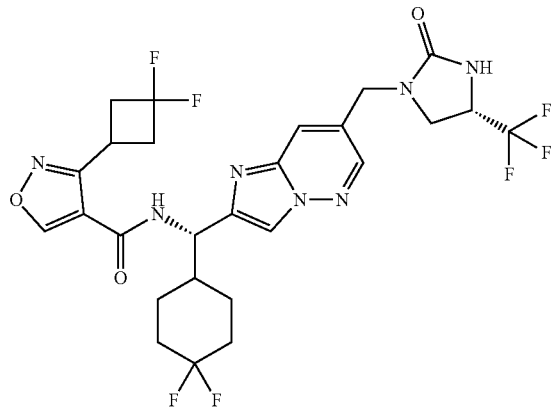 [SMILES: O=C(N[C@H](c1cn2ncc(CN3C[C@@H](C(F)(F)F)NC3=O)cc2n1)C1CCC(F)(F)CC1)c1conc1C1CC(F)(F)C1]

Scheme 12, step C: The title compound is prepared from 3-(3,3-difluorocyclobutyl)isoxazole-4-carboxylic acid in an essentially analogous manner to the method of Example 1. ES/MS (m/z): 618.1 (M+H).

EXAMPLE 11

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(trifluoromethyl)isoxazole-4-carboxamide

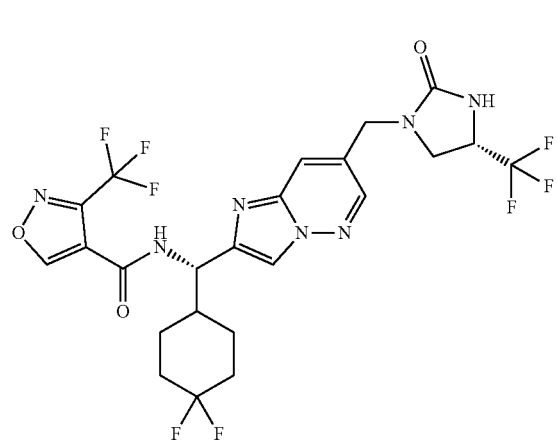

Scheme 12, step C: The title compound is prepared from 3-(trifluoromethyl)isoxazole-4-carboxylic acid in an essentially analogous manner to the method of Example 1. ES/MS (m/z): 596.1 (M+H).

EXAMPLE 12

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(1-fluorocyclopropyl)isoxazole-4-carboxamide

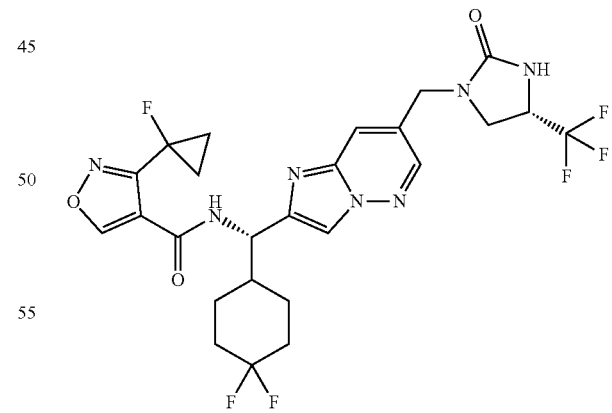

Scheme 12, step C: The title compound is prepared from 3-(1-fluorocyclopropyl)isoxazole-4-carboxylic acid in an essentially analogous manner to the method of Example 1. ES/MS (m/z): 586.2 (M+H).

EXAMPLE 13

3-[Cyclopropyl(difluoro)methyl]-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide

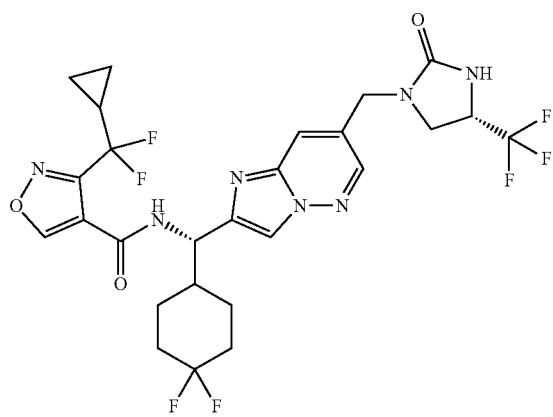 [SMILES: O=C(N[C@H](c1cn2ncc(CN3C[C@@H](C(F)(F)F)NC3=O)cc2n1)C1CCC(F)(F)CC1)c1conc1C(F)(F)C1CC1]

Scheme 12, step C: The title compound is prepared from 3-[cyclopropyl(difluoro)methyl]isoxazole-4-carboxylic acid in an essentially analogous manner to the method of Example 1. ES/MS (m/z): 618.3 (M+H).

EXAMPLE 14

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(1-methylcyclopropyl)isoxazole-4-carboxamide

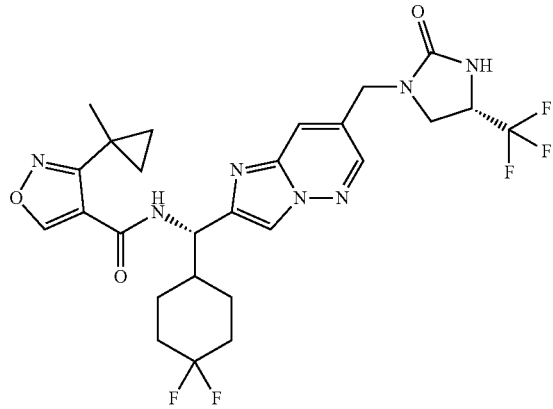 [SMILES: CC1(c2nocc2C(=O)N[C@H](c2cn3ncc(CN4C[C@@H](C(F)(F)F)NC4=O)cc3n2)C2CCC(F)(F)CC2)CC1]

Scheme 12, step C: The title compound is prepared from 3-(1-methylcyclopropyl)isoxazole-4-carboxylic acid in an essentially analogous manner to the method of Example 1. ES/MS (m/z): 582.2 (M+H).

EXAMPLE 15

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-(1-fluoro-1-methyl-ethyl)isoxazole-4-carboxamide

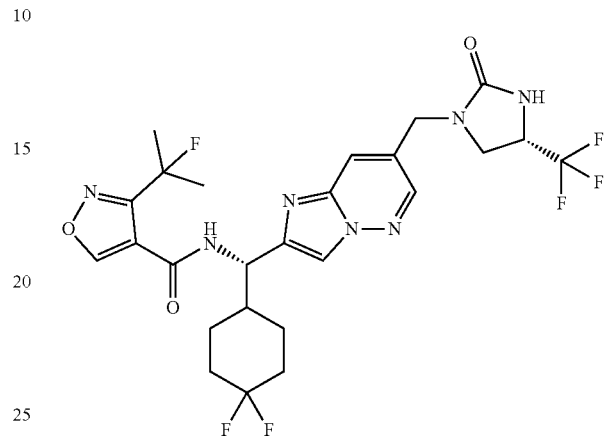

Scheme 12, step C: The title compound is prepared from 3-(1-fluoro-1-methyl-ethyl)isoxazole-4-carboxylic acid in an essentially analogous manner to the method of Example 1. ES/MS (m/z): 588.2 (M+H).

EXAMPLE 16

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-3-isopropyl-isoxazole-4-carboxamide

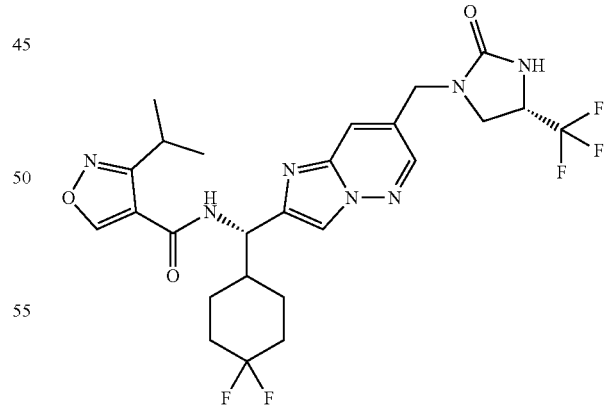

Scheme 12, step C: The title compound is prepared from 3-isopropylisoxazole-4-carboxylic acid in an essentially analogous manner to the method of Example 1. ES/MS (m/z): 570.2 (M+H).

EXAMPLE 17

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-4-ethyl-1,2,5-oxadiazole-3-carboxamide

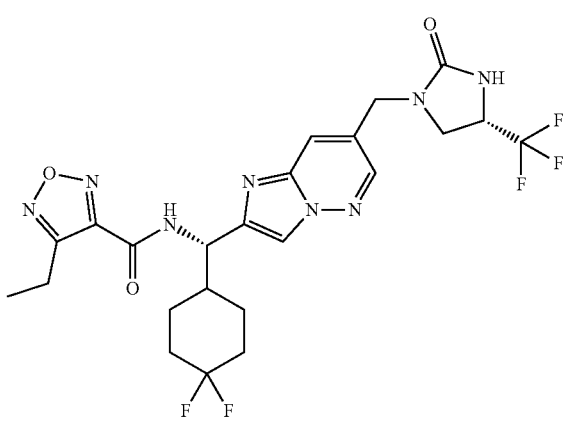 [SMILES: CCc1nonc1C(=O)N[C@H](c1cn2ncc(CN3C[C@@H](C(F)(F)F)NC3=O)cc2n1)C1CCC(F)(F)CC1]

Scheme 12, step C: The title compound is prepared from 4-ethyl-1,2,5-oxadiazole-3-carboxylic acid in a manner essentially analogous to the method of Example 6. ES/MS m/z 557.2 (M+H).

EXAMPLE 18

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-4-(difluoromethyl)-1,2,5-oxadiazole-3-carboxamide

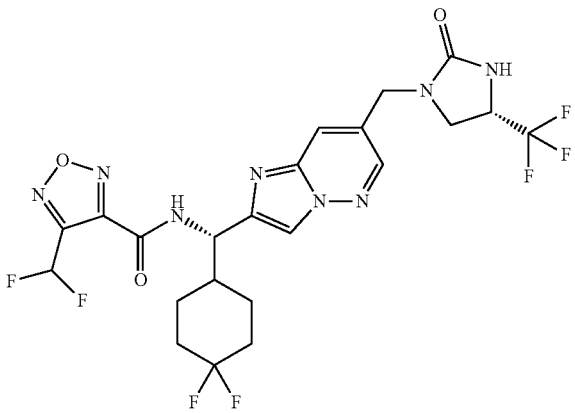 [SMILES: O=C(N[C@H](c1cn2ncc(CN3C[C@@H](C(F)(F)F)NC3=O)cc2n1)C1CCC(F)(F)CC1)c1nonc1C(F)F]

Scheme 12, step C: The title compound is prepared from 4-(difluoromethyl)-1,2,5-oxadiazole-3-carboxylic acid in a manner essentially analogous to the method of Example 6. ES/MS m/z 579.0 (M+H).

EXAMPLE 19

4-Cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide

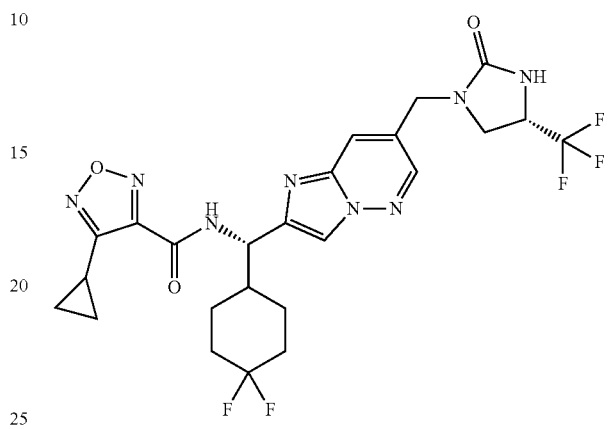

Scheme 12, step C: Ethyl 4-cyclopropyl-1,2,5-oxadiazole-3-carboxylate (75 mg, 0.41 mmol) is dissolved in THF (4.0 mL) and water (2.0 mL), then aqueous LiOH (1.0 M, 0.45 mL, 0.45 mmol) is added. The mixture is stirred at ambient temperature for 4 hours, then additional aqueous LiOH (1.0 M, 0.25 mL, 0.25 mmol) is added. After stirring for 1 hour at ambient temperature, the mixture is concentrated in vacuo. Toluene is added and concentrated in vacuo. The residue is dissolved in DMF (1.6 mL) and cooled to −30° C. in an acetonitrile/dry ice bath. HATU (0.31 g, 0.84 mmol) is added, the mixture is stirred for 5 minutes at −30° C., then the bath is removed. Upon reaching 0° C., (4S)-1-[[2-[(S)-Amino-(4,4-difluorocyclohexyl)methyl]imidazo[1,2-b]pyridazin-7-yl]methyl]-4-(trifluoromethyl)imidazolidin-2-one (175 mg, 0.41 mmol) is added, and the reaction is allowed to warm to ambient temperature. After 1 hour, the mixture is diluted with EtOAc, transferred to a separatory funnel, and washed with 1:1 water/saturated aqueous sodium bicarbonate followed by saturated aqueous sodium chloride. The organic layer is dried over sodium sulfate, filtered, and concentrated in vacuo. The crude material is purified by silica gel flash chromatography eluting with acetone and hexane to give the title compound (130 mg, 56%). ES/MS (m/z) 569.2 (M+H).

EXAMPLE 19A

Preparation of 4-Cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide; ethanesulfonic acid The esylate salt of 4-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide is prepared by dissolving 4-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide (1.8 g, 3.166 mmol) (Example 19) in EtOAc (10 mL)

while stirring at 800 rpm at ambient temperature to a clear yellowish solution. This solution is filtered through a 0.45 μm syringe filter into a new clean vial. To this solution is added of 95% ethanesulfonic acid (300 μL, 3.473 mmol) and the clear solution persists. The solution begins to cloud within minutes. After an hour, a thick slurry of white solid forms, and another 10 mL of EtOAc is added to thin the slurry slightly. This slurry is allowed to stir at 800 rpm overnight. A thick slurry of bright white solid results. The white solid is isolated on a Whatman paper filter under vacuum. The cake of bright white solid is dried in place for 15 minutes under nitrogen stream, then kept overnight in a 70° C. vacuum oven to give the title compound (1.283 g, 59.7%).

X-Ray Powder Diffraction of Crystalline Forms

The XRPD patterns of crystalline solids are obtained on a Bruker D4 Endeavor X-ray powder diffractometer, equipped with a CuKα source and a Vantec detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is known to the skilled artisan of the crystallography art, that for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged (See, e.g. The United States Pharmacopeia #23, National Formulary #18, pages 1843-1844, 1995). Furthermore, it is also known to the skilled artisan of the crystallography art, that for any given crystal form, the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

X-Ray Powder Diffraction of Crystalline 4-Cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide; ethanesulfonic acid A prepared sample of crystalline Example 19a (4-Cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide; ethanesulfonic acid) is characterized by an X-Ray powder diffraction pattern using CuKα radiation as having diffraction peaks (2-theta values) as described in Table A below, and in particular having peaks at 19.2 in combination with one or more of the peaks selected from the group consisting of 19.7, 6.5, and 8.4; with a tolerance for the diffraction angles of 0.2 degrees.

TABLE A

X-ray powder diffraction peaks of crystalline 4-Cyclopropyl-N-[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide; ethanesulfonic acid

| Peak | Angle (°2-Theta) +/− 0.2° | Relative Intensity (% of most intense peak) |
|---|---|---|
| 1 | 6.5 | 83.7% |
| 2 | 7.9 | 52.3% |
| 3 | 8.4 | 58.7% |
| 4 | 15.9 | 27.8% |
| 5 | 18.2 | 43.4% |
| 6 | 19.2 | 100.0% |
| 7 | 19.7 | 97.5% |
| 8 | 22.5 | 18.9% |
| 9 | 23.9 | 43.0% |
| 10 | 25.6 | 25.2% |

EXAMPLE 20

4-Isopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide

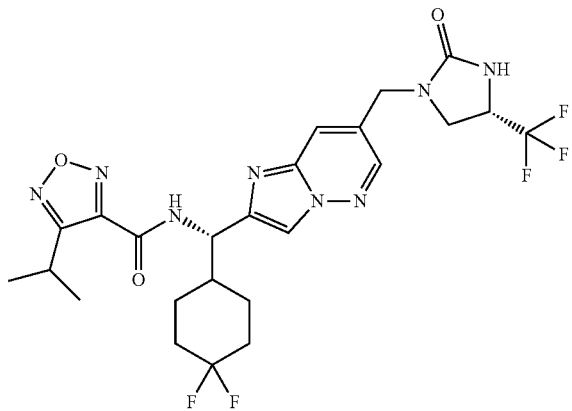 [SMILES: CC(C)c1nonc1C(=O)N[C@H](c1cn2ncc(CN3C[C@@H](C(F)(F)F)NC3=O)cc2n1)C1CCC(F)(F)CC1]

Scheme 12, step C: The title compound is prepared from Ethyl 4-isopropyl-1,2,5-oxadiazole-3-carboxylate in a manner essentially analogous to the method of Example 19. ES/MS (m/z) 571.2 (M+H).

EXAMPLE 21

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-4-(trifluoromethyl)-1,2,5-oxadiazole-3-carboxamide

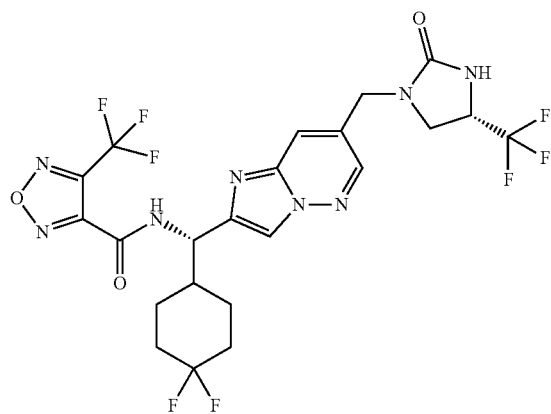 [SMILES: O=C(N[C@H](c1cn2ncc(CN3C[C@@H](C(F)(F)F)NC3=O)cc2n1)C1CCC(F)(F)CC1)c1nonc1C(F)(F)F]

Scheme 12, step C: A mixture of ethyl 4-(trifluoromethyl)-1,2,5-oxadiazole-3-carboxylate (61 mg, 0.29 mmol) and (4S)-1-[[2-[(S)-amino-(4,4-difluorocyclohexyl)methyl]imidazo[1,2-b]pyridazin-7-yl]methyl]-4-(trifluoromethyl)imidazolidin-2-one (55.7 mg, 0.129 mmol) in acetonitrile (0.17 mL) is heated in a sealed vial at 90° C. After stirring for 16 hours, the reaction is cooled and purified by silica gel flash chromatography eluting with hexane and acetone to obtain an impure product. The resulting residue is then purified via reverse phase HPLC [Acetonitrile/10 mM $(NH_4)_2CO_3$ (pH 10)] to give the title compound as a white solid (22 mg, 29%). ES/MS (m/z) 597.2 (M+H).

EXAMPLE 22

N—[(S)-(4,4-Difluorocyclohexyl)-[7-[[(4S)-2-oxo-4-(trifluoromethyl)imidazolidin-1-yl]methyl]imidazo[1,2-b]pyridazin-2-yl]methyl]-4-methoxy-1,2,5-oxadiazole-3-carboxamide

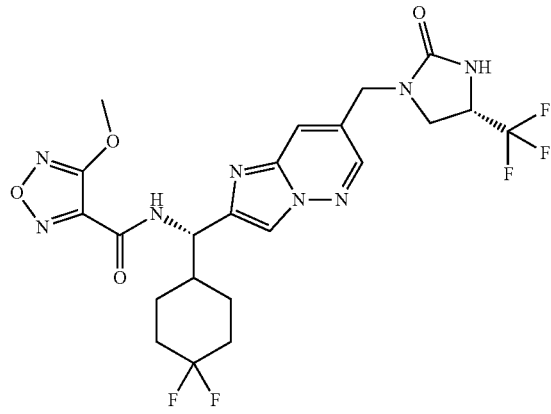 [SMILES: COc1nonc1C(=O)N[C@H](c1cn2ncc(CN3C[C@@H](C(F)(F)F)NC3=O)cc2n1)C1CCC(F)(F)CC1]

Scheme 12, step C: To tert-butyl N-(4-methoxy-1,2,5-oxadiazole-3-carbonyl)-N-methyl-carbamate (65 mg, 0.25 mmol) is added a solution of (4S)-1-[[2-[(S)-amino-(4,4-difluorocyclohexyl)methyl]imidazo[1,2-b]pyridazin-7-yl]methyl]-4-(trifluoromethyl)imidazolidin-2-one (100 mg, 0.23 mmol) in acetonitrile (2 mL). The mixture is heated to 60° C. for 40 minutes, then to 80° C. for 18 hours. The mixture is concentrated in vacuo and purified via silica gel flash chromatography eluting with 7 N ammonia in MeOH and DCM to give the title compound as a yellow foam (94 mg, 73% yield). ES/MS (m/z) 559.2 (M+H).

EXAMPLE 23

N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-4-(2,2,2-trifluoroethyl)-1,2,5-oxadiazole-3-carboxamide

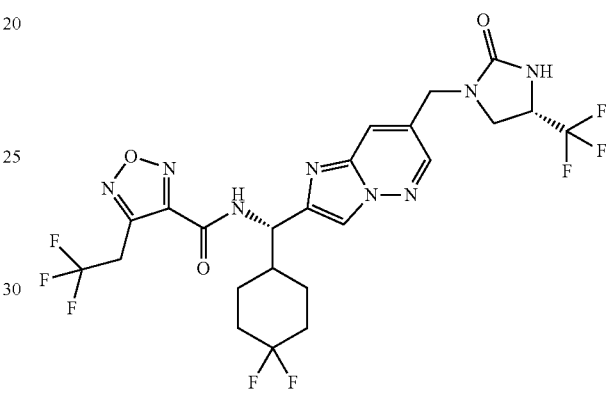

Scheme 12, step C: The title compound is prepared from ethyl 4-(2,2,2-trifluoroethyl)-1,2,5-oxadiazole-3-carboxylate in a manner essentially analogous to the method of Example 19. ES/MS (m/z): 611.2 (M+H).

EXAMPLE 24

N—[(S)-(4,4-Difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide

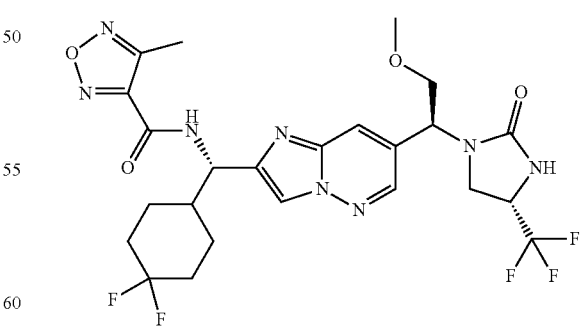

Scheme 13, step K: To a suspension of (4S)-1-[(1S)-1-[2-[(S)-amino-(4,4-difluorocyclohexyl)methyl]imidazo[1,2-b]pyridazin-7-yl]-2-methoxy-ethyl]-4-(trifluoromethyl)imidazolidin-2-one; hydrochloride (7.5 g, 15 mmol) in EtOAc (150 mL) is added triethylamine (8.2 mL, 58 mmol). After stirring for five minutes, 4-methyl-1,2,5-oxadiazole-3-carboxylic acid (2.2 g, 17 mmol) is added followed by propylphosphonic anhydride (1.67 M solution in EtOAc, 26 mL, 43.4 mmol). After stirring at ambient temperature for 1 hour, additional 4-methyl-1,2,5-oxadiazole-3-carboxylic acid (640 mg, 5 mmol), triethylamine (0.70 mL, 5 mmol) and propylphosphonic anhydride (1.67 M solution in EtOAc, 3 mL, 5 mmol) are added. After stirring an addition hour, the reaction is quenched with water followed by saturated aqueous NaHCO$_3$. The mixture is stirred for 5 minutes, transferred to a separatory funnel, and the layers are separated. The aqueous layer is extracted twice more with EtOAc, and the combined organic layers are washed with saturated aqueous NaHCO$_3$ followed by saturated aqueous sodium chloride solution. The organic layers are dried over MgSO$_4$, filtered, and concentrated in vacuo. The crude material is purified via silica gel chromatography eluting with DCM and MeOH to obtain an impure product which is repurified via silica gel chromatography eluting with DCM and EtOH to give the title compound as a white solid (6.61 g, 77%). ES/MS (m/z): 587.2 (M+H).

EXAMPLE 24A

Preparation of N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide; hemi-ethane-1,2-disulfonic acid A hemi-edisylate salt of N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide is prepared by dissolving N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide (2.92 g, 4.98 mmol) (See Example 24) in acetonitrile (10 mL) to a clear yellow solution, then filtering through a 0.45 μm syringe filter into a new clean vial. 1,2-Ethanedisulfonic acid dihydrate (580 mg, 2.513 mmol) is dissolved in acetonitrile (20 mL) at 80° C. While stirring at 800 rpm at 60° C. this clear colorless ethanedisulfonic acid solution is added quickly then hot filtered through a 0.45 μm syringe filter into the clear yellow solution of the compound. The clear yellow solution turns rapidly to a hazy slurry of white solid under yellow supernatant. With the full addition of the acid, a thick slurry of white solid in yellow supernatant results. This slurry is stirred at 800 rpm/60° C. for 30 minutes. Heat is shut off and the sample is stirred at 300 rpm as it cools to room temp. A thick layer of bright white solid results under yellow supernatant. The white solid is isolated on a Whatman paper filter under vacuum. The cake of bright white solid is dried in place for 15 minutes under nitrogen stream, then for 1 hour in a 70° C. vacuum oven to give the compound (3.03 g, 89.3%).

X-Ray Powder Diffraction of Crystalline N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide; hemi-ethane-1,2-disulfonic acid (Example 24a)

The XRPD patterns of crystalline solids are obtained as described in Example 19a. A prepared sample of crystalline Example 24a (N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide; hemi-ethane-1,2-disulfonic acid) is characterized by an XRD pattern using CuKα radiation as having diffraction peaks (2-theta values) as described in Table B below, and in particular having peaks at 17.1 in combination with one or more of the peaks selected from the group consisting of 7.6, 19.4, and 10.7; with a tolerance for the diffraction angles of 0.2 degrees.

TABLE B

X-ray powder diffraction peaks of crystalline N-[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-methyl-1,2,5-oxadiazole-3-carboxamide; hemi-ethane-1,2-disulfonic acid

| Peak | Angle (°2-Theta) +/− 0.2° | Relative Intensity (% of most intense peak) |
|---|---|---|
| 1 | 7.6 | 76.4% |
| 2 | 8.2 | 17.5% |
| 3 | 10.7 | 54.9% |
| 4 | 16.8 | 52.1% |
| 5 | 17.1 | 100.0% |
| 6 | 17.9 | 28.3% |
| 7 | 19.4 | 64.1% |
| 8 | 22.6 | 25.8% |
| 9 | 23.8 | 22.6% |
| 10 | 24.3 | 24.5% |

EXAMPLE 25

4-Cyclopropyl-N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-1,2,5-oxadiazole-3-carboxamide

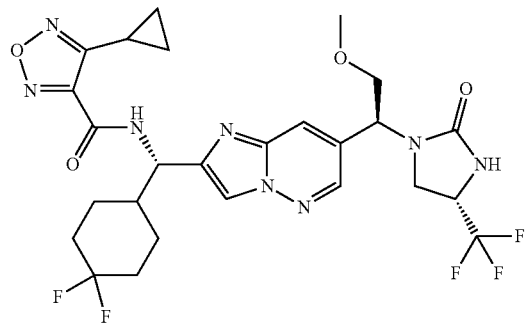 [SMILES: COC[C@H](c1cnn2cc([C@@H](NC(=O)c3nonc3C3CC3)C3CCC(F)(F)CC3)nc2c1)N1C[C@@H](C(F)(F)F)NC1=O]

Scheme 13, step K: The title compound is prepared from 4-cyclopropyl-1,2,5-oxadiazole-3-carboxylic acid in a manner essentially analogous to the method of Example 24. ES/MS (m/z): 613.2 (M+H)

EXAMPLE 26

3-Cyclopropyl-N—[(S)-(4,4-difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]isoxazole-4-carboxamide

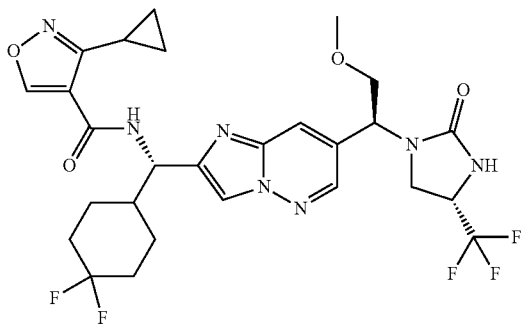 [SMILES: COC[C@H](c1cnn2cc([C@@H](NC(=O)c3conc3C3CC3)C3CCC(F)(F)CC3)nc2c1)N1C[C@@H](C(F)(F)F)NC1=O]

Scheme 13, step K: The title compound is prepared from 3-cyclopropylisoxazole-4-carboxylic acid in a manner essentially analogous to the method of Example 24. ES/MS (m/z): 612.2 (M+H)

EXAMPLE 27

N—[(S)-(4,4-Difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-(difluoromethyl)-1,2,5-oxadiazole-3-carboxamide

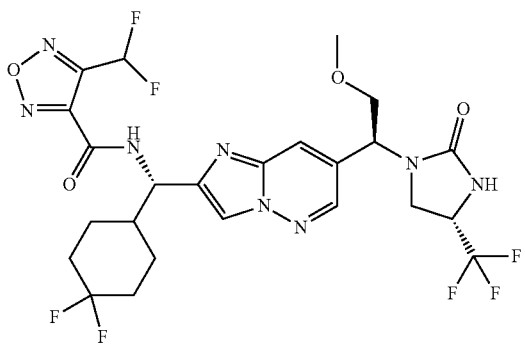 [SMILES: COC[C@H](c1cnn2cc([C@@H](NC(=O)c3nonc3C(F)F)C3CCC(F)(F)CC3)nc2c1)N1C[C@@H](C(F)(F)F)NC1=O]

Scheme 13, step K: In a separatory funnel, a solution of (4S)-1-[(1S)-1-[2-[(S)-amino-(4,4-difluorocyclohexyl)methyl]imidazo[1,2-b]pyridazin-7-yl]-2-methoxy-ethyl]-4-(trifluoromethyl)imidazolidin-2-one; hydrochloride (80% mass purity, 1.0 g, 1.56 mmol) in EtOAc is washed twice with saturated aqueous NaHCO₃. The organic layer is dried over MgSO₄, filtered, and concentrated in vacuo to afford the corresponding freebase, which is used without further purification. ES/MS (m/z): 477.2 (M+H).

The resulting amine and ethyl 4-(difluoromethyl)-1,2,5-oxadiazole-3-carboxylate (750 mg, 3.12 mmol) are combined in a vial, dissolved in MeOH (10 mL), and 4-dimethylaminopyridine (400 mg, 3.24 mmol) is added. The vial is sealed, and the mixture is stirred at 70° C. for 9 hours, then allowed to continue stirring at ambient temperature overnight. The crude reaction mixture is concentrated and purified via reverse phase chromatography (360 g C18 column; Solvent A: 0.1% aq. HCO₂H, Solvent B: acetonitrile; 30-100% Solvent B over 39 minutes). Product containing fractions are concentrated in vacuo to remove volatiles and the resulting aqueous mixture is neutralized with saturated aqueous NaHCO₃. The mixture is extracted three times with EtOAc, and the combined organic layers are dried over MgSO4, filtered, and concentrated in vacuo to give the title compound as a tan solid (113 mg, 12%). ES/MS (m/z): 623.2 (M+H).

EXAMPLE 28

N—[(S)-(4,4-Difluorocyclohexyl)-[7-[(1S)-2-methoxy-1-[(4S)-2-oxo-4-(trifluoromethyl)imidazolidin-1-yl]ethyl]imidazo[1,2-b]pyridazin-2-yl]methyl]-4-(trifluoromethyl)-1,2,5-oxadiazole-3-carboxamide

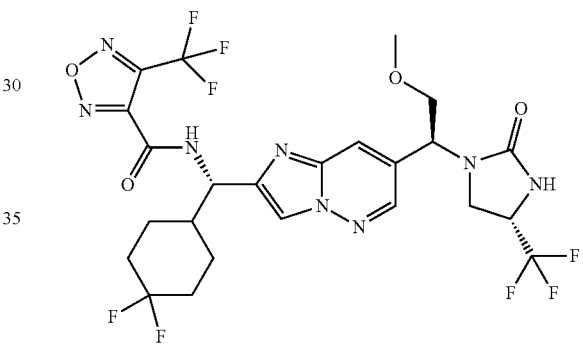

Scheme 13, step K: The title compound is prepared from ethyl 4-(trifluoromethyl)-1,2,5-oxadiazole-3-carboxylate in a manner essentially analogous to the method of Example 27 (121 mg, 82%). ES/MS (m/z): 641.2 (M+H).

IL-17A:IL-17RA AlphaLISA

The ability of compounds to inhibit the binding of IL-17A to IL-17RA may be assessed with an AlphaLISA assay. Expression and purification of protein reagents IL17A and IL17RA for alphaLISA may be carried out essentially as follows. A construct of cytokine IL-17A (Reference sequence NP_002181) residues 1-155 with a C-terminal AVI-tag, followed by a His tag, is expressed in insect cells, together with BirA for in vivo biotinylation. Receptor IL-17RA (NP_055154) residues 1-317 with mutations N206D/N265D is expressed in insect cells with a C-terminal thrombin cleavage site followed by a FLAG-tag. IL-17A and IL-17RA are each PCR amplified and TOPO cloned into custom TOPO adapted pFastBac vectors (Thermo Fisher Scientific. Carlsbad, Calif.).

TABLE 1

SEQ ID Numbers for IL17A, BirA, and IL17RA Construct Sequences

| Amino Acid Sequence for: | SEQ ID NO: |
|---|---|
| IL 17A residues 1-155 + AVI-tag + His-tag (Reference sequence NP_002181) | 1 |
| BirA (for in vivo biotinylation) | 2 |
| IL17RA residues 1-317 with mutations N206D, N265D + Thrombin cleavage site + FLAG-tag (NP_055154) | 3 |

Standard baculovirus expression using a modified version of the Bac to Bac system protocol (Thermo Fisher Scientific. Carlsbad, Calif.) in combination with the DH10EMBacY bacmid (Geneva Biotech. Geneva, Switzerland) is used to generate virus. Fermentations of IL-17A and IL-17RA in Sf9 cells are 72 hrs in length. The resulting proteins are harvested by centrifugation and supernatants are transferred for purification. IL-17A is isolated from supernatant by nickel affinity chromatography, and further purified by size exclusion chromatography. IL-17RA is isolated from supernatant by FLAG affinity chromatography, and further purified by size exclusion chromatography.

To assay the compounds of the present invention, 0.1 μL of a test compound stock is serially diluted in 100% DMSO using an Echo Acoustic Liquid Handler (LabCyte Sunnydale, Calif.) in 384 well proxiplates (Perkin Elmer). A 5 μL addition of IL-17RA-FLAG is added to the plate, followed by the addition of 5 μL Avi-tagged IL-17A-His to provide a final concentration of 2 nM of IL-17RA and IL-17A, respectively. The assay is carried out in 20 mM HEPES, 150 mM NaCl, 0.05% Tween-20, 0.1% Human Serum Albumin, pH 7 and 1% DMSO. The assay mixture is allowed to incubate at room temperature for 2 hours. After the 2 hour incubation, 10 μL of streptavidin donor beads (20 μg/ml final) and anti-FLAG acceptor beads (20 μg/ml final) are added to the plate. The plate is allowed to incubate for one hour at room temp, then is read on the Envision (Perkin Elmer). The relative $IC_{50}$ values are determined using a four parameter fit as shown in equation 1. In this equation, bottom and top are defined as the plateaus of the curve, and H is the Hill Slope. No inhibitory effect is observed from addition of 0.1% DMSO only.

$$Y = Y_{bottom} + (Y_{top} - Y_{bottom})/1 + 10^{(\log IC50 - x)*H)}$$

The $IC_{50}$ values provided for Examples 1-28 in Table 2 illustrate inhibition of IL-17 receptor mediated signaling in response to IL-17A, and illustrate the activity of the compounds of Claim 1 as inhibitors of the binding of IL-17A to IL-17RA, and thus as inhibitors of IL-17A-mediated signaling.

Cell-Based Human IL-17A Neutralization Assay

The ability of compounds to neutralize the activity of IL-17A may be assessed with a cell-based human IL-17A neutralization assay conducted essentially as follows. HT-29 cells (#HTB-38; ATCC) are plated in a 96 well plate (#3596; Costar) at 20,000 cells per well in McCoy's 5A (Modified) medium (#16600-082; Gibco) supplemented with 10% FBS. Cells are treated with 90 ng/mL human IL-17A (#317-ILB; R&D Systems) in the presence of inhibitor at the indicated concentrations. A dose range of 0.06 nM to 16,000 nM is evaluated. After 48 hours, CXCL1/GROα in the culture media is measured using a commercial ELISA kit (#DY275; R&D Systems). Medium alone treatments are included in every experiment to assess the basal levels of CXCL1/GROα. Percent inhibition is calculated using the following equation:

$$\left( \frac{[CXCL1]_{IL17A} - [CXCL1]_{compound+IL17A}}{[CXCL1]_{IL17A} - [CXCL1]_{medium\ alone}} \right) \times 100$$

The $IC_{50}$ values provided for Examples 1-28 in Table 2 illustrate neutralization human IL-17A mediated signaling in HT-29 cells, and illustrate the activity of the compounds of Claim 1 as inhibitors of IL-17A.

TABLE 2

$IC_{50}$ values provided for Examples 1-28

| Compound | alphalisa $IC_{50}$ | HT-29 $IC_{50}$ |
|---|---|---|
| Example 1 | 15.7 ± 7.0 nM (n = 6) | 51.6 ± 23.5 nM (n = 7) |
| Example 2 | 15.2 ± 2.5 nM (n = 2) | 53.3 ± 26.4 nM (n = 3) |
| Example 3 | 27.7 ± 2.4 nM (n = 4) | 127 nM (n = 1) |
| Example 4 | 13.0 ± 2.0 nM (n = 4) | 93.7 nM (n = 1) |
| Example 5 | 20.0 nM (n = 1) | 104 nM (n = 1) |
| Example 6 | <9.45 nM (n = 1) | 94.2 nM (n = 1) |
| Example 7 | 37.8 nM (n = 1) | 128 nM (n = 1) |
| Example 8 | 15.5 nM (n = 1) | 52.4 nM (n = 1) |
| Example 9 | 10.6 nM (n = 1) | 46.5 nM (n = 1) |
| Example 10 | 47 nM (n = 1) | 48.9 nM (n = 1) |
| Example 11 | <9.45 nM (n = 1) | 148 nM (n = 1) |
| Example 12 | 18.1 nM (n = 1) | 107 nM (n = 1) |
| Example 13 | 47.1 nM (n = 1) | 53.1 nM (n = 1) |
| Example 14 | 36.1 nM (n = 1) | 33.3 nM (n = 1) |
| Example 15 | 51.9 nM (n = 1) | 82.9 nM (n = 1) |
| Example 16 | 19.3 nM (n = 4) | 10.8 nM (n = 1) |
| Example 17 | <9.45 nM (n = 1) | 15.9 nM (n = 1) |
| Example 18 | <9.45 nM (n = 1) | 22.7 nM (n = 1) |
| Example 19 | <9.45 nM (n = 1) | 10.1 nM (n = 1) |
| Example 20 | <9.45 nM (n = 1) | 14.3 nM (n = 1) |
| Example 21 | <9.45 nM (n = 1) | 10.1 nM (n = 1) |
| Example 22 | 11.4 nM (n = 1) | 83.4 nM (n = 1) |
| Example 23 | <9.45 nM (n = 1) | 14.9 nM (n = 1) |
| Example 24 | <9.45 nM (n = 3) | 9.3 ± 6.0 nM (n = 4) |
| Example 25 | <9.45 nM (n = 2) | 2.2 ± 1.6 nM (n = 4) |
| Example 26 | <9.45 nM (n = 1) | 7.0 nM (n = 1) |
| Example 27 | <9.45 nM (n = 1) | 2.8 nM (n = 1) |
| Example 28 | <9.45 nM (n = 1) | 4.6 nM (n = 1) |

Mouse Oral Bioavailability

Oral bioavailability (% F) for compounds of the invention may be determined in mice by determination of an 8-hour blood plasma AUC (nM*hr) following intravenous and oral administration performed essentially as follows. Male mice (n=3) are administered compound via intravenous (IV) bolus (1 mg/kg) or orally (3 mg/kg). For intravenous administration, a vehicle of 20% w/v capsitol in $NaPO_4$ buffer (25 mM) adjusted to pH 2 in a volume of 5 mL/kg is used. For oral administration, a vehicle of HEC/P80/AF/PW (probe sonicated to afford a homogeneous suspension) in a volume of 10 mL/kg is used. Blood is sampled by saphenous bleeding using K2 EDTA as anticoagulant. Approximately 20 μL of blood (or enough for 1 spot) is collected via a capillary tube and transferred to a card as a dry blood spot. Cards are allowed to dry for at least 2 hours before shipping for analysis. Blood concentration of compounds for each mouse is measured by liquid chromatography/tandem mass spectrometry at time points of 0.08 (IV only), 0.25, 0.5, 0.75, 2, 4, and 8 hours. Oral bioavailability (% F) is determined via the following equation: [% F=(AUC/Dose)$_{PO}$/(AUC/Dose)$_{IV}$]. Oral bioavailability results for Example compounds 1-7, 9, 11, 19, 24 and 25 are provided in the table below as % F. These data illustrate the pharmacologically advantageous oral availability of various compounds of the invention.

| Compound | % F (mouse) |
|---|---|
| Example 1 | 34 |
| Example 2 | 28 |
| Example 3 | 35 |
| Example 4 | 59 |
| Example 5 | 49 |
| Example 6 | 75 |
| Example 7 | 47 |
| Example 9 | 12 |
| Example 11 | 55 |
| Example 19 | 47 |
| Example 24 | 107 |
| Example 25 | 37 |

Compounds of the present invention provide novel inhibitors of IL-17A mediated signaling, and demonstrate an advantageous combination of pharmacological properties such as potent inhibition of IL-17A binding to and signaling through the IL-17 receptor, oral bioavailability, and a generally favorable toxicological profile in 4 day rat studies. As such, compounds of the present invention, in particular the compounds of Formula I, and the examples provided herein, are believed to be useful in the treatment of psoriasis, rheumatoid arthritis and/or multiple sclerosis, psoriatic arthritis, axial spondyloarthritis, ankylosing spondylitis, hidradenitis suppurativa, systemic lupus erythematosus, palmoplantar pustulosis (PPP), atopic dermatitis, asthma, and COPD.

Listing of Amino Acid and Nucleotide Sequences
<SEQ ID NO: 1; PRT1; ARTIFICIAL SEQUENCE> IL17A residues 1-155 + AVI-tag + His-tag
MTPGKTSLVSLLLLLSLEAIVKAGITIPRNPGCPNSEDKNFPRTVMVNL
NIHNRNTNTNPKRSSDYYNRSTSPWNLHRNEDPERYPSVIWEAKCRHLG
CINADGNVDYHMNSVPIQQEILVLRREPPHCPNSFRLEKILVSVGCTCV
TPIVHHVAGLNDIFEAQKIEWHEHHHHHH <SEQ ID NO: 2; PRT1; ARTIFICIAL SEQUENCE> BirA
MALKDNTVPLKLIALLANGEFHSGEQLGETLGMSRAAINKHIQTLRDWG
VDVFTVPGKGYSLPEPIQLLNAKQILGQLDGGSVAVLPVIDSTNQYLLD
RIGELKSGDACIAEYQQAGRGRRGRKWFSPFGANLYLSMFWRLEQGPAA
AIGLSLVIGIVMAEVLRKLGADKVRVKWPNDLYLQDRKLAGILVELTGK
TGDAAQIVIGAGINMAMRRVEESVVNQGWITLQEAGINLDRNTLAAMLI
RELRAALELFEQEGLAPYLSRWEKLDNFINRPVKLIIGDKEIFGISRGI
DKQGALLLEQDGIIKPWMGGEISLRSAEK <SEQ ID NO: 3; PRT1; ARTIFICIAL SEQUENCE> IL17RA residues 1-317 with mutations N206D, N265D + Thrombin cleavage site + FLAG-tag
MGAARSPPSAVPGPLLGLLLLLLGVLAPGGASLRLLDHRALVCSQPGLN
CTVKNSTCLDDSWIHPRNLTPSSPKDLQIQLHFAHTQQGDLFPVAHIEW
TLQTDASILYLEGAELSVLQLNTNERLCVRFEFLSKLRHHHRRWRFTFS
HFVVDPDQEYEVTVHHLPKPIPDGDPNHQSKNFLVPDCEHARMKVTTPC
MSSGSLWDPDITVETLEAHQLRVSFTLWNESTHYQILLTSFPHMENHSC
FEHMHHIPAPRPEEFHQRSDVTLTLRNLKGCCRHQVQIQPFFSSCLNDC
LRHSATVSCPEMPDTPEPIPDYMLVPRGSDYKDDDDK

---

We claim:
1. A compound of the formula:

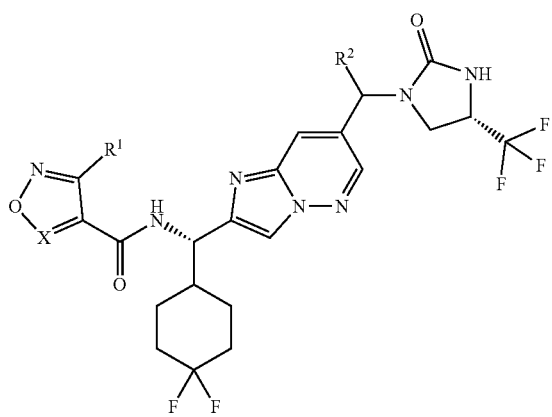

wherein:
X is CH, or N;
R¹ is —CH₃, —CH₂F, —CHF₂, —CF₃, —CH₂CH₃, —CH₂CF₃, —CH(CH₃)₂, —CH₂CHF₂, —CH₂CH₂F, —CF(CH₃)₂, —CF₂CH₃, —OCH₃,

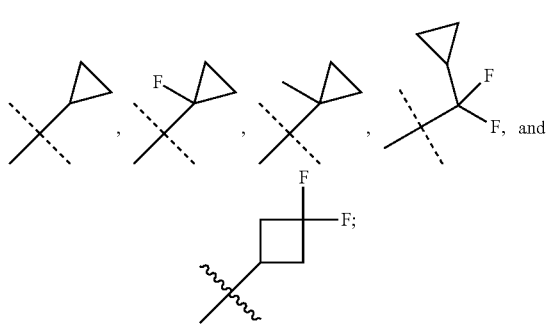

and
R² is —H or —CH₂OCH₃;
or a pharmaceutically acceptable salt thereof.

2. The compound according to claim 1 wherein X is CH, or a pharmaceutically acceptable salt thereof.

3. The compound according to claim 1 wherein X is N, or a pharmaceutically acceptable salt thereof.

4. The compound according to claim 2 or 3 wherein R² is —CH₂OCH₃, or a pharmaceutically acceptable salt thereof.

5. The compound according to claim 4 of the formula:

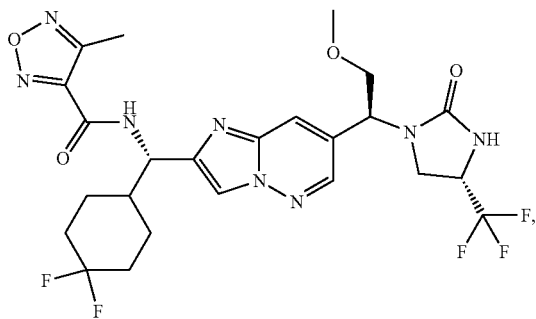 [SMILES: COC[C@H](c1cnn2cc([C@@H](NC(=O)c3nonc3C)C3CCC(F)(F)CC3)nc2c1)N1C[C@@H](C(F)(F)F)NC1=O]

or a pharmaceutically acceptable salt thereof.

6. The compound of claim 5 which is a crystalline salt of N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]-4-methyl-1,2,5-oxadiazole-3-carboxamide and hemi-ethane-1,2-disulfonic acid.

7. The compound of claim 6 which is crystalline salt of N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]-4-methyl-1,2,5-oxadiazole-3-carboxamide and hemi-ethane-1,2-disulfonic acid characterized by an X-ray powder diffraction pattern using CuKα radiation having a diffraction peak at diffraction angle 2-theta of 17.1 in combination with one or more of the peaks selected from the group consisting of 7.6, 19.4, and 10.7; with a tolerance for the diffraction angles of 0.2 degrees.

8. The compound according to claim 3 of the formula:

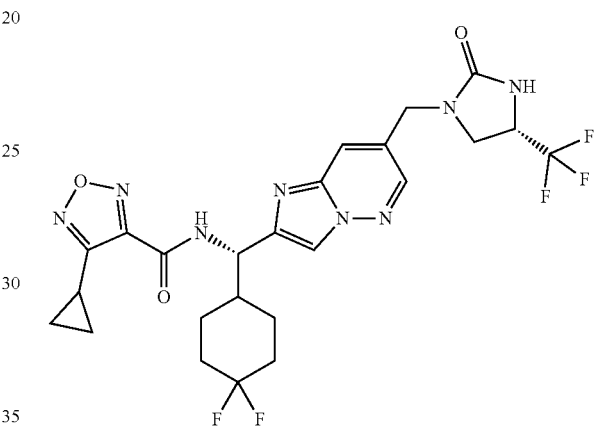

or a pharmaceutically acceptable salt thereof.

9. The compound of claim 8 which is a crystalline salt of 4-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]-1,2,5-oxadiazole-3-carboxamide and ethanesulfonic acid.

10. The compound of claim 9 which is crystalline 4-cyclopropyl-N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-1,2,5-oxadiazole-3-carboxamide; ethanesulfonic acid characterized by an X-ray powder diffraction pattern using CuKα radiation having a diffraction peak at diffraction angle 2-theta of 19.2 in combination with one or more of the peaks selected from the group consisting of 19.7, 6.5, and 8.4; with a tolerance for the diffraction angles of 0.2 degrees.

11. The compound of claim 1 selected from the group consisting of:
3-cyclopropyl-N—[(S)-(4,4-difluorocyclohexyl)-[7-[[(4S)-2-oxo-4-(trifluoromethyl)imidazolidin-1-yl]methyl]imidazo[1,2-b]pyridazin-2-yl]methyl]isoxazole-4-carboxamide;
N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-ethyl-isoxazole-4-carboxamide;
N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-methyl-isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(difluoromethyl) isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(1,1-difluoroethyl) isoxazole-4-carboxamide;

N—[(S)-(4,4-difluorocyclohexyl)-[7-[(4S)-2-oxo-4-(trifluoromethyl) imidazolidin-1-yl]methyl]imidazo[1,2-b]pyridazin-2-yl]methyl]-3-(fluoromethyl) isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(2,2-difluoroethyl) isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(2-fluoroethyl) isoxazole-4-carboxamide;

3-(3,3-difluorocyclobutyl)-N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl] isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(trifluoromethyl) isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(1-fluorocyclopropyl) isoxazole-4-carboxamide;

3-[cyclopropyl(difluoro)methyl]-N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]isoxazole-4-carboxamide;

N—[(S)-(4,4-difluorocyclohexyl)-[7-[(4S)-2-oxo-4-(trifluoromethyl) imidazolidin-1-yl]methyl]imidazo[1,2-b]pyridazin-2-yl]methyl]-3-(1-methylcyclopropyl) isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-(1-fluoro-1-methyl-ethyl) isoxazole-4-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-3-isopropyl-isoxazole-4-carboxamide;

N—[(S)-(4,4-difluorocyclohexyl)-[7-[(4S)-2-oxo-4-(trifluoromethyl) imidazolidin-1-yl]methyl]imidazo[1,2-b]pyridazin-2-yl]methyl]-4-ethyl-1,2,5-oxadiazole-3-carboxamide;

4-isopropyl-N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-1,2,5-oxadiazole-3-carboxamide;

N—[(S)-(4,4-difluorocyclohexyl)-[7-[(4S)-2-oxo-4-(trifluoromethyl) imidazolidin-1-yl]methyl]imidazo[1,2-b]pyridazin-2-yl]methyl]-4-methoxy-1,2,5-oxadiazole-3-carboxamide;

N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-4-(2,2,2-trifluoroethyl)-1,2,5-oxadiazole-3-carboxamide;

N—[(S)-(4,4-difluorocyclohexyl)-[7-[(4S)-2-oxo-4-(trifluoromethyl) imidazolidin-1-yl]methyl]imidazo[1,2-b]pyridazin-2-yl]methyl]-4-(2,2,2-trifluoroethyl)-1,2,5-oxadiazole-3-carboxamide;

4-cyclopropyl-N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]-1,2,5-oxadiazole-3-carboxamide;

3-cyclopropyl-N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]isoxazole-4-carboxamide;

N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]-4-(difluoromethyl)-1,2,5-oxadiazole-3-carboxamide; and N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]-4-(trifluoromethyl)-1,2,5-oxadiazole-3-carboxamide, or a pharmaceutically acceptable salt thereof.

12. A pharmaceutical composition comprising a compound according to any one of claims 1 to 3 or 8 to 11, or a pharmaceutically acceptable salt thereof, and a pharmaceutically acceptable carrier, diluent or excipient.

13. A method of treating psoriasis comprising administering to a patient in need thereof an effective amount of a compound of any one of claims 1 to 3 or 8 to 11, or a pharmaceutically acceptable salt thereof.

14. A method of treating psoriasis according to claim 13 comprising administering to a patient in need thereof an effective amount of N—[(S)-(4,4-difluorocyclohexyl)-[7-[(1S)-2-methoxy-1-[(4S)-2-oxo-4-(trifluoromethyl) imidazolidin-1-yl]ethyl]imidazo[1,2-b]pyridazin-2-yl]methyl]-4-methyl-1,2,5-oxadiazole-3-carboxamide, or a pharmaceutically acceptable salt thereof.

15. The method of treating psoriasis according to claim 13 comprising administering to a patient in need thereof an effective amount of 4-cyclopropyl-N—[(S)-(4,4-difluorocyclohexyl)-[7-[[(4S)-2-oxo-4-(trifluoromethyl) imidazolidin-1-yl]methyl]imidazo[1,2-b]pyridazin-2-yl]methyl]-1,2,5-oxadiazole-3-carboxamide, or a pharmaceutically acceptable salt thereof.

16. A method of treating a disease or disorder selected from the group consisting of rheumatoid arthritis, spondyloarthritis, multiple sclerosis, psoriatic arthritis, axial spondyloarthritis, ankylosing spondylitis, hidradenitis suppurativa, systemic lupus erythematosus, palmoplantar pustulosis (PPP), atopic dermatitis, asthma, or COPD comprising administering to a patient in need thereof an effective amount of a compound according to any one of claims 1 to 3 or 8 to 11, or a pharmaceutically acceptable salt thereof.

17. The method according to claim 16, wherein the compound is N—[(S)-(4,4-difluorocyclohexyl)-[7-[(1S)-2-methoxy-1-[(4S)-2-oxo-4-(trifluoromethyl) imidazolidin-1-ylethyl]imidazo[1,2-b]pyridazin-2-yl]methyl]-4-methyl-1,2,5-oxadiazole-3-carboxamide, or a pharmaceutically acceptable salt thereof.

18. The method according to claim 16 wherein the compound is 4-cyclopropyl-N—[(S)-(4,4-difluorocyclohexyl)-[7-[ ](4S)-2-oxo-4-(trifluoromethyl) imidazolidin-1-yl]methyl]imidazo[1,2-b]pyridazin-2-yl]methyl]-1,2,5-oxadiazole-3-carboxamide, or a pharmaceutically acceptable salt thereof.

\* \* \* \* \*

UNITED STATES PATENT AND TRADEMARK OFFICE
CERTIFICATE OF CORRECTION

| | |
|---|---|
| PATENT NO. | : 12,252,491 B2 |
| APPLICATION NO. | : 17/419997 |
| DATED | : March 18, 2025 |
| INVENTOR(S) | : David Andrew Coates et al. |

Page 1 of 1

It is certified that error appears in the above-identified patent and that said Letters Patent is hereby corrected as shown below:

In the Claims

In Column 99, Line 9, in Claim 11, delete "[(4S)" and insert -- [[4S) --, therefor;

In Column 99, Line 38, in Claim 11, delete "[(4S)" and insert -- [[4S) --, therefor;

In Column 99, Line 50, in Claim 11, delete "[(4S)" and insert -- [[4S) --, therefor;

In Column 99, Line 58, in Claim 11, delete "[(4S)" and insert -- [[4S) --, therefor;

In Column 100, Line 1, in Claim 11, delete "[(4S)" and insert -- [[4S) --, therefor;

In Column 100, Line 55, in Claim 17, delete "ylethyl]" and insert -- yl]ethyl] --, therefor;

In Column 100, Line 60, in Claim 18, delete "[7-[ ]" and insert -- [7-[[ --, therefor.

Signed and Sealed this
Twenty-eighth Day of October, 2025

John A. Squires
*Director of the United States Patent and Trademark Office*